United States Patent [19]

Branca et al.

[11] Patent Number: 5,250,517
[45] Date of Patent: * Oct. 5, 1993

[54] RENIN INHIBITING COMPOUNDS

[75] Inventors: Quirico Branca, Basel; Albrecht Edenhofer, Riehen, both of Switzerland; Eva-Maria Gutknecht, Buggingen-Seefelden; Werner Neidhart, Freiburg im Breisgau, both of Fed. Rep. of Germany; Henri Ramuz, Birsfelden, Switzerland; Wolfgang Wostl, Grenzach-Wyhlen, Fed. Rep. of Germany

[73] Assignee: Hoffmann-La Roche Inc., Nutley, N.J.

[*] Notice: The portion of the term of this patent subsequent to Aug. 8, 2009 has been disclaimed.

[21] Appl. No.: 879,522

[22] Filed: May 4, 1992

Related U.S. Application Data

[63] Continuation of Ser. No. 254,003, Oct. 5, 1988, abandoned.

[30] Foreign Application Priority Data

Oct. 6, 1987 [CH] Switzerland .................. 3903/87

[51] Int. Cl.$^5$ .................. C07K 5/10; C07K 5/08; C07D 235/14; A61K 37/02
[52] U.S. Cl. .................. 514/18; 514/19; 530/330; 530/331; 544/60; 544/124; 544/132; 544/139; 544/140; 544/141; 544/143; 544/284; 544/324; 544/353; 544/370; 548/150; 548/165; 548/190; 548/218; 548/266.4; 548/338.1; 548/338.5; 930/21; 930/24; 546/84; 546/153; 546/276; 546/241; 546/101; 546/104; 546/109; 546/208
[58] Field of Search .............. 548/336, 344, 150, 165, 548/190, 218, 266.4, 338.1, 338.5; 530/330, 331; 514/18, 19; 544/60, 124, 132, 139, 140, 141, 143, 284, 324, 370, 383, 212; 546/84, 153, 276, 241, 208, 104, 109, 101; 930/21, 24

[56] References Cited

U.S. PATENT DOCUMENTS

| | | | |
|---|---|---|---|
| 4,613,676 | 8/1986 | Fuhrer et al. | 560/39 |
| 4,628,329 | 10/1987 | Matsueda et al. | 514/18 |
| 4,652,551 | 3/1987 | Luly et al. | 530/330 |
| 4,713,445 | 12/1987 | Szelke et al. | 530/330 |
| 4,727,060 | 2/1988 | Buhlmayer et al. | 530/331 |
| 4,845,079 | 7/1989 | Luly et al. | 530/330 |
| 4,931,429 | 6/1990 | Hanson et al. | 514/18 |
| 5,140,011 | 8/1992 | Branca et al. | 514/19 |

FOREIGN PATENT DOCUMENTS

| | | | |
|---|---|---|---|
| 172346 | 2/1986 | European Pat. Off. | 530/330 |
| 229667 | 7/1987 | European Pat. Off. | 530/330 |
| 88/05050 | 7/1988 | World Int. Prop. O. | 514/19 |

OTHER PUBLICATIONS

Szelke, et al. Chemical Abstracts, vol. 101, 1984, Abstract 86219s.
Biochemical Soc. Trans. 10, 164 (1982).
Science, 217, 121 (1982).
Biochem. & Biophys. Res. Commun. 146(3), 959 (1987).

*Primary Examiner*—Mukund J. Shah
*Assistant Examiner*—E. C. Ward
*Attorney, Agent, or Firm*—George M. Gould; George W. Johnston; Alan P. Kass

[57] ABSTRACT

Compounds which are amino acid derivatives and have the formula

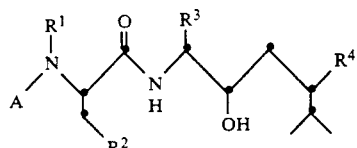

in which $R^1$ is hydrogen or methyl, $R^2$ is ethyl, propyl or imidazol-4-yl, $R^3$ is isobutyl, cyclohexylmethyl or benzyl, and A is defined as herein are useful as renin inhibitors.

11 Claims, No Drawings

RENIN INHIBITING COMPOUNDS

This application is a continuation of application Ser. No. 07/254,003, filed Oct. 5, 1988, now abandoned.

SUMMARY OF THE INVENTION

The present invention comprises compounds which are amino acid derivatives and which have the formula

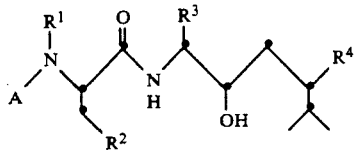

is which $R^1$ is hydrogen or methyl, $R^2$ is ethyl, propyl or imidazol-4-yl, $R^3$ is isobutyl. cyclohexylmethyl or benzyl, $R^4$ is phenyl, furyl, vinyl, ethyl or 1,2-dihydroxyethyl, and A is dibenzsuberaneacetic acid, 2 (2-pyridyl) benzoic acid, β-naphthylsuccinic acid monoethyl ester, 2-indolylacetic acid or dihydrocinnamic acid attached via the carboxyl group or A is one of the following groups:

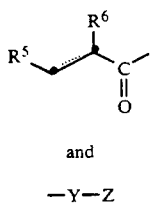

—Y—Z  (b)

in which the dotted line represents an additional chemical bond, $R^5$ is phenyl, naphthyl, indolyl, pyrazolyl, imidazolyl or pyridylmethyl, and $R^6$ is hydrogen, alkyl, arylalkyl, alkoxycarbonyl- alkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminocarbonyl, substituted aminocarbonyl, alkoxycarbonyl, alkylcarbonyloxy, arylalkylcarbonyloxy, alkylaminocarbonyloxy, alkoxycarbonylamino, cyano or 2,5-dimethylpyrrol-1-yl, with the proviso that $R^4$ is not alkoxycarbonylamino when $R^3$ is phenyl or α-naphthyl, Y is a bivalent residue of optionally N- and/or α-methylated phenylglycine, cyclohexylglycine, phenylalanine, cyclohexylalanine, 4-fluorophenyl- alanine, 4-chlorophenylalanine, tyrosine, α-naphthylalanine, homophenylalanine, aspartic acid ethyl ester, glutamic acid t-butyl ester or gluramic acid benzyl ester linked with Z at the N-terminal, and Z is hydrogen, acyl or one of the following groups:

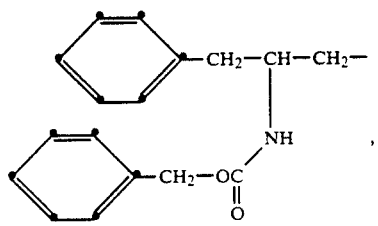

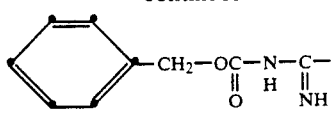

and

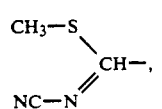

these compounds being in the form of optically pure tereomers, diastereomer mixtures, diastereomeric racemates or mixtures of diastereomeric racemates, as well as pharmaceutically usable salts of such compounds.

These compounds are useful to control or prevent high blood pressure (hypertension) and cardiac insufficiency.

This invention also comprises a pharmaceutical composition containing a compound of formula I or pharmaceutically usable salt thereof as an active ingredient and a method of treating or preventing high blood pressure or cardiac insufficiency in a warm blooded animal by the use of the compounds of formula I.

DETAILED DESCRIPTION OF THE INVENTION

The term "alkyl" used in the present description. alone or in combination with other terms, means straight-chain and branched, saturated hydrocarbon residues with 1-8, preferably 1-4, carbon atoms, such as methyl, ethyl, n-propyl, isopropyl, n-butyl, isobutyl, sec.-butyl, t-butyl, pentyl, hexyl and the like.

The term "alkoxy" means alkyl ether groups in which the term "alkyl" has the above meaning, such as methoxy, ethoxy, propoxy, isopropoxy, butoxy, isobutoxy, sec.-butoxy, t-butoxy and the like. The term "cycloalkyl" means saturated, cyclic hydrocarbon residues with 3-8. preferably 3-6, carbon atoms, such as cyclopropyl, cyclobutyl, cyclopentyl, cyclohexyl and the like.

The term "heterocycloalkyl" refers in the same manner to saturated, 3-8-membered, preferably 5- or 6-membered, cyclic hydrocarbon residues in which one or two methylene groups are replaced by one or two oxygen, sulfur or optionally alkyl-, phenylalkyl-, alkanoyl- or alkanoyloxy-substituted nitrogen atoms, such as piperidinyl, pyrazinyl, N-benzyl-pyrazinyl, morpholinyl, N-methylpiperidinyl, N-benzyl-morpholinyl and the like.

The term "aryl" means a mono- or bicyclic aromatic hydrocarbon residue with 6-14 carbon atoms which is optionally mono- or multi-substituted with alkyl, alkoxy, alkanoyloxy, amino, alkylamino, dialkylamino, alkanoylamino, hydroxy, halogen, trifluoromethyl or nitro, such as phenyl, α- or β-naphthyl, indenyl, anthryl or phenanthryl and the like.

The term "arylalkyl" means straight-chain or branched alkyl groups in which one or more hydrogen atoms are replaced by aryl groups, such as benzyl, diphenylmethyl, trityl, α- or β-naphthylmethyl, 2-phenylethyl, 3-phenyl -2-propyl, 4-phenyl-3-butyl, 2-(α- or β-naphthyl)ethyl, 3-α-naphthyl-2-propyl, 4-a-naphthyl-3-butyl and the like, whereby the aromatic residue can in each case be mono- or multi-substituted as indicated above.

The term "substituted amino" means an amino group which is mono- or di-substituted with alkyl, arylalkyl, alkanoyl, alkoxycarbonyl or arylalkoxycarbonyl, or disubstituted with $C_3$-$C_6$-alkylene which is optionally interrupted by an oxygen, sulfur or alkyl-, phenylalkyl-, alkanoyl- or alkanoyloxy-substituted nitrogen atom.

The term "acyl" relates to the acyl group of a carboxylic acid, of a half ester of carbonic acid, of an optionally N-substituted carbamic or thiocarbamic acid, of an optionally N-substituted oxalamide, of a sulfonic acid or of an optionally N-substituted amidosulfonic acid, especially those with the partial formulae $R^b$—CO—, $R^a$—O—CO—, $(R^b)(R^b)N$—CO—, $(R^b)(R^b)N$—CS—, $(R^b)(R^b)N$—CO—CO—, $R^b$—$SO_2$—, or $(R^b)(R^b)N$—$SO_2$— in which $R^a$ refers to an unsubstituted or substituted, saturated or unsaturated, aliphatic, cycloaliphatic, cycloaliphatic-aliphatic hydrocarbon residue with up to 18, preferably 10, carbon atoms, an unsubstituted or substituted aromatic, heteroaromatic, aromatic-aliphatic or heteroaromatic-aliphatic hydrocarbon residue with up to 18, preferably 10, carbon atoms, or an unsubstituted or substituted, saturated 5- or 6-membered heterocycle, and $R^b$ refers to hydrogen or has the same meaning as $R^a$. The term "acyl" also represents the monovalent residue of an amino acid, of a dipeptide or of a tripeptide attached via the carboxyl group.

By way of illustration. $R^a$ and $R^b$ can be unsubstituted or substituted alkyl, alkenyl, alkynyl, mono-. bi- or tricycloalkyl, monocycloalkenyl, bicycloalkenyl, cycloalkylalkyl, cycloalkylalkenyl or cycloalkenylalkyl. "Substituted alkyl" can be an alkyl residue in which one or more hydrogen atoms can be substituted with hydroxy, alkoxy, aryloxy, alkanoyloxy, halogen, hydroxysulphonyloxy, carboxy, alkoxycarbonyl, carbamoyl, alkylcarbamoyl, dialkylcarbamoyl, cyano, phosphono, esterified phosphono, amino or oxo, whereby the substituents are present in the 1-position of the alkyl residue only when this is attached to the carbonyl group in the partial formula $R^b$—CO—.

Examples of substituted alkyl are 2-hydroxyethyl, methoxymethyl, 2-methoxyethyl, phenoxymethyl, α- or β-naphthoxymethyl, acetoxymethyl, 2-acetoxyethyl, chloromethyl, bromomethyl, 2-chloro- or 2-bromoethyl, hydroxysulphonyloxymethyl, 2-hydroxysulphonyloxyethyl, carboxy methyl, 2-carboxyethyl, methoxycarbonylmethyl, 2-methoxy carbonylethyl, ethoxycarbonylmethyl, 2-ethoxycarbonyl, ethyl, carbamoylmethyl, 2-carbamoylethyl, methylcarbamoyl methyl, dimethylcarbamoylmethyl, cyanomethyl, 2-cyanoethyl, 2-oxopropyl, 2-oxobutyl, hydroxycarboxymethyl, 1-hydroxy-2-carboxyethyl, hydroxyethoxycarbonylethyl, hydroxymethoxycarbonylethyl, acetoxymethoxycarbonylmethyl, 1,2-dihydroxy-2-carboxyethyl, 1,2-dihydroxy-2-ethoxy-carbonylethyl, 1,2-dihydroxy-2-methoxycarbonylethyl, 1,2-diacetoxy-2-ethoxycarbonylethyl, 1,2-diacetoxy-2-methoxycarbonylethyl, 1-α-naphthoxy-3-carboxypropyl, 1-α-naphthoxy-2-ethoxycarbonylethyl, 1-α-naopthoxy-3-t-butoxycarbonylpropyl, 1-α-naphthoxy-2-benzyloxycarbonylethyl, 1-α-naphthoxy-3-carbamoylpropyl, α-naphthoxycyanomethyl, 1-α-naphthoxy-3-cyanopropyl, 1-α-naphthoxy-4-dimethylaminobutyl and 1-α-naphthoxy-3-oxobutyl.

The term "alkenyl" refers to straight-chain or branched, unsaturated hydrocarbon residues with 2-8, preferably 2-4, carbon atoms, whereby the double bond is present in the 1-position of the alkenyl residue only when this is attached to the carbonyl group in the partial formula $R^b$—CO—. Examples of such alkenyl residues are vinyl, allyl, 2-butenyl and 3-butenyl. The alkenyl residues can be substituted with the same substituents as the alkyl residues.

The term "alkynyl" refers to hydrocarbon residues with 2-8, preferably 2-4, carbon atoms which contain a triple bond, such as ethynyl, 1-propoynyl or 2-propynyl. The term "bicycloalkyl" refers to bicyclic saturated hydrocarbon residues with 5-10, preferably 6-9, carbon atoms such as bicyclo[3.1.0]hex-1-yl, bicyclo[3.1.0]hex-2- -yl, bicyclo[3.1.0]hex-3-yl, bicyclo[4.1.0]hept-1-yl, bicyclo[4.1.0]hept-4-yl, bicyclo[2.2.1]hept-2-yl, bicyclo[3.2.1]oct-2-yl, bicyclo[3.3.-0]oct-3-yl, bicyclo[3.3.1]non-9-yl, α- or β-decahydronaphthyl and the like.

The term "tricycloalkyl" refers to a tricyclic saturated hydrocarbon residue with 8-10 carbon atoms, such as 1-adamantyl.

The term "cycloalkenyl" refers to an unsaturated cyclic hydrocarbon residue with 3-8, preferably 3-6, carbon atoms, such as 1-cyclohexenyl, 1-4-cyclohexadienyl and the like.

The term "bicycloalkenyl" refers to a bicyclic unsaturated hydrocarbon residue with 5-10, preferably 7-10, carbon atoms, such as 5-norbornen-2-yl, bicyclo[2.2.-2]octen-2-yl, hexahydro-4,7-methanoind-1-en-6 yl and the like.

Examples of cycloalkylalkyl are cyclopropylmethyl, cyclobutylmethyl, cyclopentylmethyl, cyclohexylmethyl and the like. Cyclohexylvinyl, cyclohexylallyl and the like are mentioned as examples of cycloalkylalkenyl. Examples of cycloalkenylalkyl are 1-cyclohexenylmethyl, 1,4-cyclohexadienylmethyl and the like.

The above-mentioned cycloaliphatic and cycloaliphaticaliphatic residues can be substituted with the same substituents as those for alkyl.

An optionally substituted, aromatic or aromatic -aliphatic hydrocarbon residue is, for example, unsubstituted or substituted aryl, arylalkyl or arylalkenyl. Styryl, 3-phenylallyl, 2-(α-naphthyl)vinyl, 2-(β-naphthyl)vinyl and the like are examples of arylalkenyl.

In the heteroaromatic or heteroaromatic-aliphatic hydrocarbon residue, the heterocycle is mono-, bi- or tricyclic and contains one to two nitrogen atoms and/or one oxygen or sulfur atom and is linked with the group —CO—, —O—CO—, >N—CO—, >N—CS—, >N—CO—CO, —$SO_2$ or >N—$SO_2$— through one of its ring carbon atoms. Examples of such heteroaromatic hydrocarbon residues are pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benz-fused, cyclopenta-, cyclohexa- or cyclopenta-fused derivative of these residues. The heteroaromatic residue can be substituted on a nitrogen atom with alkyl, phenyl or phenylalkyl, for example, benzyl, and/or on one or more carbon atoms by alkyl, phenyl, phenylalkyl halogen, hydroxy, alkoxy, phenylalkoxy or oxo and can be partially saturated. Examples of such heteroaromatic residues are 2- or 3-pyrrolyl, phenylpyrrolyl, for example, 4- or 5-phenyl-2-pyrrolyl, 2-furyl, 2-thienyl, 2-imidazolyl, 2-, 3- or 4-pyridyl, 2-, 3- or 5-indolyl, substituted 2-indolyl, for example, 1-methyl-, 5-methyl-, 5-methoxy, 5-benzyloxy-, 5-chloro- or 4,5-dimethyl-2-indolyl, 1-benzyl-2-indolyl, 1-benzyl-3-indolyl, 4,5,6,7-tetrahydro-2-indolyl, cyclohepta[b]-5-pyrrolyl, 2-, 3- or 4-quinolyl, 4- hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, 8-carbolin-3-yl and the like.

Examples of heteroaromatic-aliphatic hydrocarbon residues are 2- or 3-pyrrolylmethyl, 2-, 3- or 4-pyridyl methyl, 2-(2-, 3- or 4-pyridyl)ethyl, 4-imidazolylmethyl, 2-(4-imidazolyl)ethyl, 2-indolylmethyl, 3-indolylmethyl, 2-(3-indolyl)ethyl, 2-quinolylmethyl and the like.

A saturated 5- or 6-membered heterocycle has at least one carbon atom, 1–3 nitrogen atoms and, optionally, one oxygen or sulfur atom as the ring member(s) and is linked with the group —CO— or —O—CO—, $\times$N—CO—, >N—CS—, >N—CO—CO—, —SO$_2$— or >N—SO$_2$— through one of its ring carbon atoms. The heterocycle can be substituted on one of its carbon atoms or on a ring nitrogen atom with an alkyl group, for example, methyl or ethyl, phenyl or phenylalkyl, for example, benzyl, or on one of its carbon atoms with hydroxy or oxo and/or can be benz-fused on two adjacent carbon atoms. Examples of such heterocycles are pyrrolidin-3-yl, 4-hydroxypyrrolidin-2-yl, 5-oxopyrrolidin-2-yl, piperidin-2-yl, piperidin- -3-yl, 1-methylpiperidin-2-yl, 1-methylpiperidin-3-yl. 1-methylpiperidin-4-yl, morpholin-2-yl, morpholin-3-yl, thiomorpholin-2-yl, thiomorpholin-3-yl, 1,4-dimethylpiperazin-2-yl, 2-indolinyl, 3-indolinyl, 1,2,3,4-tetrahydroquinol-2-, -3- or -4-yl, 1,2,3,4-tetrahydroisoquinol-1-, -3- or -4-yl, 1-oxo-1,2,3,4-tetrahydro isoquinol-3-yl and the like.

Illustratively, the residues of an amino acid attached via the carboxyl group include natural $\alpha$-amino acids having the L-configuration; homologs of such amino acids, for example, in which the amino acid side-chain is lengthened or shortened by one or two methylene groups and/or a methyl group is replaced by hydrogen; substituted aromatic $\alpha$-amino acids, for example, substituted phenylalanine or phenylglycine in which the substituent can be alkyl, for example, methyl, halogen, (i.e., fluorine, chlorine, bromine or iodine), hydroxy, alkoxy, such as methoxy, alkanoyloxy, for example, acetoxy, amino, alkylamino, such as methylamino, dialkylamino, such as dimethylamino, alkanoylamino, such as acetylamino or pivaloylamino, alkoxycarbonylamino, for example, t-butoxycarbonylamino, arylmethoxycarbonylamino, for example, benzyloxycarbonylamino, and/or nitro and can be present singly or in multiples; benz-fused phenylalanine or phenylglycine such as $\alpha$-naphthylalanine or hydrogenated phenylalanine or phenylglycine such as cyclohexylalanine or cyclohexylglycine; a 5- or 6-membered cyclic benz-fused $\alpha$-amino acid, for example, indoline-2-carboxylic acid or 1,2,3,4-tetrahydroisoquinoline-3-carboxylic acid; a natural or homologous $\alpha$-amino acid in which a carboxy group in the side-chain is present in esterified or amidated form, for example, as an alkyl ester group such as methoxycarbonyl or t-butoxycarbonyl or as a carbamoyl, alkylcarbamoyl such as methylcarbamoyl or as a dialkylcarbamoyl group such as dimethylcarbamoyl, in which an amino group of the side-chain is present in acylated form, for example, as alkanoylamino such as acetylamino or pivaloylamino, as alkoxycarbonylamino such as t-butoxycarbonylamino or as an arylmethoxycarbonylamino group such as benzyloxycarbonylamino, or in which a hydroxy group of the side-chain is present in etherified or esterified form, for example, as an alkoxy group such as methoxy, as an arylalkoxy group such as benzyloxy or as a lower alkanoyloxy group such as acetoxy, or epimers of such amino acids, that is, with the unnatural D-configuration. Examples of such amino acids are glycine, alanine, valine, norvaline, leucine, isoleucine, norleucine, serine, homoserine, threonine, methionine, cysteine proline, trans-3- and trans-4-hydroxyproline, phenylalanine, tyrosine, 4-nitrophenylalanine, 4-amino- phenylalanine, 4-chlorophenylalanine, $\beta$-phenylserine, phenylglycine, $\alpha$-naphthylalanine, cyclohexylalanine, cyclohexylglycine, tryptophan, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamic acid mono-t- butyl ester, glutamine, N-dimethylglutamine, histidine, arginine, lysine, N-t-butoxycarbonyllysine, $\delta$-hydroxylysine, ornithine, N-pivaloylornithine, $\alpha$, $\gamma$-diaminobutyric acid or $\alpha,\beta$-diaminopropionic acid and the like. The residue of the amino acid attached via the carboxyl group can be substituted N-terminally by alkyl, for example, methyl or ethyl, in order to increase the stability of the compound of formula I against enzymatic degradation.

The residue of a di- or tri-peptide attached via the carboxyl group consists of two or three of the above-mentioned amino acids.

The term "pharmaceutically usable salts" embraces salts with inorganic or organic acids, such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic and the like. Such salts can be prepared readily by these skilled in the art.

The compounds of formula I have at least three asymmetric carbon atoms and are therefore present in the form of optically pure diastereomers diastereomeric mixtures, diastereomeric racemates or mixtures of diastereomeric racemates. The present invention embraces all forms. Diastereomer mixtures, diastereomeric racemates or mixtures of diastereomeric racemates can be separated using conventional methods, for example, column chromatography, thin-layer chromatography, HPLC and the like.

Those compounds of formula I in which $R^1$ is hydrogen are preferred. $R^2$ preferably is imidazol-4 yl. Further, those compounds of formula I in which $R^3$ is cyclohexylmethyl are preferred. Also preferred are those compounds of formula I in which $R^4$ is vinyl or ethyl. Also preferred are the compounds of formula I in which A is the group (a) or (b). $R^5$ preferably is phenyl or naphthyl, particularly phenyl. Preferred for $R^6$ are alkylcarbonylalkyl, cycloalkylcarbonylalkyl, heterocycloalkylcarbonylalkyl, aminocarbonylalkyl or substituted aminocarbonylalkyl, preferably $C_1$–$C_4$-alkylcarbonylmethyl, $C_5$–$C_6$-cycloalkylcarbonylmethyl, N-t-butoxycarbonylpyrrolidinylcarbonylmethyl or aminocarbonylalkyl, which is disubstituted with $C_1$–$C_4$-alkyl or $C_4$–$C_5$-alkylene optionally interrupted by an oxygen atom or which is monosubstituted with aminoalkyl mono- or disubstituted with alkoxycarbonylalkyl or alkoxycarbonyl.

Furthermore, there are preferred the compounds of formula I in which Y represents the bivalent residue of phenylalanine, cyclohexylalanine, 4-chlorophenylalanine or $\alpha$-naphthylalanine, particularly phenylalanine, linked with Z at the N-terminal. Z preferably is acyl, particularly the residue, linked with Y at the C-terminal, of a N- and/or $\alpha$-methylated natural amino acid having the L-configuration or an epimer of such an amino acid having the D-configuration or of a dipeptide from two of the above-described amino acids or the group $R^b$—CO— or $R^a$—O—CO— in which $R^a$ is an optionally substituted, saturated or unsaturated aliphatic, cyclo-aliphatic, cycloaliphatic-aliphatic hydrocarbon residue with up to 18 carbon atoms, an optionally substituted aromatic, heteraromatic, aromatic-aliphatic or heteroaromatic-aliphatic hydrocarbon residue with up to 18 carbon atoms or an optionally substituted, saturated 5- or 6-membered heterocycle and $R^b$ is hydrogen or has the significance $R^a$, particularly a residue, linked with Y at the C-terminal, of proline, prolylproline or histidinylproline, whereby the amino group in each case is substituted with t-butoxycarbonyl, benzoxycarbonyl, isovaleryl or the group $R^b$—CO— in which $R^b$ is a heteroaromatic-aliphatic hydrocarbon residue with up to 10 carbon atoms or a saturated 5- or 6-membered heterocycle.

From the above, it can be seen that there are particularly preferred those compounds in which $R^1$ is hydrogen, R is imidazol-4-yl, $R^3$ is cyclohexylmethyl, $R^4$ is vinyl or ethyl, $R^5$ is phenyl, and $R^6$ is $C_1$-$C_4$-alkyl-carbonylmethyl, $C_5$-$C_6$-cycloalkylcarbonylmethyl, N-t-butoxycarbonylpyrrolidinylcarbonylmethyl or aminocarbonylalkyl, which is disubstituted with $C_1$-$C_4$-alkyl or $C_4$-$C_5$-alkylene optionally interrupted by an oxygen atom or which is mono-substituted with aminoalkyl mono- or di-substituted with alkoxycarbonylalkyl or alkoxycarbonyl, or those compounds in which Y is the bivalent residue of phenylalanine linked with Z at the N-terminal and Z is the residue of proline, prolylproline or histidinylproline linked with Y at the C-terminal, in which the amino group in each case is substituted with t-butoxycarbonyl, benzoxycarbonyl, isovaleryl or the group $R^b$—CO— in which $R^b$ is a heteroaromatic-aliphatic hydrocarbon residue with up to 10 carbon atoms or a saturated 5- or 6-membered heterocycle.

Especially preferred compounds of formula I are the following:

t-butyl (R)-2-[[(S)-α-[[(S)-1-[(1S, 2S,4S)-1-(cyclohexylmethyl)-2-hydroxy-4-isopropylhexyl]-2-imidazol-4-ylethyl]carbamoyl]phenethyl]carbamoyl]-1-pyrrolidine carboxylate;

(2S,3S,5S)-2-(Boc-D-Pro-Phe-His-NH)-1-cyclohexyl-5-isopropyl-6-hepten-3-ol;

N-(S)-[(1S,2S.4S)-1-(cyclohexylmethyl)-2-hydroxy.4-isopropyl-5-hexenyl]-α-[(S)-α-3-methylbutyramido]-imidazole-4-propionamide;

t-butyl [(S)-α-[[(S)-1-[[(1S,2S,4S)-1-cyclohexylmethyl-2-hydroxy-4-isopropyl-5-hexenyl]carbamoyl]-2-imidazol-4-ylethyl]carbamoyl]phenethyl]carbamate;

t-butyl [(S)-α-[[(S)-1-[[(1S,2S,4S)-1-cyclohexylmethyl-2-hydroxy-4-isopropylhexyl]carbamoyl]-2-imidazol-4-ylethyl]carbamoyl]phenethyl]carbamate;

t-butyl (S)-2-[[(R)-α-[[(S)-1-[[(1S,2S,4S)-1-(cyclohexylmethyl)-2-hydroxy-4-isopropylhexyl]carbamoyl]-2-imidazol-4-ylethyl]carbamoyl]phenethyl]acetyl]-1-pyrrolidinecarboxylate;

(S)-N-[(1S,2S,4S)-1-(cyclohexylmethyl)-2-hydroxy-4-isopropylhexyl]-α-[[[[(R)-α-2-hydroxy-1-(hydroxymethyl)-1-methylethyl]carbamoyl]methyl]hydrocinnamamido]imidazole-4-propionamide;

N-(S)-1-[[(1S,2S,4S)-1-cyclohexylmethyl)-2-hydroxy-4-isopropylhexyl]carbamoyl]-2-imidazol-4-ylethyl]-γ-oxo-α-(1-naphthylmethyl)-4-morpholinebutyramide;

t-butoxycarbonyl [2-[(R and S)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenyl butyramido]ethyl]glycine t-butyl ester;

(S)-N-[(1S,2S,4S)-1-(cyclohexylmethyl)-2-hydroxy-4-isopropyl-5-hexenyl]-α-[(R)-α-[[[2-hydroxy-1-(hydroxymethyl)-1-methylethyl]carbamoyl]methyl]hydrocinnamamido]imidazole-4-propionamide;

(S)-α-[(R)-2-benzyl-5,5-dimethyl-4-oxohexanamido]-N-[(1S,2S,4S)-1-(cyclohexylmethyl-2-hydroxy-4-isopropyl-5-hexenyl]imidazole-4-propionamide;

(S)-N-[(1S,2S,4S)-1-(cyclohexylmethyl)-2-hydroxy-4-isopropyl-5-hexenyl]-α-2-[N-(morpholinocarbamoyl) 3-phenyl-L-alanyl]amino]imidazole-4-propionamide;

(S)-α-[(R)-α-(carbamoylmethyl)hydrocinnamamido]-N-[(1S,2S,4S)-1-(cyclohexylmethyl)-2-hydroxy-4-isopropyl-5-hexenyl]imidazole-4-propionamide;

(S)-N-[(1S,2S,4S)-1-(cyclohexylmethyl)-2-hydroxy-4-isopropyl-5-hexenyl]-α-[(R)-α-[(dimethylcarbamoyl)methyl]hydrocinnamamido]imidazole-4-propionamide;

(S)-N-[(1S,2S,4S)-1-(cyclohexylmethyl)-2-hydroxy.4-isopropyl-5-hexenyl]-α-[(RS)-α-[(cyclopentylcarbonyl)methyl]hydrocinnamamido]imidazole-4-propionamide;

(S)-N-[(1S,2S,4S)-1-(cyclohexylmethyl)-2-hydroxy-4-isopropylhexyl]-α-[(RS)-α-[(cyclopenrylcarbonyl)methyl]hydrocinnamamido]imidazole-4-propionamide, and (2S,5S)-2-(Boc-D-Pro-Pro-Phe-His-NH)-1-cyclohexyl-5-isopropyl-6-hepten-3-ol.

The compounds of formula I in the form of optically pure diastereomers, diastereomer mixtures, diastereomeric racemates or mixtures of diastereomeric racemates as well as pharmaceutically usable salts thereof can be prepared by a) reacting a compound of the formula

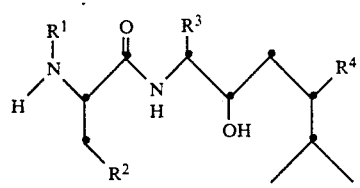

II in which $R^1$, $R^2$, $R^3$ and $R^4$ have the meanings given above, with an acylating agent to yield the group

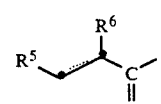

(a)

or

—Y—Z (b)

in which $R^5$, $R^6$, Y, Z and the dotted line have the meanings given above, b) reacting a compound of the formula

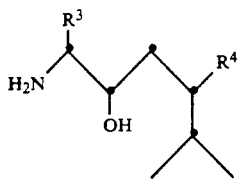

in which $R^3$ and $R^4$ have the meanings given above, with a compound of the formula

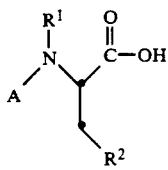

wherein $R^1$, $R^2$ and A have the meanings given above, or an activated derivative thereof, or c) for the preparation of a compound of formula I in which $R^4$ is ethyl and the remaining symbols have the meanings given above, hydrogenating a compound of formula I in which $R^4$ is vinyl and the remaining symbols have the meanings given above, or d) for the preparation of a compound of formula I in which $R^4$ means 1,2-dihydroxyethyl and the remaining symbols have the meanings given above, oxidizing a compound of formula I in which $R^4$ means vinyl and the remaining symbols have the meanings given above, or e) for the preparation of a compound of formula I in which A contains a free amino group, cleaving off the N-protecting group from a corresponding compound of formula I in which A contains a N-protected amino group, or f) if desired, separating a mixture of diastereomeric racemates into the diastereomeric racemates or optically pure diastereomers, or g) if desired, separating a diastereomer mixture into the optically pure diastereomers, or h) if desired, converting a compound obtained into a pharmaceutically usable salt.

The acylation of a compound of formula II is effected according to known methods. Especially suitable acylating agents are activated acid derivatives such as esters, mixed esters, acid halides and acid anhydrides or mixed anhydrides. The reaction is carried out in an organic solvent or solvent mixture which is inert under the reaction conditions, at a temperature between about 0° C. and room temperature. As solvents there can be used aromatic hydrocarbons such as benzene, toluene or xylene, chlorinated hydrocarbons such as methylene chloride or chloroform, and ethers such as diethyl ether, tetrahydrofuran or dioxan, and the like. Where the acylating agent is a peptide, the reaction is effected under reaction conditions which are usual in peptide chemistry, preferably in the presence of a condensation agent such as HBTU (O-benzotriazolyl-N,N,N',N'-tetramethyluronium hexafluorophosphate), BOP (benzotriazol-1-yloxy bis-(dimethylamino)phosphonium hexafluorophosphate), HOBT (N-hydroxybenzotriazole), DBU (1,8-diazabicyclo[5.4.0]undec-7-ene), DCC (dicyclohexylcarbodiimide). EDC (N-ethyl-N' (3-dimethylaminopropyl)carbodiimide hydrochloride), Hünig base (ethyldiisopropylamine), or the like. The reaction is conveniently carried out in an organic solvent or solvent mixture which is inert under the reaction conditions, at a temperature between about 0° and 50° C. preferably at about room temperature. As solvents there can be used, especially, dimethylformamide, methylene chloride, acetonitrile, tetrahydrofuran, and the like.

The reaction of a compound of formula III with a compound of formula IV is also effected according to methods which are known per se in peptide chemistry, that is, under the same conditions as given above for the reaction of a compound of formula II with a peptide. Examples of suitable activated derivatives of a compound of formula IV are acid halides, acid anhydrides, mixed anhydrides, esters, mixed esters, and the like.

The hydrogenation of a compound of formula I in which $R^4$ is vinyl is also effected according to known methods, in an organic solvent or solvent mixture which is inert under the reaction conditions, at a temperature between about room temperature and 50° C., preferably at room temperature, in the presence of a noble metal catalyst such as platinum or palladium, preferably palladium. Suitable solvents include, especially, alcohols such as methanol or ethanol, and the like.

The oxidation of a compound of formula I in which $R^4$ is vinyl is also effected according to methods known per se in an organic solvent or solvent mixture which is inert under the reaction conditions, at a temperature between about room temperature and the boiling point of the solvent or solvent mixture, preferably at about room temperature. Osmium tetroxide is an especially suitable oxidizing agent. The preferred solvent is pyridine.

The cleavage of the N-protecting group in accordance with process variant (e) is also effected according to methods known in an organic solvent or solvent mixture which is inert under the reaction conditions, at a temperature between about 0° C. and room temperature, with an acid such as hydrochloric acid, trifluoroacetic acid, and the like. Suitable solvents are ethers such as tetrahydrofuran or dioxane, alcohols such as methanol, or chlorinated hydrocarbons such as methylene chloride, and the like.

The starting materials of formula II are part of the present invention. These compounds can be prepared by reacting a compound of formula III with optionally N-methylated histidine, norleucine or norvaline. This reaction is also effected according to methods which are known in peptide chemistry, that is, under the reaction conditions described above for the reaction of a compound of formula II with a peptide.

The starting materials of formula III are also novel and are an object of the present invention. They can be prepared, for example, by reacting an aldehyde of the formula

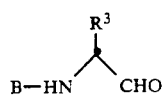

wherein B is an amino protecting group, preferably t-butoxycarbonyl or benzyloxycarbonyl, and $R^3$ has the meaning given above, with a compound of the formula

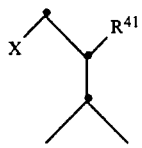

VI wherein X is chlorine, bromine or iodine, preferably bromine, and $R^{41}$ is phenyl, furyl or vinyl, in a Grignard reaction. This reaction is also effected according to known methods, for example, in a solvent which is inert under the reaction conditions, such as an ether, at a temperature between about 0° and 50° C., preferably at room temperature. Subsequently, the amino protecting group B is cleaved off from the compound, for example, with hydrochloric acid in dioxane at room temperature. Where a compound of formula III in which $R^4$ is ethyl or 1,2-dihydroxyethyl is desired, the product of the Grignard reaction is hydrogenated or oxidized according to known methods prior to the cleavage of the amino protecting group B under the reaction conditions given for process variant (c). Suitable oxidizing agents are osmium tetroxide, potassium permanganate, ruthenium tetroxide, and the like. The reaction is carried out in an organic solvent or solvent mixture which is inert under the reaction conditions, at a temperature between about room temperature and 50° C. Suitable solvents are pyridine. aromatic hydrocarbons such as benzene, and the like.

The compounds of formula V are known or can be obtained by analogy to the preparation of known compounds.

The compound of formula VI in which $R^{41}$ is vinyl is known. The compounds of formula VI in which $R^{41}$ is phenyl or furyl are novel and constitute an aspect of the present invention.

A process for the preparation of a compound of formula III in which $R^4$ is phenyl, furyl or vinyl is set forth of each of Schemes I-III hereinafter. The preparation of the novel compounds of formula VI in which $R^{41}$ is phenyl or furyl can also be carried out from Schemes II and III. Precise reaction conditions are given in the working examples.

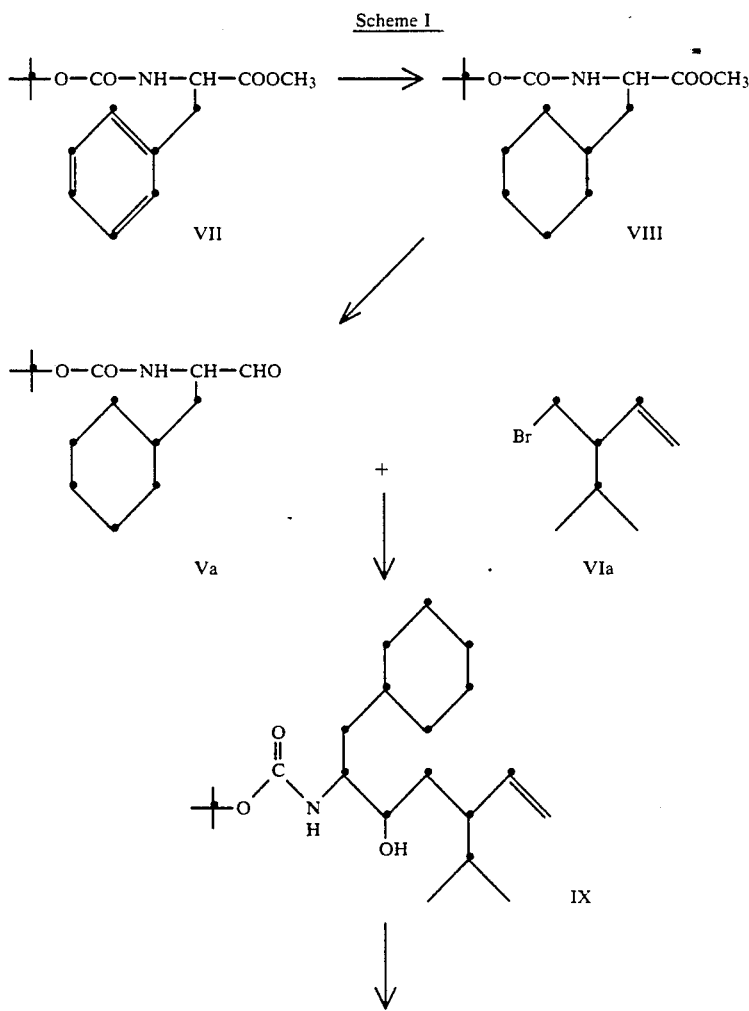

Scheme I

Scheme I

IIIa

Scheme II

X → XI

XIII ← XII

VIb + Vb

-continued
Scheme II

XIV

↓

IIIb

Scheme III

XV → XVI

↓

XVIII (rac) ← XVII

↓

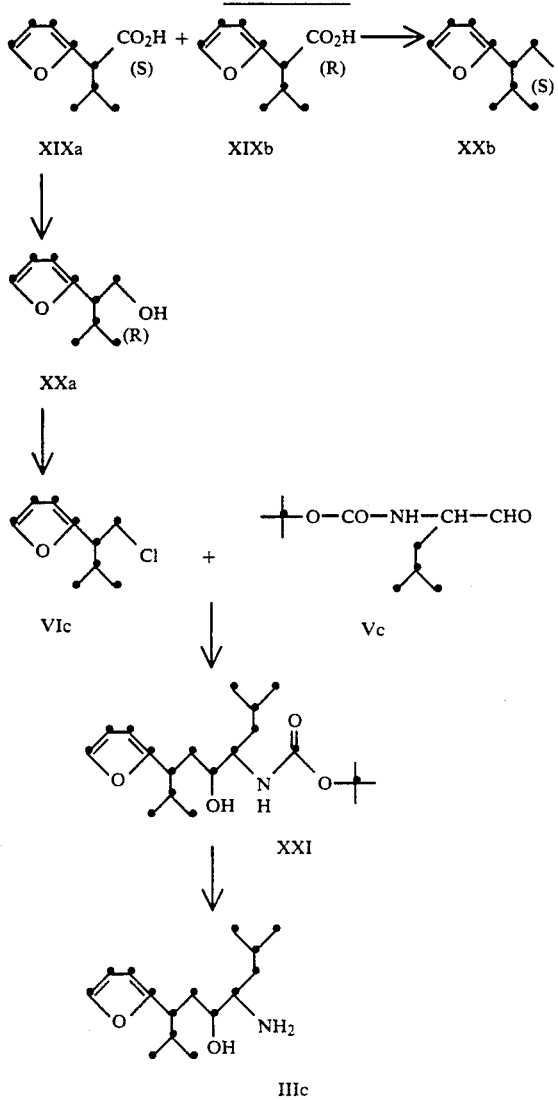

The compounds of formula I and their pharmaceutically usable salts have an inhibitory activity on the natural enzyme renin. The latter passes from the kidneys into the blood and brings about the cleavage of angiotensinogen, with the formation of the decapeptide angiotensin I, which is then cleaved in the lungs, the kidneys and other organs to the octapeptide angiotensin II. Angiotensin II increases blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II, itself, or to the heptapeptide angiotensin III which is formed therefrom as a cleavage product. Inhibition of the enzymatic activity of renin brings about a decrease in the formation of angiotensin I and as a consequence the formation of a smaller amount of angiotensin II. The reduced concentration of this active peptide hormone is the actual reason for the blood pressure-lowering activity of renin inhibitors.

The activity of renin inhibitors is demonstrated by means of the following in vitro test:

In Vitro Test With Pure Human Renin

The test is carried out in Eppendorf test tubes. The incubation mixture consists of (1) 100 μl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2–3 ng of angiotensin I/ml/hr.; (2) 145 μl of buffer A; (3) 30 μl of 10 μM human tetradecapeptide renin substrate (hTD) in 10 mM hydrochloric acid; (4) 15 μl of dimethyl sulfoxide with or without inhibitor and (5) 10 μl of a 0.03 molar solution of hydroxyquinoline sulfate in water.

The samples are incubated for 3 hours at 37° C. or 4° C. in triplicate. 2×100 μl samples per experimental test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I in determined by the difference between the experiment at 37° C. and that at 4° C.

The following controls are carried out:

(a) Incubation of hTD samples without renin and without inhibitor at 37° C. and 4° C. The difference between these two values gives the base value of angiotensin I production.

(b) Incubation of hTD samples with renin, but without inhibitor at 37° C. and 4° C. The difference between these values gives the maximal value of angiotensin I production.

In each sample, the base value of the angiotensin I production is subtracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ values in μMol/lt. |
| --- | --- |
| A | 0.0035 |
| B | 0.0003 |
| C | 0.0090 |
| D | 0.0075 |
| E | 0.0079 |
| F | 0.0040 |
| G | 0.0150 |
| H | 0.0041 |
| I | 0.0460 |
| K | 0.0170 |
| L | 0.0070 |
| M | 0.0210 |
| N | 0.1400 |
| O | 0.0120 |
| P | 0.0460 |
| Q | 0.0680 |
| R | 0.0017 |

A = t-Butyl (R)-2-[[(S)-α-[[(S)-1-[(1S,2S,4S)-1-cyclohexylmethyl-2-hydroxy-4-isopropylhexyl]-2-imidazol-4-yl-ethyl]carbamoyl]phenethyl]carbamoyl]-1-pyrrolidine-carboxylate;

B = (2S,3S,5S)-2-(Boc—D—Pro—Phe—His—NH)-1-cyclohexyl-5-isopropyl-6-hepten-3-ol;

C = N-(S)-[(1S,2S,4S)-1-(cyclohexylmethyl-2-hydroxy-4-isopropyl-5-hexenyl]-α-[(S)-α-3-methylbutyramido]-imidazole-4-propionamide;

TABLE-continued

D = t-butyl [(S)-α-[[(S)-1-[[(1S,2S,4S)-1-cyclohexylmethyl-2-hydroxy-4-isopropyl-5-hexenyl]carbamoyl]-2-imidazol-4-yl-ethyl]carbamoyl]phenethyl]carbamate;
E = t-butyl [(S)-α-[[(S)-1-[[(1S,2S,4S)-1-cyclohexylmethyl-2-hydroxy-4-isopropylhexyl]carbamoyl]-2-imidazol-4-ylethyl]carbamoyl]phenethyl]carbamate;
F = t-butyl (S)-2-[[(R)-α-[[(S)-1-[[(1S,2S,4S)-1-(cyclohexylmethyl)-2-hydroxy-4-isopropylhexyl]carbamoyl]-2-imidazol-4-ylethyl]carbamoyl]phenethyl]acetyl]-1-pyrrolidinecarboxylate;
G = (S)-N-[(1S,2S,4S)-1-(cyclohexylmethyl)-2-hydroxy-4-isopropylhexyl]-α-[[[[(R)-α-2-hydroxy-1-(hydroxymethyl)-1-methylethyl]carbamoyl]methyl]hydrocinnamamido]imidazole-4-propionamide;
H = N-(S)-1-[[(1S,2S,4S)-1-(cyclohexylmethyl)-2-hydroxy-4-isopropylhexyl]carbamoyl]-2-imidazol-4-ylethyl]-γ-oxo-α-(1-naphthylmethyl)-4-morpholinebutyramide;
I = t-butyloxycarbonyl [2-[(R and S)-3-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]-4-phenylbutyramido] ethyl]glycine t-butyl ester;
K = (S)-N-[(1S,2S,4S)-1-(cyclohexylmethyl)-2-hydroxy-4-isopropyl-5-hexenyl]-α-[(R)-α-[[[2-hydroxy-1-(hydroxymethyl)-1-methylethyl]carbamoyl]methyl]hydrocinnamamido]imidazole-4-propionamide;
L = (S)-α-[(R)-2-benzyl-5,5-dimethyl-4-oxohexanamido]-N-[(1S,2S,4S)-1-(cyclohexylmethyl-2-hydroxy-4-isopropyl-5-hexenyl]imidazole-4-propionamide;
M = (S)-N-[(1S,2S,4S)-1-(cyclohexylmethyl)-2-hydroxy-4-isopropyl-5-hexenyl]-α-2-[N-(morpholinocarbamoyl)-3-phenyl-L-alanyl]amino]imidazole-4-propionamide;
N = (S)-α-[(R)-α-(carbamoylmethyl)hydrocinnamamido]-N-[(1S,2S,4S)-1-(cyclohexylmethyl)-2-hydroxy-4-isopropyl-5-hexenyl]imidazole-4-propionamide;
O = (S)-N-[(1S,2S,4S)-1-(cyclohexylmethyl)-2-hydroxy-4-isopropyl-5-hexenyl]-α-[(R)-α-[(dimethylcarbamoyl)-methyl]hydrocinnamamido]imidazole-4-propionamide;
P = (S)-N-[(1S,2S,4S)-1-(cyclohexylmethyl)-2-hydroxy-4-isopropyl-5-hexenyl]-α-[(RS)-α-[(cyclopentyl-carbonyl)methyl]hydrocinnamamido]imidazole-4-propionamide;
Q = (S)-N-[(1S,2S,4S)-1-(cyclohexylmethyl)-2-hydroxy-4-isopropylhexyl]-α-[(RS)-α-(cyclopentylcarbonyl)methyl]hydrocinnamamido]imidazole-4-propionamide and
R = (2S,5S)-2-(Boc—D—Pro—Pro—Phe—His—NH)-1-cyclohexyl-5-isopropyl-6-hepten-3-ol.

The compounds of formula I as well as their pharmaceutically usable salts can be used in the form of pharmaceutical preparations. The pharmaceutical preparations can be administered enterally such as orally, for example, in the form of tablets, coated tablets, dragees, hard and soft gelatin capsules, solutions, emulsions or suspensions, nasally, for example, in the form of nasal sprays, or rectally, for example, in the form of suppositories. However, the administration can also be effected parenterally such as intramuscularly or intravenously, for example, in the form of injection solutions.

For the preparation of tablets, coated tablets, dragees and hard gelatin capsules, the compounds of formula I as well as their pharmaceutically acceptable salts can be processed with pharmaceutically inert, inorganic or organic excipients. Lactose, maize starch or derivatives thereof, talc, stearic acid or its salts, and so forth, can be used as such excipients for tablets, dragees and hard gelatin capsules.

Suitable excipients for soft gelatin capsules are, for example, vegetable oils, waxes, fats, semi-solid and liquid polyols, and so forth.

Suitable excipients for the preparation of solutions and syrups are, for example, water, polyols, saccharose, invert sugar, glucose, and so forth.

Suitable excipients for injection solutions are, for example, water, alcohols, polyols, glycerol, vegetable oils, and so forth.

Suitable excipients for suppositories are, for example, natural or hardened oils, waxes, fats, semi-liquid or liquid polyols, and so forth.

Moreover, the pharmaceutical preparations can contain preserving agents, solubilizers, viscosity-increasing substances, stabilizing agents, wetting agents, emulsifying agents, sweetening agents, coloring agents, flavoring agents, salts for varying the osmotic pressure, buffers, coating agents or antioxidants. They can also contain still other therapeutically useful substances.

In accordance with this invention, the compounds of formula I as well as their pharmaceutically acceptable salts can be used in the control or prevention of high blood pressure and cardiac insufficiency. The dosage can vary within wide limits and will, of course, be fitted to the individual requirements in each particular case. In general, in the case of oral administration there should suffice a daily dosage of about 3 mg to about 3 g, preferably about 10 mg to about 1 g, for example, approximately 300 mg per person, divided in preferably 1-3 unit doses, which can be of the same amount. However, the upper limit just given can also be exceeded when this is found to be indicated. Usually, children receive half of the dosage of adults.

The following Examples are intended to illustrate the present invention, but are not intended to be limiting in any manner. All temperatures are given in degrees Celsius. The following abbreviations for amino acids and amino acid derivatives are used:

H-His-OH = L-histidine
H-Phe-OH = L-phenylalanine
H-Phe$^R$His-OH = N-[(S)-2-amino-3-phenylpropyl-]—L-histidine
H-Pro-OH = L-proline
H-Ser-OH = L-serine
H-Tyr-OH = L-tyrosine Further abbreviations:

Boc = t-butoxycarbonyl
Bom = benzyloxymethyl
IVA = isovaleryl
OBz = benzyloxy
OMe = methoxy
Pip = piperidinyl
Fmoc = 9-fluorenylmethoxycarbonyl
t-Bu = t-butyl

EXAMPLE 1

A mixture of 313 mg 1.18 mmol) of t-butoxycarbonyl-L-phenylalanine. 460 mg (1.18 mmol) of (S)-α-amino-N-[(1S,2S,4S)-1-(cyclohexylmethyl)-2-hydroxy-4-isopropyl-5-hexenyl]imidazole-4-propionamide, 0.15 ml (1.18 mmol) of 4-ethylmorpholine, 320 mg (2.36 mmol) of HOBT and 292 mg (1.42 mmol) of DCC in 20 ml of dimethylformamide was stirred at room temperature overnight. Thereafter, the separated precipitate was filtered off and the solvent was evaporated in a high vacuum. The residue was dissolved in ethyl acetate and then washed in succession with 2N sodium bicarbonate solution, saturated ammonium chloride solution, again with 2N sodium bicarbonate solution and again with saturated ammonium chloride solution. After drying the organic solution over sodium sulfate, the solvent was evaporated under reduced pressure and, for purification, the residue (870 mg) was chromatographed on 30 g of silica gel using a 20:1:0.1 mixture of methylene chloride, methanol and ammonia as the eluting agent. Crystallization of the thus-obtained crude product from methylene chloride/ether yielded 410 mg of t-butyl [(S)-α-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]phenethyl]carbamate, melting point 161°.

The (S)-α-amino-N-[(1S,2S,4S)-1-(cyclohexylmethyl)-2-hydroxy-4-isopropyl-5-hexenyl]imidazole-4-propionamide used as the starting material was prepared as follows:

315.3 g (1.28 mmol) of t-butoxycarbonyl-L-phenylalanine methyl ester were hydrogenated according to the method of J. Boger et al. in J. Med. Chem., 28, 1779 (1985) in the presence of 5% rhodium on aluminum oxide at room temperature and 440 kPa, to obtain 315.3 g of 2-t-butoxycarbonylamino-3-cyclohexylpropionic acid methyl ester as an oil, which was used directly in the next step.

750 ml (750 mmol) of a 20% solution of diisobutylaluminum hydride in hexane were added dropwise at −75° C. in the course of 90 minutes to 85.61 g (300 mmol) of 2-t-butoxycarbonylamino-3-cyclohexylpropionic acid methyl ester in 1.2 l of toluene. After completion of the addition, the reaction mixture was stirred at −75° for a further 10 minutes. There were subsequently added dropwise in each case within 25 minutes, at a temperature of −75° to −70°, first 70 ml of methanol and then 840 ml of saturated potassium sodium tartrate solution. The milky reaction solution, warmed slowly to room temperature, was thereafter extracted with ether and the extracts were dried and evaporated, whereby 82 g of 2-t-butoxycarbonylamino-3-cyclohexylpropyl aldehyde was obtained as an oil, which was used in the next step without further purification.

A solution of 179.7 g (1.01 mol) of 4-bromo-3-isopropyl-1-butene (which was prepared according to the method of R. G. Helmquist in Tetrahedron Letters, 2533 (1982)) in 900 ml of ether was added dropwise within 2.5 hours to 24.65 g of magnesium shavings in 300 ml of ether, in an argon atmosphere, and at a temperature between 30° and the reflux temperature of the solvent. After completion of the addition, the reaction mixture was heated to reflux for 3.5 hours. To the reaction mixture, cooled to −60° C. was added dropwise within 75 minutes a solution of 82 g of 2-t-butoxycarbonylamino-3-cyclohexylpropyl aldehyde in 900 ml of ether, with the temperature at to −60° to −70°. After completion of the addition, the cooling bath was removed and the reaction mixture was stirred at room temperature for 21 hours under argon. The mixture was then cooled to 5° and 225 ml of a saturated ammonium chloride solution was added cautiously while stirring, upon which the temperature rose to 20°. The two phases were separated and the organic phase was dried over sodium sulfate and evaporated with 127.5 g of a yellow oil being obtained. Chromatographic separation of this oil on 2.5 kg of silica gel with methylene chloride which contained 2.5% ether as the eluting agent yielded 33.9 g of (αS,βS)-β-t-butoxycarbonylamino-α-[(S)-2-isopropyl-3-butenyl]cyclohexanepropanol, 13.62 g of (αS,βS)-β-t-butoxycarbonylamino-α-[(R)-2-isopropyl-3-butenyl]cyclohexanepropanol, as well as 35.5 g of a mixture of both of the above-named diastereomers in the form of oils, MS: 354 (M+H)+.

1.0 g (2.83 mmol) of (αS,βS)-β-t-butoxycarbonyl-amino-α-[(S)-2-isopropyl-3-butenyl]cyclohexanepropanol was dissolved in 20 ml of 2.2N hydrogen chloride in dioxane and stirred at room temperature for 2 hours. Thereafter, the reaction mixture was evaporated and treated twice in succession with toluene and then again evaporated to dryness. There was obtained thin-layer chromatographically pure (αS,βS)-β-amino-α-[(S)-2-isopropyl-3-butenyl]cyclohexanepropanol in the form of the hydrochloride, which was used directly in the next step.

1.7 g (2.83 mmol) of N-α-N-im-Bis-Fmoc-L-histidine and 0.82 g (2.83 mmol) of (αS,βS)-β-amino-α-[(S)-2-isopropyl-3-butenyl]cyclohexanepropanol hydrochloride in 20 ml of dimethylformamide were treated with 0.36 ml of 4-ethylmorpholine and 0.77 g of HOBT and cooled in an ice bath. 0.7 g of DCC was added to the cooled solution and the mixture was stirred overnight under an argon atmosphere without removing the ice bath, the reaction mixture being allowed to warm slowly to room temperature. Thereafter, the separated precipitate was filtered off and the filtrate was evaporated in a high vacuum. The residue was poured onto ice and 70 ml of a 2N sodium bicarbonate solution and extracted three times with 150 ml of ethyl acetate each time. The organic extracts were washed once with ice and 70 ml of saturated ammonium chloride solution, once with 70 ml of ice and 2N sodium bicarbonate solution, and once with 70 ml of saturated sodium chloride solution, then dried over magnesium sulphate and evaporated. The crude product (2.31 g) obtained in this manner was stirred at room temperature for 3 hours in 3 ml of piperidine and 75 ml of methylene chloride. The mixture was then evaporated at about 30° and the residue was triturated with 60 ml of hexane, to obtained 1.44 g of a solid which was chromatographed over 120 g of silica gel with a 12:1:0.1 mixture of methylene chloride, methanol and ammonia. Two-fold recrystallization of the crude product obtained from hexane yielded 580 mg of thin-layer chromatographically pure (S)-α-amino-N-[(1S,2S,4S)-1-(cyclohexylmethyl)-2-hydroxy-4-isopropyl-5-hexenyl]-imidazole-4-propionamide as crystals, melting point 73°.

EXAMPLE 2

130 mg (0.24 mmol) of t-butyl [(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-phenethyl] carbamate were dissolved in 30 ml of methanol and hydrogenated at room temperature for 1.5 hours in the presence of 65 mg of palladium-on-carbon (5%). After completion of the hydrogen uptake, the catalyst was filtered off and the filtrate was evaporated. Crystallization of the residue from ether/hexane yielded 110 mg of t-butyl [(S)-α-[[(S)-1-[[(1S,2S,4S)-1-(cyclohexylmethyl)-2-hydroxy-4-isopropylhexyl]carbamoyl]-2-imidazol-4-ylethyl]-carbamoyl]phenethyl] carbamate as crystals, melting point 101°.

EXAMPLE 3

A mixture of 83 mg (0.345 mmol) of dibenzylacetic acid, 90 mg (0.23 mmol) of (S)-α-amino-N-[(1S,2S,4S)-1-(cyclohexylmethyl)-2 -hydroxy-4-isopropyl-5-hexenyl]-imidazole-4-propionamide. 0.045 ml (0.345 mmol) of 4-ethylmorpholine, 93 mg (0.69 mmol) of HOBT and 85 mg (0.41 mmol) of DCC in 15 ml of dimethylformamide was stirred at room temperature overnight. Thereafter, the separated precipitate was filtered off and the filtrate was evaporated to dryness. The residue was then dissolved in ethyl acetate and the solution was washed in succession with 2N sodium bicarbonate solution, saturated ammonium chloride solution, again with 2N sodium bicarbonate solution and again with saturated ammonium chloride solution, dried over sodium sulfate and evaporated. The residue was chromatographed on 30 g of silica gel with a 14:1:0.1 mixture of methylene chloride, methanol and ammonia. Crystallization of the residue from methylene chloride/methanol/hexane yielded 60 mg of (S)-N-[(1S,2S,4S)-1-(cyclohexylmethyl)-2-hydroxy-4-isopropyl-5-hexenyl]-α-(2,2-dibenzylacetamido)imidazole-4-propionamide, melting point 98°.

EXAMPLE 4

A mixture of 880 mg (2.5 mmol) of (S)-α-amino-N-[(1S,2S,4S)-2-hydroxy-1-isobutyl-4-isopropyl-5-hexenyl]-imidazole-4-propionamide. 1.99 g (7.5 mmol) of t-butoxycarbonyl-L-phenylalanine. 1.05 ml (7.5 mmol) of triethylamine and 3.32 g (7.5 mmol) of BOP in 100 ml of acetonitrile was stirred at room temperature for 6 days. Thereafter, the solvent was evaporated and the residue was dissolved in ethyl acetate and washed in succession with 2N sodium bicarbonate solution, saturated ammonium chloride solution, again with 2N sodium bicarbonate solution and again with saturated ammonium chloride solution. The organic solution was dried over sodium sulfate and evaporated and the residue was triturated twice with hexane. The residue was chromatographed on 100 g of silica gel with a 98:2 mixture of chloroform and methanol. Recrystallization of the thus-obtained crude product from methylene chloride and hexane yielded 400 mg of t-butyl [(S)-α-[[(S)-1-[[(1S,2S,4S)-2-hydroxy-1-isobutyl-4 -isopropyl-5-hexenyl]carbamoyl]-2-imidazol-4-ylethyl]carbamoyl]phenethyl]carbamate as a white powder, melting point 82°.

The (S)-α-amino-N-[(1S,2S,4S)-2-hydroxy-1-isobutyl-4-isopropyl-5-hexenyl]imidazole-4-propionamide used as the starting material was prepared as follows:

t-Butoxycarbonyl-L-leucine methyl ester was reduced with diisobutylaluminium hydride in an analogous manner to that described in Example 1 to give 2-t-butoxycarbonylamino-4-methyl-valeraldehyde, which was used directly in the next step without further purification.

A solution of 142.3 g (691 mmol) of 4-bromo-3-isopropyl-1-butene in 600 ml of ether was added dropwise within 75 minutes to 16.8 g of magnesium shavings in 980 ml of ether under argon and at room temperature. After completion of the addition, the reaction mixture was heated to reflux for 3.25 hours and thereafter cooled to −60°. There was added dropwise within 75 minutes a solution of 50.1 g (203.8 mmol) of 2-t-butoxycarbonylamino-4-methyl-valeraldehyde in 600 ml of ether. After completion of the addition, the cooling bath was removed and the reaction mixture was stirred at room temperature for 17 hours. The mixture was then cooled to 5° and 150 ml of a saturated ammonium chloride solution were added dropwise while stirring, upon which the temperature rose to 20°. After a working-up analogous to that described in Example 1, there was obtained 88.4 g of a yellow oil, which was chromatographed on 2.5 kg of silica gel with a 98:2 mixture of methylene chloride and ether. After repeated chromatography of the mixed fractions under the same conditions, there was obtained a total of 30.2 g of pure, thin-layer chromatographically uniform (4S)-t-butoxy-carbonylamino-(5S)-hydroxy-(7S) -isopropyl-2-methyl-8-nonene. MS: 240 (M-t-butoxy)+.

The t-butoxycarbonyl group was cleaved off with hydrogen chloride in dioxane in an analogous manner to that described in Example 1 to obtained (4S)-amino-(5S)-hydroxy-(7S)-isopropyl-2-methyl-8-nonene, which was was used directly in the next step without further purification.

A mixture of 550 mg (1.75 mmol) of (4S)-amino(5S)-hydroxy-(7S)-isopropyl-2-methyl-8-nonene, 1.547 mg (2.65 mmol) of N-α-N-im-Bis-Fmoc-L-histidine, 2.323 g of BOP and 0.73 ml of triethylamine in 30 ml of acetonitrile was stirred at room temperature for 4 days. Thereafter, the solvent was evaporated under reduced pressure and the residue was worked-up in a manner analogous to that described in Example 1. Chromatography of the crude product on 500 g of silica gel with a 140:5:0.5 mixture of methylene chloride, methanol and ammonia yielded 950 mg of fluoren-9-ylmethyl [(S)-1-[[(1S,2S,4S)-2-hydroxy-1-isobutyl-4-isopropyl-5-hexenyl]carbamoyl]-2-imidazol-4-ylethyl] carbamate as an oil, which was used directly in the next step, MS: 369 (M+H)+.

1.3 g of fluoren-9-ylmethyl [(S)-1-[[(1S,2S,4S)-2-hydroxy-1-isobutyl-4-isopropyl-5-hexenyl]carbamoyl]-2-imidazol-4-ylethyl]carbamate in 30 ml of methylene chloride and 2 ml of piperidine were stirred at room temperature for 1.5 hours. Thereafter, the solvent was evaporated and the residue was triturated with hexane. The (S)-α-amino-N-[(1S,2S,4S)-2-hydroxy-1-isobutyl-4-isopropyl-5-hexenyl]-imidazole-4-propionamide so obtained was used in the next step without further purification.

EXAMPLE 42

A mixture of 460 mg (1.18 mmol) of (S)-α-amino-N-[(1S,2S,4S)-1-(cyclohexylmethyl)-2-hydroxy-4-isopropyl-5-hexenyl]imidazole-4-propionamide, 313 mg (1.18 mmol) of t-butoxycarbonyl-L-phenylalanine, 0.15 ml (1.18 mmol) of 4-ethylmorpholine, 320 mg (2.36 mmol) of HOBT and 292 mg (1.42 mmol) of DCC in 20 ml of dimethylformamide was stirred at room temperature for 18 hours and subsequently worked-up in the usual manner. Chromatography of the residue on 30 g of silica gel using a 20:1:0.1 mixture of methylene chloride, methanol and ammonia as the eluting agent yielded 410 mg of crystals of melting point 161°.

2.5 g of the above compound were dissolved in 50 ml of 2.2N hydrogen chloride in dioxane and stirred at room temperature for 6 hours. Thereafter, the reaction mixture was evaporated under reduced pressure and the residue was purified by chromatography on silica gel with a 190:10:1 mixture of methylene chloride, methanol and ammonia, to obtain N-[(1S,2S,4S)-1-(cyclohexyl-methyl)-2-hydroxy-4-isopropyl-5-hexenyl]-α-(3-phenyl-L-alanyl)imidazole-4-propionamide as a uniform material. MS: 538 (M+H)+.

EXAMPLE 6

The following compounds were prepared in an analogous manner to that described in Example 1:

From (S)-α-amino-N-[(1S,2S,4S)-1-(cyclohexylmethyl)-2-hydroxy-4-isopropyl-5-hexenyl]imidazole-4-propionamide and α-benzyltetrahydro-oxo-4H-1,4-oxazinepropionic acid, the (S)-N-[(1S,2S,4S)-1-(cyclohexylmethyl)-2-hydroxy-4-isopropyl-5-hexenyl]-α-[(RS)-α-(morpholinocarbonyl)hydrocinnamamido)imidazole-4-propionamide as crystals of melting point 94° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and t-butoxycarbonyl-D-proline, the (2S,3S,5S)-2-(Boc-D-Pro-Phe-His-NH)-1-cyclohexyl-5-isopropyl-6-hepten-3-ol as crystals of melting point 132° (from methylene chloride/ether/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and t-butylacetic acid, the (S)-N-[(1S,2S,4S)-1-(cyclohexylmethyl)-2-hydroxy-4-isopropyl-5-hexenyl]-α-[(S)-α-(3,3-dimethylbutyramido)hydrocinnamoyl]-imidazole-4-propionamide as crystals of melting point 105° (dec.; from methylene chloride/ether/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and isovaleric acid, the N-(S)-[(1S,2S,4S)-1-(cyclohexylmethyl)-2-hydroxy-4-isopropyl-5-hexenyl]-α-[(S)-α-3-methylbutyramido]imidazole-4-propionamide as a foam, MS: 622 (M+H)+;

From (S)-α-amino-N-[(1S,2S,4S)-1-(cyclohexylmethyl)-2-hydroxy-4-isopropyl-5-hexenyl]imidazole-4-propionamide and (S)-α-[[(S)-2-benzylamino-3-phenylpropyl]amino]hydrocinnamic acid, the benzyl [α-[[-[α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl]amino]methyl]phenethyl]carbamate as crystals of melting point 89° (from methylene chloride/ether/hexane);

From (S)-α-amino-N-[(S)-1-[[(1S,2S,4S)-2-hydroxy-1-isobutyl-4-isopropyl-5-hexenyl]carbamoyl]-2-imidazol-4-ylethyl]hydrocinnamamide, which was obtained from t-butyl [(S)-α-[[(S)-1-[[(1S,2S,4S)-2-hydroxy-1-isobutyl-4-isopropyl-5-hexenyl]carbamoyl]-2-imidazole-4-ylethyl]carbamoyl]-phenethyl] carbamate by allowing to stand at room temperature for 18 hours in 0.3N methanolic hydrochloric acid, and cyclopentanecarboxylic acid, the (S)-α-[(RS)-cyclopentanecarboxamido]-N-[(S)-1-[[(1S,2S,4S)-2-hydroxy-1-isobutyl-4-isopropyl-5-hexenyl]carbamoyl]-2-imidazol-4-ylethyl]hydrocinnamamide as crystals of melting point 185° (dec,; from methanol/methylene chloride/hexane):

From N-[(1S,2S,4S)-1-(cyclohexylmethyl)-2-hydroxy-4-isopropyl-5-hexenyl]-α-(3-phenyl-L-alanyl-)imidazole-4-propianamide and benzyl [(methylthio)formimidoyl] carbamate[1], the benzyl [N-[(S)-α-[[(S)-1-[[(1S,2S,4S)-1-(cyclohexylmethyl)- 2-hydroxy-4-isopropyl-5-hexenyl]-carbamoyl]-2-imidazol-4-ylethyl]carbamoyl]-phenethyl]amidino] carbamate as a foam, MS: 714 (M+H)+;
[1]GB Patent Specification 2.085.444

From N-[(1S,2S,4S)-1-(cyclohexylmethyl)-2-hydroxy-4-isopropyl-5-hexenyl]-α-(3-phenyl-L-alanyl-)imidazole-4-propianamide and t-butoxycarbonylaminovaleric acid, the t-butyl [4[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl]carbamoyl]-butyl] carbamate as crystals of melting point 110° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and N-t-butoxycarbonyl-N-methyl-L-phenylalanine, the t-butyl [(S)-α-[[(S)-1-(S)-[[(1S,2S,4S)-1-(cyclohexylmethyl)-2-hydroxy-4-isopropyl-5-hexenyl]carbamoyl]-2-imidazol-4-ylethyl]carbamoyl]phenethyl]methyl carbamate as crystals of melting point 93° (from ether/hexane);

From (S)-α-amino-N-[(1S,2S,4R)-1-(cyclohexylmethyl)-2-hydroxy-4-isopropyl-5-hexenyl]imidazole-4-propionamide and t-butoxycarbonyl-L-phenylalanine, the (2S,3S,5R)-2-(Boc-phe-His-NH)-1-cyclohexyl-5-isopropyl-6-hepten-3-ol as a foam. MS 638 (M+H)+;

From (S)-α-amino-N-[(1S,2S,4S)-1-(cyclohexylmethyl)-2-hydroxy-4-isopropyl-5-hexenyl]imidazole-4-propionamide and dibenzsuberaneacetic acid[2], the N-[(1S,2S,4S)-1-(cyclohexylmethyl)-2-hydroxy-4-isopropyl-5-hexenyl]-α-[2-(10,11-dihydro-5H-dibenzo(a,d]cyclohepten-5-yl)acetamido]imidazole-4-propionamide as crystals of melting point 135° (from methylene chloride/ether/hexane);
[2]EPA 0.056.616

From (S)-α-amino-N-[(1S,2S,4S)-1-(cyclohexylmethyl)-2-hydroxy-4-isopropyl-5-hexenyl]imidazole-4-propionamide and 3-(3-indolyl)propionic acid, the (S)-N-[(1S,2S,4S)-1-(cyclohexylmethyl)-2-hydroxy-4-isopropyl-5-hexenyl]-α-(3-indol-3-ylpropionamido)imidazole-4-propionamide as a solid of melting point 122° (from ether/hexane);

From (S)-α-amino-N-[(1S,2S,4S)-1-(cyclohexylmethyl)-2-hydroxy-4-isopropyl-5-hexenyl]imidazole-4-propionamide and benzylmalonic acid monoamide, the (S)-α-[(RS)-α-carbamoylhydrocinnamamido]-N-[(1S,2S,4S)-1-(cyclohexylmethyl)-2-hydroxy-4-isopropyl-5-hexenyl]imidazole-4-propionamide as a foam, MS: 566 (M+H)+;

From (S)-α-amino-N-[(1S,2S,4S)-1-(cyclohexylmethyl)-2-hydroxy-4-isopropyl-5-hexenyl]imidazole-4-propionamide and (S)-α-benzyl-2,5-dimethylpyrrol-1-acetic acid, the (S)-N-[(1S,2S,4S)-1-(cyclohexylmethyl)-2-hydroxy-4-isopropyl-5-hexenyl]-α-[(S)-α-(2,5-dimethylpyrrol-1-yl)hydrocinnamamido]imidazole-4-propionamide as crystals of melting point 93° (from ether/hexane);

From (S)-α-amino-N-[(1S,2S,4S)-1-(cyclohexylmethyl)-2-hydroxy-4-isopropyl-5-hexenyl]imidazole-4-propionamide and α-[(2-hydroxyethyl)carbamoyl]hydrocinnamic acid, the (S)-N-[(1S,2S,4S)-1-(cyclohexylmethyl)-2-hydroxy-4-isopropyl-5-hexenyl]-α-[(RS)-α-[(2-hydroxyethyl)carbamoyl]hydrocinnamamido]imidazole-4-propionamide as a foam, MS: 610 (M+H)+;

From (S)-α-amino-N-[(1S,2S,4S)-1-(cyclohexylmethyl)-2-hydroxy-4-isopropyl-5-hexenyl]imidazole-4-propionamide and α-[[2-(dimethylamino)ethyl]carbamoyl]hydrocinnamic acid, the (S)-N-[(1S,2S,4S)-1-(cyclohexylmethyl)-2-hydroxy-4-isopropyl-5-hexenyl-α-[(RS)-α-[[2-(dimethylamino)ethyl]carbamoyl]hydrocinnamamido]imidazole-4-propionamide as a foam, MS: 637 (M+H)+;

From (S)-α-amino-N-[(1S,2S,4S)-1-(cyclohexylmethyl)-2-hydroxy-4-isopropyl-5-hexenyl]imidazole-4-propionamide and dibenzyl-cyanoacetic acid, the (S)-α-(α-benzyl-α-cyanohydrocinnamamido)-N-[(1S,2S,4S)-1-(cyclohexylmethyl)-2-hydroxy -4-isopropyl-5-hexenyl]imidazole-4-propionamide as crystals of melting point 105° (from ether/hexane);

From (S)-α-amino-N-[(1S,2S,4S)-1-(cyclohexylmethyl)-2-hydroxy-4-isopropyl-5-hexenyl]imidazole-4-propionamide and benzyl-cyanoacetic acid, the (RS)-α-cyano-N-[(S)-1-[[(1S,2S,4S)-1-(cyclohexylmethyl)-2-hydroxy-4-isopropyl 5-hexenyl]carbamoyl]-2-imidazol-4-ylethyl]hydrocinnamamide as crystals of melting point 97° (from methylene chloride/ether/hexane;

From (S)-α-amino-N-[(1S,2S,4S)-1-(cyclohexylmethyl)-2-hydroxy-4-isopropyl-5-hexenyl]imidazole-4-propionamide and indole-2-carboxylic acid, the N-[(S)-1-[[(1S,2S,4S)-1-(cyclohexylmethyl)-2-hydroxy-4-isopropyl-5-hexenyl]carbamoyl]-2-imidazol-4-yl-ethyl]-2-benzimidazolecarboxamide as crystals of melting point 123° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and isovaleric acid, the (S)-N-[(1S,2S,4S)-1-(cyclohexylmethyl)-2-hydroxy-4-isopropyl-5-hexenyl]-α-(3-methylbutyramido)imidazole-4-propionamide as a foam, MS; 622 (M+H)+;

From (S)-α-amino-N-[(1S,2S,4S)-1-(cyclohexylmethyl)-2-hydroxy-4-isopropyl-5-hexenyl]imidazole-4-propionamide and α-benzyl- -oxo-1-pyrrolidinepropionic acid, the N-[(1S,2S,4S)-1-(cyclohexylmethyl)-2-hydroxy-4-isopropyl-5-hexenyl]-α-[(RS)-α-(1-pyrrolidinylcarbonyl)hydrocinnamamido]imidazole-4-propionamide as crystals of melting point 89° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and α-[(benzyloxy)carbamoyl]hydrocinnamic acid, the (S)-α-[(RS)-α-[(benzyloxy)carbamoyl]hydrocinnamamido]-N-[(1S,2S,4S)-1-cyclohexyl-2-hydroxy-4-isopropyl-5-hexenyl]imidazole-4-propionamide as crystals of melting point 104° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and 1-[α-(methoxycarbonyl)hydrocinnamoyl]-4-piperidinecarboxylic acid, the methyl (RS)-α-[[4-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]piperidino]carbonyl]hydrocinnamate as crystals of melting point 89° (from methylene chloride/ether/hexane).

The acids used as starting materials are either known and obtained commercially or were prepared as follows:

α-Benzyltetrahydro-8-oxo-4H-1,4-oxazinepropionic acid benzylmalonic acid monomethyl ester which in turn had been prepared according to known methods[3], was amidated with morpholine according to usual methods and subsequently hydrolyzed with 1N sodium hydroxide solution to give α-benzyltetrahydro-β-oxo-4H-1,4-oxazinepropionic acid, MS: 264 (M+H)+.

[3] M Goodman et al., J. Am. chem. Soc., 77, 8675 (1969) and Int. J. Pept. Prof. Res., 21, 84 (1983)

(S)-α-[[(S)-2-Benzylamino-3-phenylpropyl]amino]hydrocinnamic acid

In a manner analogous to the preparation of Boc-Phe<sup>R</sup>His(Bom)-OH described in Example 26, there was prepared from N-benzyl-Phe-Phe-OMe by sulfurization of the amide carbonyl group, desulfurization thereof with Raney-nickel and subsequent hydrolysis of the ester obtained, the (S)-α-[[(S)-2-benzylamino-3-phenylpropyl]amino]hydrocinnamic acid which was used directly in the next step.

t-Butoxycarbonylaminovaleric acid

5-Aminovaleric acid was converted under Schotten-Baumann conditions with di-t-butyl carbonate in the usual manner into the corresponding N-protected acid, melting point 48°-50° (from ether/hexane).

Benzylmalonic acid monoamide

Benzylmalonic acid monomethyl ester was amidated with ammonia in the usual manner and the 2-benzyl-2-formamidoacetic acid methyl ester obtained was hydrolyzed with 1N sodium hydroxide solution in a 9:1 mixture of methanol and water within 30 minutes to benzylmalonic acid monoamide, Rf: 0.15 in a 90:10:1:0.5 mixture of chloroform, methanol, water and acetic acid.

(S)-α-Benzyl-2,5-dimethylpyrrole-1-acetic acid

L-phenylalanyl methyl ester hydrochloride was converted into the corresponding free base by shaking with a sodium bicarbonate solution in ether and heated to 100° for 2.5 hours in glacial acetic acid with acetonylacetone. Thereafter, the solvent was evaporated and the residue was filtered with toluene over silica gel, to obtain methyl (S)-α-benzyl-2,5-dimethylpyrrole-1-acetate, MS: 258 (M+H)+. The ester so obtained was allowed to stand at room temperature for 1.5 hours with 1N sodium hydroxide solution in a 9:1 mixture of methanol and water. After extracting the aqueous solution with ether and washing the organic phase, there was obtained (S)-α-benzyl-2,5-dimethylpyrrole-1-acetic acid, MS: 244 (M+H)+, which was used directly in the next step.

α-[(2-Hydroxyethyl)carbamoyl]hydrocinnamic acid

In a manner analogous to that described above for α-benzyltetrahydro-β-oxo-4H-1,4-oxazinepropionic acid, benzylmalonic acid monomethyl ester was amidated with ethanolamine and the compound obtained was saponified to α-[(2-hydroxyethyl)carbamoyl]hydrocinnamic acid, MS: 251 (M)+, which was used directly in the next step.

α-[[2-(Dimethylamino)ethyl]carbamoyl]hydrocinnamic acid

In a manner analogous to that described above for α-benzyltetrahydro-β-oxo-4H-1,4-oxazinepropionic acid, benzylmalonic acid monomethyl ester was amidated with N,N-dimethylaminoethylamine and subsequently saponified to α-[[(2-(dimethylamino)ethyl]carbamoyl]hydrocinnamic acid, [MS: 265 (M+H)+], which was used directly in the next step.

Dibenzyl-cyanoacetic acid

Cyanoacetic acid ethyl ester was dibenzylated in the presence of sodium ethylate with excess benzyl bromide in ethanol to give dibenzyl-cyanoacetic acid ethyl ester, which was hydrolyzed with 1N sodium hydroxide solution in a 9:1 mixture of methanol and water to give dibenzyl-cyano-acetic acid, melting point 194° (from methylene chloride/ methanol/hexane).

Benzyl-cyanoacetic acid

Cyanoacetic acid ethyl ester was alkylated with benzyl bromide in the presence of sodium ethylate in ethanol to give benzyl-cyanoacetic acid ethyl ester [MS: 203 (M)+] which was then subsequently hydrolyzed with 1N sodium hydroxide solution in a 9:1 mixture of methanol and water to give the corresponding acid. Recrystallization of the crude product from methylene chloride/hexane yielded benzyl-cyanoacetic acid as crystals of melting point 97°.

α-Benzyl-β-oxo-1-pyrrolidineoropionic acid

In a manner analogous to that described for α-benzyltetrahydro-β-oxo-4H-1,4-oxazinepropionic acid, benzylmalonic acid monomethyl ester was amidated with pyrrolidine and the product obtained was hydrolyzed to α-benzyl-β-oxo-1-pyrrolidinepropionic acid, which was used directly in the next step, MS: 248 (M+H)+.

α-[(Benzyloxy)carbamoyl]hydrocinnamic acid

In a manner analogous to that described for α-benzyltetrahydro-β-oxo-4H-1,4-oxazinepropionic acid, benzylmalonic acid monomethyl ester was amidated with O-benzylhydroxylamine and the resulting product [MS: 314 (M+H)+] was saponified with 1N sodium hydroxide solution in a 9:1 mixture of methanol and water to the corresponding acid. Recrystallization of the crude product from methanol/methylene chloride/ether yielded α-[(benzyloxy)carbamoyl]hydrocinnamic acid of melting point 147°.

1-[α-(Methoxycarbonyl)hydrocinnamoyl]-4-piperidinecarboxylic acid

In a manner analogous to that described for the preparation of α-benzyltetrahydro-β-oxo-4H-1,4-oxazinepropionic acid, benzylmalonic acid monomethyl ester was amidated with piperidine-4-carboxylic acid ethyl ester and the resulting compound [MS: 347 (M)+] was saponified with 1N sodium hydroxide solution in a mixture of methanol and water at 0° for 2 hours. The crude product obtained was purified by chromatography on silica gel with a 95:5:2 mixture of chloroform, ethanol and ethyl acetate and recrystallized from a mixture of methanol, methylene chloride and ether, to yield 1-[α-(methoxycarbonyl)hydrocinnamoyl]-4-piperidinecarboxylic acid, melting point 138°.

EXAMPLE 7

In a manner analogous to that described in Example 1, N-[(1S,2S,4S)-1-(cyclohexylmethyl)-2-hydroxy-4-isopropyl-5-hexenyl]-α-(3-phenyl-L-alanyl)imidazole-4-propianamide was reacted with di-t-butoxycarbonyl-aminoethylglycine. Chromatographic purification and recrystallization of the crude product yielded di-t-butyl N-[[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-phenylethyl]carbamoyl]methyl]ethylenedicarbamate, melting point 109°.

150 mg of N-[[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenylethyl]carbamoyl]methyl]ethylenedicarbamate were dissolved in 0.3N hydrochloric acid in methanol and allowed to stand at room temperature overnight. Thereafter, the solvent was evaporated and the residue was precipitated from methanol/ethyl acetate, to obtain (S)-α-[(S)-α-[-2-[(2-amino-ethyl)amino]acetamido]hydrocinnamido]-N-[(1S,2S,4S)-1-(cyclohexylmethyl)-2-hydroxy-4-isopropyl-5-hexenyl]-imidazole-4-propionamide trihydrochloride, MS: 638 (M+H)+.

The di-t-butoxycarbonyl-aminoethylglycine used as the starting material was prepared as follows:

N-(2-Aminoethyl)glycine was prepared according to the method described by E. P. Heimer in Int. J. Pept. Prot. Res., 23, 203 (1984) and converted in a known manner under Schotten-Baumann conditions with di-t-butyl carbonate into the corresponding N-protected acid, MS: 319 (M+H)+.

EXAMPLE 8

60 mg of (2S,3S,5S)-2-(Boc-D-Pro-Phe-His-NH)-1-cyclohexyl-5-isopropyl-6-hepten-3-ol were dissolved in 10 ml of 2.1N hydrogen chloride in dioxane and stirred at room temperature for 1.5 hours. The solvent was then evaporated and the residue was treated twice in succession with toluene and thereafter again evaporated to dryness. Crystallization of the thus-obtained residue from methylene chloride/ether/hexane yielded 40 mg of (S)-N-[(1S,2S,4S)-1-(cyclohexylmethyl)-2-hydroxy-4-isopropyl-5-hexenyl]-α-[(S)-α-(D-prolylamino)hydrocinnamamido]-imidazole-4-propionamide dihydrochloride as white crystals of melting point 159°.

EXAMPLE 9

N-Methyl-L-histidine was converted with benzyl alcohol in the presence of hydrochloric acid at room temperature into the corresponding benzyl ester and this was reacted according to the procedure described by D. H. Rich et al. in Proc. 9th American Pept. Symp., Toronto 1985. page 217, with t-butoxycarbonyl-L-phenylalanine in the usual manner. Thereafter, the N-[N-t-butoxycarbonyl)-3-phenyl L-alanyl]-N-methyl-L-histidine benzyl ester obtained was hydrogenated for one hour in the presence of 5% palladium on carbon, to obtain N-[N-(t-butoxy-carbonyl)-3-phenyl L-alanyl]-N-methyl-L-histidine, Rf: 0.2 in a 80:20:3:3 mixture of chloroform, methanol, water and acetic acid. This compound was then reacted in the usual manner with (αS,βS)-β-amino-α-[(S)-2-isopropyl-3-butenyl]cyclohexanepropanol. The crude product obtained was then chromatographed on silica gel with a 20:1:0.1 mixture of methylene chloride, methanol and ammonia, upon which the two epimeric compounds were separated. Recrystallization of the crude product obtained from the first fraction from ether/methylene chloride/hexane yielded t-butyl [(S)-α-[[(S)-1-[[(1S,2S,4S)-1-(cyclohexylmethyl)-2-hydroxy-4-isopropyl-5-hexenyl]carbamoyl]-2-imidazol-4-ylethyl]methylcarbamoyl]-phenylethyl] carbamate as white crystals of melting point 95°.

From the second fraction, there was obtained after recrystallization from ether/methylene chloride/hexane the epimeric compound t-butyl [(S)-α-[[(R)-1-[[(1S,2S,4S)-1-(cyclohexylmethyl)-2-hydroxy-4-isopropyl-5-hexenyl]-carbamoyl]-2-imidazol-4-ylethyl]methylcarbamoyl]phenethyl] carbamate as white crystals of melting point 85°.

In a manner analogous to that described above, N-t-butoxycarbonyl-N-methyl-L-phenylalanine was reacted with N-methyl-L-histidine benzyl ester according to the method described by Rich et al., the ester obtained was subsequently hydrogenated to the corresponding acid, and this was reacted in the usual manner with (αS,βS)-β-amino-α-[(S)-2-isopropyl-3-butenyl]cyclohexanepropanol. Chromatographic purification of the crude product on silica gel with a 140:1:0.1 mixture of methylene chloride, methanol and ammonia yielded thin-layer chromatographically pure t-butyl [(S)-α-[[(S)-α-[[(1S,2S,4S)-1-(cyclohexylmethyl)-2-hydroxy-4-isopropyl-5-hexenyl]-carbamoyl]-2-imidazol-4-ylethyl]-methylcarbamoyl]phenethyl]-methyl carbamate in the form of a foam, MS: 666 (M+H)+.

EXAMPLE 10

150 mg (0.20 mmol) of t-butyl 2-benzyl-2-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-3-phenylpropyl] carbamate were dissolved in 10 ml of 0.3N methanolic hydrochloric acid and allowed to stand at room temperature overnight. Thereafter, the solvent was evaporated and, for purification, the residue was chromatographed on 30 g of silica gel with a 20:1:0.1 mixture of methylene chloride, methanol and ammonia as the eluting agent. Recrystallization of the thus-obtained crude product from methylene chloride/ether/hexane yielded (S)-α-(3-amino-2,2-dibenzylpropionamido)-N-[(1S,2S,4S)-1-(cyclohexylmethyl)-2-hydroxy-4-isopropyl-5-hexenyl]-imidazole-4-propionamide as white crystals of melting point 89°.

The t-butyl 2-benzyl-2-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-3-phenylpropyl] carbamate used as the starting material was prepared as follows:

Dibenzylcyanoacetic acid methyl ester was reduced with Raney-nickel in methanolic ammonia to dibenzylmethylaminoacetic acid ethyl ester [MS: 284 (M) ], which was then protected at the amino group with di-t-butyl carbonate in triethylamine in the usual manner. The ester [MS: 398 (M+H)+]obtained in this manner was subsequently saponified with 1N sodium hydroxide solution in a mixture of methanol and water to the corresponding acid which, after recrystallization from methanol/methylene chloride/hexane, was isolated as crystals of melting point 157°. The acid was thereafter reacted in the usual manner with (S)-α-amino-N-[(1S,2S,4S)-1-(cyclohexylmethyl)-2-hydroxy-4-isopropyl-5-hexenyl]imidazole-4-propionamide to give t-butyl 2-benzyl-2-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-3-phenylpropyl] carbamate. Recrystallization from methylene chloride/hexane/ether yielded white crystals of melting point 97°.

EXAMPLE 11

150 mg of (S)-α-[(RS)-α-[(benzyloxy)carbamoyl]-hydrocinnamamido]-N-[(1S,2S,4S)-1-cyclohexyl-2-hydroxy 4-isopropyl-5-hexenyl]imidazole-4-propionamide were hydrogenated in the presence of 5% palladium on carbon in methanol for 3 hours. After completion of hydrogen uptake, the catalyst was filtered and the filtrate was evaporated. Recrystallization of the residue from methanol/methylene chloride/ether yielded (S)-N-[(1S,2S,4S)-1-(cyclohexylmethyl)-4-ethyl-2-hydroxy-5-methylhexyl]-α-[(RS)-α-(hydroxycarbamoyl)hydrocinnamamido]imidazole-4-propionamide as white crystals of melting point 123°.

EXAMPLE 12

120 mg of t-butyl [(S)-α-[[(S)-1-(S)-[[(1S,2S,4S)-1-(cyclohexylmethyl)-2-hydroxy-4-isopropyl-5-hexenyl]-carbamoyl] -2-imidazol-4-ylethyl]carbamoyl]phenethyl]-methyl carbamate were dissolved in 0.3N methanolic hydrochloric acid and stirred at room temperature overnight. Thereafter, the solvent was evaporated and the residue was treated with t-butylacetyl chloride and triethylamine in tetrahydrofuran and allowed to stand at room temperature overnight. After the usual working-up, chromatographic purification on silica gel using a 20:1:0.1 mixture of methylene chloride, methanol and ammonia, and recrystallization from ether/hexane, there was obtained (S)-N-[(1S,2S,4S)-1-(cyclohexylmethyl)-2-hydroxy-4-isopropyl-5-hexenyl]-α-[(S)-α-(N,3,3-trimethyl-butyramido)hydrocinnamamido]imidazole-4-propionamide as white crystals of melting point 126°.

EXAMPLE 13

The following compounds were prepared in a manner analogous to that described in Example 1:

From N-[(1S,2S,4S)-1-(cyclohexylmethyl)-2-hydroxy-4-isopropyl-5-hexenyl]-α-(3-phenyl L-alanyl)imidazole-4-propionamide and 3-(4-hydroxyphenyl)-propionic acid, the (S)-N-[(1S,2S,4S)-1-(cyclohexylmethyl)-2-hydroxy-4-isopropyl-5-hexenyl]-α-[(S)-α-(p-hydroxyhydrocinnamamido)-hydrocinnamamido]imidazole-4-propionamide as white crystals, melting point 120° (from methylene chloride/ether/hexane);

From N-[(1S,2S,4S)-1-(cyclohexylmethyl)-2-hydroxy-4-isopropyl-5-hexenyl]-α-(3-phenyl-L-alanyl)imidazole-4-propionamide and nicotinic acid, the (S)-N-[(1S,2S,4S)-1-(cyclohexylmethyl)-2-hydroxy-4-isopropyl-5-hexenyl]-α-[(S)-α-nicotinamidohydrocinnamamido]imidazole-4-propionamide as a solid, MS: 643 (M+H)+;

From N-[(1S,2S,4S)-1-(cyclohexylmethyl)-2-hydroxy-4-isopropyl-5-hexenyl]-α-(3-phenyl L-alanyl)imidazole-4-propionamide and 3-(4-pyridyl)acrylic acid, the (S)-N-[(1S,2S,4S)-1-(cyclohexylmethyl)-2-hydroxy-4-isopropyl-5-hexenyl]-α-[[(S)-α-[(E)-4-pyridineacrylamido]-hydrocinnamamido]imidazole-4-propionamide as yellowish crystals, melting point 135° (dec.; from methylene chloride/ether/hexane);

From N-[(1S,2S,4S)-1-(cyclohexylmethyl)-2-hydroxy-4-isopropyl-5-hexenyl]-α-(3-phenyl-L-alanyl)imidazole-4-propionamide and 3-(3-pyridyl)acrylic acid, the (S)-[(1S,2S,4S) 1-(cyclohexylmethyl)-2-hydroxy-4-isopropyl-5-hexenyl]-α-[(S)-α-(3-pyridineacrylamido)-hydrocinnamamido]imidazole-4-propionamide as yellowish crystals, melting point 141° (from methylene chloride/ether);

From N-[(1S,2S,4S)-1-(cyclohexylmethyl)-2-hydroxy-4-isopropyl-5-hexenyl]-α-(3-phenyl-L-alanyl)imidazole-4-propionamide and 3-(4-imidazolyl)acrylic acid (urocanic acid), the (S)-N-[(1S,2S,4S)-1-(cyclohexylmethyl)-2-hydroxy-4-isopropyl-5-hexenyl]-α-[(S)-α-(imidazol-4-acrylamido)hydrocinnamamido]imidazole-4-propionamide as white crystals, melting point 150°-152° (from methylene chloride/methanol/ether);

From N-[(1S,2S,4S)-1-(cyclohexylmethyl)-2-hydroxy-4-isopropyl-5-hexenyl]-α-(3-phenyl-L-alanyl)imidazole-4-propionamide and D-(−)-quinic acid, the (S)-N-[(1S,2S,4S)-1-(cyclohexylmethyl)-2-hydroxy-4-isopropyl-5-hexenyl]-α-[(S)-α-(1,3,4,5-tetrahydroxycyclohexanecarboxamido)hydrocinnamamido]imidazole-4-propionamide as a white solid, MS: 712 (M+H)+;

From N-[(1S,2S,4S)-1-(cyclohexylmethyl)-2-hydroxy-4-isopropyl-5-hexenyl]-α-(3-phenyl-L-alanyl)imidazole-4-propionamide and quinaldic acid, the N-[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]phenethyl]-2-quinolinecarboxamide as a white solid, MS: 693 (M+H)+;

From N-[(1S,2S,4S)-1-(cyclohexylmethyl)-2-hydroxy-4-isopropyl-5-hexenyl]-α-(3-phenyl-L-alanyl)imidazole-4-propionamide and levulinic acid, the (S)-

N-[(1S,2S,4S)-1-(cyclohexylmethyl)-2-hydroxy-4-isopropyl-5-hexenyl]-α-[(S)-α-(4-oxavaleramido)hydrocinnamamido]imidazole-4-propionamide as white crystals, melting point 150° (dec.; from methylene chloride/ether/hexane);

From N-[(1S,2S,4S)-1-(cyclohexylmethyl)-2-hydroxy-4-isopropyl-5-hexenyl]-α-(3-phenyl L-alanyl-)imidazole-4-propionamide and 3-pyridylacetic acid, the (S)-N-[(1S,2S,4S)-1-(cyclohexylmethyl)-2-hydroxy-4-isopropyl-5-hexenyl]-α-[(S)-α-(3-pyridineacetamido)-hydrocinnamamido]-imidazole-4-propionamide as white crystals, melting point 195° (dec.; from methanol/methylene chloride/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and 4-chlorocinnamic acid, the (S)-N-[(1S,2S,4S)-1-(cyclohexylmethyl)-2-hydroxy-4-isopropyl-5-hexenyl]-α[(S)-α-(4-chlorocinnamamido)hydrocinnamamido]imidazole-4-propionamide as white crystals, melting point 139° (from methylene chloride/methanol/ether);

From N-[(1S,2S,4S)-1-(cyclohexylmethyl)-2-hydroxy-4-isopropyl-5-hexenyl]-α-(3-phenyl-L-alanyl-)imidazole-4-propionamide and trans-4-nitrocinnamic acid, the (S)-N-[(1S,2S,4S)-1-(cyclohexylmethyl)-2-hydroxy-4-isopropyl-5-hexenyl]-α-[(S)-α-(4-nitrocinnamamido)hydrocinnamamido]imidazole-4-propionamide as yellowish crystals, melting point 120° (dec.; from methylene chloride/methanol/ether);

From N-[(1S,2S,4S)-1-(cyclohexylmethyl)-2-hydroxy-4-isopropyl-5-hexenyl]-α-(3-phenyl-L-alanyl-)imidazole-4-propionamide and fumaric acid monoethyl ester, the ethyl 3-[[(S)-α-[[(S)-1-[[(1S,2S,4S)-1-(cyclohexylmethyl)-2-hydroxy-b 4-isopropyl-5-hexenyl]-carbamoyl]-2-imidazol-4-ylethyl]carbamoyl]phenethyl]carbamoyl]acrylate as white crystals, melting point 175° (dec.; from methylene chloride/methanol/hexane);

From (S)-α-amino-N-[(1S,2S,4S)-1-(cyclohexylmethyl)-2-hydroxy-4-isopropyl-5-hexenyl]imidazole-4-propionamide and diphenylcarbamoyl-L-phenyl-alanine, an epimeric mixture of (S)-N-[(1S,2S,4S)-1-(cyclohexylmethyl)-2-hydroxy-b 4-isopropyl-5-hexenyl]-α-[[N-(diphenylcarbamoyl)-3-phenyl-L-alanyl-]amino]imidazole-4-propionamide and (S)-N-[(1S,2S,4S)-1-(cyclohexylmethyl)-2-hydroxy-4-isopropyl-5-hexenyl]-α-[[N-(diphenylcarbamoyl)-3-phenyl D-alanyl]amino]imidazole-4-propionamide, in which the first-named epimer predominates, melting point 106° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and isobutoxycarbonyl-L-phenylalanine, the isobutyl [(S)-α-[[(S)-1-[ [(1S,2S,4S)-1-(cyclohexylmethyl)-2-hydroxy-4-isopropyl-5-hexenyl]carbamoyl]-2-imidazol-4-ylethyl]carbamoyl]phenethyl]carbamate as white crystals, melting point 147° (from ether/methylene chloride/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and D-pyroglutamic acid, the (S)-N-[(1S,2S,4S)-1-[cyclohexylmethyl]-2-hydroxy-4-isopropyl-5-hexenyl]-α-[(S)-α-[[5-oxo-D prolyl-]amino]hydrocinnanamido]-imidazole-4-propionamide as a white solid, melting point 200° (dec.; from methanol/ethyl acetate/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and L-pyroglutamic acid, the (S)-N-[(1S,2S,4S)-1-[cyclohexylmethyl]-2-hydroxy-4-isopropyl 5-hexenyl]-α-[(S)-α-[[5-oxo-L-prolyl-]amino]hydrocinnamamido]-imidazole-4-propionamide as white crystals, melting point 148° (from methylene chloride/methanol/ether);

From N-[(1S,2S,4S)-1-(cyclohexylmethyl)-2-hydroxy-4-isopropyl-5-hexenyl]-α-(3-phenyl-L-alanyl-)imidazole-4-propionamide and N-t-butoxycarbonyl-α-methyl-L-alanine, the t-butyl [1-[[(S)-α-[[(S)--1-[[(1S,2S,4S)-1-(cyclohexylmethyl)-2-hydroxy-4-isopropyl-5-hexenyl]carbamoyl]-2-imidazole-4-ylethyl]carbamoyl]phenethyl]-carbamoyl]-1-methylethyl]-carbamate as white crystals, melting point 112° (from methylene chloride/tetrahydrofuran/hexane);

From N-[(1S,2S,4S)-1-(cyclohexylmethyl)-2-hydroxy-4-isopropyl-5-hexenyl]-α-(3-phenyl-L-alanyl-)imidazole- 4-propionamide and Fmoc-Ser(t-Bu)OH, the 9H-fluoren-9-yl [(S)-2-t-butoxy-1-[[(S)-α-[[(S)-1-[[(1S,2S,4S)-1-(cyclohexylmethyl)-2-hydroxy-4-isopropyl-5-hexenyl]-carbamoyl]-2-imidazol-4-ylethyl]carbamoyl]-phenethyl]carbamoyl]ethyl] carbamate as a white solid, melting point 180° (dec.; from methylene chloride/ether/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and dibenzylsuberaneacetic acid, the (S)-N-[(1S,2S,4S)]-1-(cyclohexylmethyl)-2-hydroxy-4-isopropyl-5-hexenyl]-α-[[N-(9H-fluoren-9-ylacetyl)-3-phenyl-L-alanyl]amino]imidazole-4-propionamide as white crystals, melting point 119° (from methylene chloride/ether/hexane);

From N-[(1S,2S,4S)-1-(cyclohexylmethyl) 2-hydroxy-4-isopropyl-5-hexenyl]-α-(3-phenyl-L-alanyl-)imidazole-4-propionamide and adamantylacetic acid, the (S)-α-[[N-(1-adamantylacetyl)-3-phenyl-L-alanyl-]amino]-N-[(1S,2S,4S)-1-[cyclohexylmethyl)-2-hydroxy-4-isopropyl-5-hexenyl]-imidazole-4-propionamide as white crystals, melting point 120° (from methylene chloride/ether/hexane);

From (S)-α-amino-N-[(1S,2S,4S)-1-(cyclohexylmethyl)-2-hydroxy-4-isopropyl-5-hexenyl]imidazole-4-propionamide and phenyloxycarbonyl-L-phenylalanine, the benzyl [(S)-α-[[(S)-1-[[(1S,2S,4S)-1-(cyclohexylmethyl)-2-hydroxy-4-isopropyl 5-hexenyl]carbamoyl]-2-imidazol-4-ylethyl]-carbamoyl]phenethyl] carbamate as white crystals, melting point 144° (from methylene chloride/ether);

From (S)-α-amino-N-[(1S,2S,4S)-1-(cyclohexylmethyl)-2-hydroxy-4-isopropyl-5-hexenyl]imidazole-4-propionamide and 2,2,2-trichloroethoxycarbonyl-L-phenylalanine, the 2,2,2-trichloroethyl [(S)-α-[[(S)-1-[[(1S,2S,4S)-1-(cyclohexylmethyl)-2-hydroxy-4-isopropyl-5-hexenyl]-carbamoyl]-2-imidazol-4-ylethyl]carbamoyl]-phenethyl] carbamate as white crystals, melting point 109° (from methylene chloride/hexane);

From N-[(1S,2S,4S)-1-(cyclohexylmethyl)-2-hydroxy-4-isopropylhexyl]-α-[(3-phenyl-N-D-prolyl-L-alanyl)amino]imidazole-4-propionamide and 4-imidazolylpropionic acid, which in turn was prepared by hydrogenating urocanic acid, the N-[(1S,2S,4S)-1-(cyclohexylmethyl)-2-hydroxy-4-isopropylhexyl]-α-[(S)-α-[(R)-1-(3-imidazol-4-ylpropionyl]-2-pyrrolidinecarboxamido]hydrocinnamamido]imidazole-4-propionamide in the form of a foam, MS: 760 (M+H)$^+$;

From N-[(1S,2S,4S)-1-(cyclohexylmethyl)-2-hydroxy-4-isopropyl-5-hexenyl]-α-(3-phenyl-L-alanyl-)imidazole-4-propionamide and (R)-1-[(3-hydroxy-2-pyridyl)carbonyl]-2-pyrrolidinecarboxylic acid, the (S)-N-[(1S,2S,4S)-1-(cyclohexylmethyl)-2-hydroxy-4-isopropyl-5-hexenyl]-α-[(S)-α-[(R)-1-[(3-hydroxy-2-pyridyl)carbonyl]-2-pyrrolidinecarboxamido]hydrocinnamamido]imidazole-4-propionamide as a white solid, melting point 198° (dec.; from methylene chloride/methanol/ether/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and (R)-1-[(dibenzylacetyl)-2-pyrrolidinecarboxylic acid, the (S)-N [(1S,2S,4S)-1-(cyclohexylmethyl) 2-hydroxy- 4-isopropyl-5-hexenyl]-α-[(S)-α-[(R)-1-(dibenzylacetyl)-2-pyrrolidinecarboxamido]hydrocinnamamido]imidazole-4-propionamide as white crystals, melting point 104° (from methylene chloride/ether/hexane);

From N-[(1S,2S,4S)-1-(cyclohexylmethyl)-2-hydroxy-4-isopropyl-5-hexenyl]-α-(3-phenyl-L-alanyl-)imidazole-4-propionamide and 1-t-butoxycarbonylaminocyclohexanecarboxylic acid, the t-butyl 1-[[(S)-α-[[(S)-1-[(1S,2S,4S)-1-(cyclohexylmethyl-2-hydroxy-4-isopropyl-5-hexenyl]-2-imidazol-4-ylethyl]-carbamoyl]phenethyl]carbamoyl]-cyclohexane carbamate as a white solid, MS: 764 (M+H)+;

From N-[(1S,2S,4S)-1-(cyclohexylmethyl)-2-hydroxy-4-isopropylhexyl]-α-[(3-phenyl-N-D-prolyl-L-alanyl)amino]imidazole-4-propionamide and isovaleric acid, the (S)-N-[(1S,2S,4S)-1-(cyclohexylmethyl)-2-hydroxy-4-isopropylhexyl]-α-[(S)-α-[(R)-1-isovaleryl-2-pyrrolidinecarboxamido]hydrocinnamamido]imidazole-4-propionamide as a foam, MS: 721 (M+H)+;

From (S)-N-[(1S,2S,4S)-1-(cyclohexylmethyl)-2-hydroxy-4-isopropyl-5-hexenyl]-α-[(S)-α-(D-prolylamino)hydrocinnamamido]imidazole-4-propionamide dihydrochloride and isovaleric acid, the (S)-N-[(1S,2S,4S)-1-(cyclohexylmethyl)-2-hydroxy-4-isopropyl-5-hexenyl]-α-[[(S)-α-[(1-isovaleryl-L-propyl)carbonyl]-3-phenyl-L-alanyl]amino]-imidazole-4-propionamide as a foam, MS: 719 (M+H)+.

The N-[(1S,2S,4S)-1-(cyclohexylmethyl)-2-hydroxy-4-isopropylhexyl]-α-[(3-phenyl-N-D-prolyl-L-alanyl-)amino]-imidazole-4-propionamide used as the starting material was prepared from the t-butyl (R)-2-[[(S)-α-[[(S)-1-[(1S,2S,4S)-1-(cyclohexylmethyl) -2-hydroxy-4-isopropylhexyl]-2-imidazol-4-ylethyl]carbamoyl]phenethyl]carbamoyl]-1-pyrrolidinecarboxylate described in Example 16 by cleaving off the t-butoxycarbonyl group with hydrogen chloride in dioxane in a manner analogous to that described in Example 8.

The acids used as starting materials are either known and available commercially or were prepared as follows:

Diphenylcarbamoyl-L-phenylalanine

Treatment of L-phenylalanine with diphenylcarbamoyl chloride in dimethylformamide in the presence of triethylamine yielded, after recrystallization from methanol/methylene chloride/hexane, the desired acid in the form of white crystals, melting point 167°.

Isobutoxycarbonyl-L-phenylalanine

Treatment of L-phenylalanine with isobutyl chloroformate in a manner analogous to that described above, yielded yielded the desired acid as an oil [MS: 266 (M+H)+] which crystallized out upon standing and which was used directly in the next step.

Phenyloxycarbonyl-L-phenylalanine

In a manner analogous to that described above, by reacting L-phenylalanine and phenyl chloroformate there was obtained the desired acid in the form of a foam [MS: 286 (M+H)+] which was used directly in the next step.

2,2,2-Trichloroethoxycarbonyl-L-phenylalanine

L-phenylalanine was reacted with 2,2,2-trichloroethyl chloroformate in a 2N sodium bicarbonate solution, and after the usual working-up there was obtained the desired acid as crystals, melting point 126° (from methylene chloride/hexane).

(R)-1-[(3-Hydroxy-2-pyridyl)carbonyl]-2-pyrrolidinecarboxylic acid

3-Hydroxypicolinic acid was condensed with D-proline benzyl ester in the usual manner and the ester obtained was thereafter converted hydrogenolytically into the desired acid, which was used directly in the next step.

(R)-1-(Dibenzylacetyl)-2-pyrrolidinecarboxylic acid

Dibenzylacetic acid was condensed with D-proline benzyl ester in the usual manner and the ester obtained was converted hydrogenolytically into the desired acid, which was used directly in the next step.

1-t-Butoxycarbonylaminocyclohexanecarboxylic acid

1-Aminocyclohexanecarboxylic acid was converted with di-t-butyl dicarbonate in the usual manner into the corresponding N-protected acid, which was used directly in the next step.

EXAMPLE 14

40 mg of 9H-fluoren-9-yl [(S)-2-t-butoxy-1-[[(-S)-α-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]phenethyl]carbamoyl]ethyl]carbamate were dissolved in 5 ml of methylene chloride and 0.4 ml of piperidine and allowed to stand at room temperature for 2 hours. Thereafter, the reaction mixture was evaporated to dryness and the residue was chromatographed on silica gel with a 14:1:0.1 mixture of methylene chloride, methanol and ammonia. Recrystallization of the crude product yielded (S)-α-[[N-(3-t-butoxy-L-alanyl)-3-phenyl-L-alanyl]amino]-N-[(1S,4S)-1-(cyclohexylmethyl)-2-hydroxy-4-isopropyl-5-hexenyl]imidazole-propionamide as a white solid, melting point 103° (dec.; from methylene chloride/ ether/hexane).

EXAMPLE 15 t-Butyl [4[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl]carbamoyl]-butyl] carbamate was dissolved in 0.3N methanolic hydrochloric acid and allowed to stand at room temperature for 18 hours. Thereafter, the reaction mixture was evaporated to dryness and the residue was chromatographed on silica gel, with (S)-α-(5-aminovaleramido)-N-[(S)-1-[[(1S,2S,4S)-1-(cyclohexylmethyl)-2-hydroxy-4-isopropyl 5-hexenyl]-carbamoyl]-2-imidazol-4-ylethyl]hydrocinnamamide dihydro-chloride being obtained as a foam, MS: 637 (M+H)+.

In a manner analogous to that described above, but using 3.5N hydrogen chloride in acetic acid, from t- butyl (R)-2-[[(S)-α-[[(S)-1-[(1S,2S,4S)-1-(cyclohexylmethyl)-2-hydroxy-4-isopropylhexyl]2-imidazol-4-ylethyl]carbamoyl]-phenethyl]carbamoyl]-1-pyrrolidinecarboxylate, the preparation of which was described in Example 16, there was obtained N-[(1S,2S,4S)-1-(cyclohexylmethyl)-2-hydroxy-4-isopropylhexyl]-α-[(3-phenyl-N-D-prolyl-L-alanyl)amino]-imidazole-4-propionamide as a thin-layer chromatographically uniform, hygroscopic solid, MS: 635 (M+H)+.

EXAMPLE 16

The following compounds were prepared by hydrogenating the corresponding olefins in a manner analogous to that described in Example 2:

From ethyl 3-[[(S)-α-[[(S)-1-[[(1S,2S,4S)-1-(cyclohexylmethyl)-2-hydroxy-4-isopropyl 5-hexenyl] carbamoyl]-2-imidazol-4-ylethyl]-carbamoyl]phenethyl]-carbamoyl]acrylate, the ethyl [[(S)-α-[[(S)-1-[[(1S,2S,4S)-1-(cyclohexylmethyl)-2-hydroxy-4-isopropylhexyl]carbamoyl]-2-imidazol-4-ylethyl]carbamoyl]phenethyl]carbamoyl]-propionate as a thin-layer chromatographically uniform solid, MS: 668 (M+H)+;

From (S)-α-[[N-(1-adamantylacetyl)-3-phenyl-L-alanyl]amino]-N-[(1S,2S,4S)-1-[cyclohexylmethyl)-2-hydroxy-4-isopropyl-5-hexenyl]imidazole-4-propionamide, the (S)-α-[(S)-α-[2-(1-adamantyl)acetamido]hydrocinnamamido]-N-[(1S,2S,4S)-1-cyclohexylmethyl)-2-hydroxy-4-isopropylhexyl]imidazole-4-propionamide as a 15 white solid, MS: 717 (M+H)+;

From (S)-N-[(1S,2S,4S)-1-(cyclohexylmethyl)-2-hydroxy-4-isopropyl-5-hexenyl]-α-[(S)-α-(3-pyridineacetamido)hydrocinnamamido]imidazole-4-propionamide, the (S)-N-[(1S,2S,4S)-1-(cyclohexylmethyl)-2-hydroxy-4-isopropylhexyl]-α-[(S)-α-[2-(3-pyridyl)acetamido]hydrocinnamamido]-imidazole-4-propionamide as white crystals, melting point 211° (from methylene chloride/methanol/ether);

From (S)-N-[(1S,2S,4S)-1-[cyclohexylmethyl)-2-hydroxy-4-isopropyl-5-hexenyl]-α[(S)-α-[[5-oxo-L-prolyl]amino]hydrocinnamamido]imidazole-4-propionamide, the (S)-N-[(1S,2S,4S)-1-(cyclohexylmethyl)-2-hydroxy-4-isopropylhexyl]-α-[(S)-α-[(S)-5-oxo-2-pyrrolidinecarboxamido]hydrocinnamamido]imidazole-4-propionamide as a thin-layer chromatographically uniform solid, MS: 651 (M+H)+.

From the epimer mixture of (S)-N-[(1S,2S,4S)-1-[cyclohexylmethyl]-2-hydroxy-4-isopropyl-5-hexenyl]-α-[(S)-α-[[5-oxo-D-prolyl]amino]-hydrocinnamamido]imidazole-4-propionamide and (S)-N-[(1S,2S,4S)]-1-[cyclohexylmethyl]-2-hydroxy-4-isopropyl-5-hexenyl]-α-[(S)-α-[[5-oxo-L-prolyl]amino]hydrocinnamamido]imidazole-4-propionamide, the (S)-N-[(1S,2S,4S)-1-(cyclohexylmethyl)-2-hydroxy-4-isopropylhexyl]-α-[(S)-α-[(RS)-5-oxo-2-pyrrolidinecarboxamido]hydrocinnamamido]-imidazole-4-propionamide as a solid, MS: 651 (M+H)+;

From (S)-N-[(1S,2S,4S)-1-(cyclohexylmethyl)-2-hydroxy-4-isopropyl-5-hexenyl]-α-[[N-(9H-fluoren-9-ylacetyl)-3-phenyl-L-alanyl]amino]-imidazole-4-propionamide, the (S)-N-[(1S,2S,4S)-1-(cyclohexylmethyl)-2-hydroxy-4-isopropylhexyl]-α-[(S)-α-[2-(10,11-dihydro-5H-dibenzo[a,d]-cyclohepten-5-yl)acetamido]-hydrocinnamamido]-imidazole-4-propionamide as a thin-layer chromatographically uniform white solid, MS: 775 (M+H)+;

From (S)-N-[(1S,2S,4S)-1-(cyclohexylmethyl)-2-hydroxy-4-isopropyl-5-hexenyl]-α-[[N-(diphenylcarbamoyl)-3-phenyl-D-alanyl]amino]imidazole-4-propionamide, the ethyl [(S)-α-[[(S)-1-[[(1S,2S,4S)-1-(cyclohexylmethyl)-2-hydroxy-4-isopropylhexyl]carbamoyl]-2-imidazol-4-ylethyl]-carbamoyl]phenethyl] carbamate as white crystals, melting point 196° (from methanol/methylene chloride/ether);

From benzyl [(S)-α-[[(S)-1-[[(1S,2S,4S)-1-(cyclohexylmetehyl)-2-hydroxy-4-isopropyl-5-hexenyl]carbamoyl]-2-imidazol-4-ylethyl]-carbamoyl]phenethyl] carbamate, the phenyl [(S)-α-[[(S)-1-[[(1S,2S,4S)-1-(cyclohexylmethyl)-2-hydroxy 4-isopropylhexyl]carbamoyl]-2-imidazol- 4-ylethyl]carbamoyl]phenethyl] carbamate as white crystals, melting point 157° (from methylene chloride/methanol/ether);

From (S)-N-[(1S,2S,4S)-1-(cyclohexylmethyl)-2-hydroxy-4-isopropyl-5-hexenyl]-α-[(S)-α-(4-nitrocinnamamido)hydrocinnamamido]imidazole-4-propionamide, the (S)-α-[(S)-α-(4-aminohydro-cinnamamido)hydrocinnamamido]-N-[(1S,2S,4S)-1-(cyclohexylmethyl)-2-hydroxy-4-isopropylhexyl]-imidazole-4-propionamide as white crystals, melting point 174° (from methylene chloride/ methanol/ether);

From (2S,3S,5S)-2-(Boc-D-Pro-Phe-His-NH)-1-cyclohexyl-5-isopropyl-6-hepten-3-ol, the t-butyl (R)-2-[[(S)-α-[[(S)-1-[(1S,2S,4S)-1-(cyclohexylmethyl)-2-hydroxy-4-isopropylhexyl]-2-imidazol 4-ylethyl]carbamoyl]phenethyl]carbamoyl]-1-pyrrolidinecarboxylate as white crystals, melting point 173° (from methylene chloride/methanol/hexane);

From (S)-N-[(1S,2S,4S)-1-(cyclohexylmethyl)-2-hydroxy-4-isopropyl-5-hexenyl]-α-[(S)-α-(4-oxavaleramido)hydrocinnamamido]imidazole-4-propionamide, the (S)-N-[(1S,2S,4S)-1-(cyclohexylmethyl)-2-hydroxy-4-isopropylhexyl]-α-[(S)-α-4-oxovaleramido)hydrocinnamamido]imidazole-4-propionamide as a foam, MS: 638 (M+H)+;

From (S)-N-[(1S,2S,4S)-1-(cyclohexylmethyl)-2-hydroxy-4-isopropyl-5-hexenyl]-α-[(S) -α-(4-hydroxyhydrocinnamamido)hydrocinnamamido]-imidazole-4-propionamide, the (S)-N-[(1S,2S,4S)-1-(cyclohexylmethyl)-2-hydroxy-4-isopropylhexyl]-α-[(S)-α-(4-hydroxyhydrocinnamamido)hydrocinnamamido]imidazole-4-propionamide as a white solid, melting point 120° (dec.; from methylene chloride/ether/hexane);

From (S)-[(1S,2S,4S)-1-(cyclohexylmethyl)-2-hydroxy-4-isopropyl-5-hexenyl]-α-[(S)-α-(3-pyridineacrylamido)hydrocinnamamido]imidazole-4-propionamide, the (S)-N-[(1S,2S,4S)-1-(cyclohexylmethyl)-2-hydroxy-4-isopropylhexyl]-α-[(S)-α-[3-(3-pyridyl)propionamido]hydrocinnamamido]-imidazole-4-propionamide as white crystals, melting point 195° (from methanol/ether/hexane);

From (S)-N-[(1S,2S,4S)-1-(cyclohexylmethyl)-2-hydroxy-4-isopropyl-5-hexenyl[-α-[(S)-α-nicotinamidohydrocinnamamido]imidazole-4-propionamide, the N-[(S)-α-[[(S)-1-[[(1S,2S,4S)-1-(cyclohexylmethyl)-2-hydroxy-4-isopropylhexyl]-carbamoyl]-2-imidazol-4-ylethyl]carbamoyl]-phenethyl]nicotinamide as a white solid, melting point 112° (dec.; from methylene chloride/ether/hexane);

From (S)-N-[(1S,2S,4S)-1-(cyclohexylmethyl)-2-hydroxy-4-isopropyl-5-hexenyl]-α-[(S)-α-(imidazol-4-acrylamido)hydrocinnamamido]imidazole-4-propionamide, the N-[(1S,2S,4S)-1-(cyclohexylmethyl)-2-hydroxy-4-isopropyl]-α-[(S)-α-imidazole-4-propionamidohydrocinnamamido]-imidazole-4-propionamide as white crystals, melting point 118° (from methanol/ether/hexane);

From t-butyl [1-[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]phenethyl]-carbamoyl]-1-methylethyl] carbamate, the t-butyl [1-[[(S)-α-[[(S)-1-[[(1S,2S,4S)-1-(cyclohexylmethyl)-2-hydroxy-4-isopropylhexyl]carbamoyl]-2-imidazol 4-ylethyl]-carbamoyl]hydrocinnamoyl]carbamoyl]-1-methylethyl] carbamate as a foam, MS; 725 (M+H)+.

EXAMPLE 17

A mixture of 95 mg (0.133 mmol) of N-[(1S,2S,4S)-1-(cyclohexylmethyl)-2-hydroxy-4-isopropylhexyl]-α-[(3-phenyl-N-D-prolyl-L-alanyl)amino]imidazole-4-propionamide, 0.025 ml (0.199 mmol) of pivaloyl chloride and 0.185 ml (1.33 mmol) of triethylamine in 10 ml of tetrahydrofuran was stirred at room temperature overnight. After the usual working-up and chromatographic purification on silica gel with a 20:1:0.1 mixture of methylene chloride, methanol and ammonia, there was obtained (S)-N-[(1S,2S,4S)-1-(cyclohexylmethyl)-2-hydroxy-4-isopropylhexyl]-α-[(S)-α-[(R)-1-pivaloyl-2-piperidinecarboxamido]hydrocinnamamido]-imidazole-4-propionamide as a thin-layer chromatographically uniform solid, MS: 722 (M+H)+.

EXAMPLE 18

20 mg of (S)-α-[[N-(3-t-butoxy-L-alanyl)-3-phenyl-L-alanyl]amino]-N-[(1S,4S)-1-(cyclohexylmethyl)-2-hydroxy-4-isopropyl-5-hexenyl]imidazole-propionamide were dissolved in 1 ml of aqueous trifluoroacetic acid (95%) and stirred at room temperature for 2.5 hours. Evaporation of the reaction mixture and chromatographic purification on silica gel with a 8:1:0.1 mixture of methylene chloride, methanol and ammonia yielded thin-layer chromatographically uniform (S)-N-[(1S,2S,4S)-1-(cyclohexylmethyl)-2-hydroxy-4-isopropyl-5-hexenyl]-α-[[N-(L-serylamino)-3-phenyl-L-alanyl]amino]imidazole-4-propionamide, MS: 625 (M+H)+.

EXAMPLE 19

195 mg of N-[(R)-2-benzyl-5,5-dimethyl-4-oxohexanoyl]-N-methyl-L-histidine benzyl ester were hydrogenated in the presence of 25 mg of palladium-on-carbon (5%) for 2 hours and the N-[(R)-2-benzyl-5,5-dimethyl-4-oxohexanoyl]-N-methyl-L-histidine obtained was reacted in the usual manner with (αS,βS)-β-amino-α-[(S)-2-isopropyl-3-butenyl]cyclohexanepropanol. Chromatographic purification of the crude product obtained on silica gel with a 140:10:0.1 mixture of methylene chloride, methanol and ammonia yielded N-[(1S,2S,4S)-1-(cyclohexylmethyl)-2-hydroxy-4-isopropyl-5-hexenyl]-α-[(R)-2-benzyl-N,5,5-trimethyl-4-oxohexanamido]imidazole-4-propionamide as a thin-layer chromatographically uniform substance, MS: 635 (M+H)+.

The less polar epimeric N-[(1S,2S,4S)-1-(cyclohexylmethyl)-2-hydroxy-4-isopropyl-5-hexenyl]-α-[(R)-2-benzyl-N,5,5-trimethyl-4-oxohexanamido]imidazole-4-propionamide, MS: 635 (M+H)+, wis obtained as a byproduct.

The N-[(R)-2-benzyl-5,5-dimethyl-4-oxohexanoyl]-N-methyl-L-histidine benzyl ester used as the starting material was prepared by condensing N-(α-methyl)-L-histidine benzyl ester with 2-(R)-benzyl-4-oxo-5,5,5-trimethylvaleric acid and was used directly in the next step.

EXAMPLE 20

100 mg (0.164 mmol) of ethyl (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyrate were stirred at room temperature for 3 hours in a solution of 30% hydrazine hydrate in methanol. Thereafter, the reaction mixture was evaporated and the residue was chromatographed on silica gel with a 14:1:0.1 mixture of methylene chloride, methanol and ammonia. Crystallization of the crude product from methanol/methylene chloride/ether yielded (R)-3-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]4-phenylbutyrohydrazide as white crystals, melting point 109°.

The ethyl (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyrate used as the starting material was prepared as described in Example 40.

EXAMPLE 21

0.083 ml (0.54 mmol) of 4-piperidinecarboxylic acid ethyl ester was reacted at room temperature with 210 mg (0.36 mmol) of ethyl 1-[(R)-3-[[(S)-1-[[(1S,2S,4S)-1-(cyclohexylmethyl)-2-hydroxy-4-isopropyl-5-hexenyl]carbamoyl]-2-imidazol-4-yl-ylethyl]carbamoyl]-4-phenylbutyryl]carboxylate in 20 ml of acetonitrile in the presence of bis-(2-oxo-3-oxazolidinyl)phosphine chloride. After working-up in the usual manner and chromatography on silica gel, there was obtained ethyl 1-[(R)--3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyryl]-4-piperidinecarboxylate as a foam, MS: 720 (M+H)+.

The following compounds were prepared in a manner analogous to that described above:

From (R)-3-[[(S)-1-[[(1S,2S,4S)-1-(cyclohexylmethyl-2-hydroxy-4-isopropyl-5-hexenyl]carbamoyl]-2-imidazol-4-ylethyl]carbamoyl]-4-phenylbutyric acid and L-prolinol, the (S)-N-[(1S,2S,4S)-1-(cyclohexylmethyl)-2-hydroxy-4-isopropyl-5-hexenyl]-α-[(R)-α-[[(2-hydroxymethyl)-1-pyrrolidinyl]carbonyl]methyl]hydrocinnamamido]-imidazole-4-propionamide as a white solid, melting point 103° (dec.; from methylene chloride/ether/hexane);

From (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyric acid and N-methylethanolamine, the (S)-N-[(1S,2S,4S)-1-(cyclohexylmethyl)-2-hydroxy-4-isopropyl-5-hexenyl]-α-[(R)-α-[[(2-hydroxyethyl)methylcarbamoyl]methyl]-hydrocinnamamido]-imidazole-4-propionamide as a white solid, melting point 82° (dec.; from methylene chloride/ether/hexane);

From (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyric acid and N,N-dimethylethylenediamine, the (S)-N-[(1S,2S,4S)-1-(cyclohexylmethyl)-2-hydroxy-4-isopropyl-5-hexenyl]-α-[(R)-α-[[[2-(dimethylamino)ethyl]carbamoyl]methyl]hydrocinnamamido]-imidazole-4-propionamide as a white solid, melting point 98° (from methylene chloride/hexane);

From (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyric acid and N,N-dimethylpropylenediamine, the (S)-N-[(1S,2S,4S)-1-(cyclohexylmethyl)-2-hydroxy-4-isopropyl-5-hexenyl]-α-[(R)-α-[[[3-(dimethylamino)propyl]carbamoyl]methyl]hydrocinnamamido]-imidazole-4-propionamide as white crystals, melting point 98° (from methylene chloride/ether).

The (R)-3-[[(S)-1-[[(1S 2S,4S)-1-(cyclohexylmethyl)-2-hydroxy-4-isopropyl-5-hexenyl]carbamoyl]-2-imidazol-4-ylethyl]carbamoyl]-4-phenylbutyric acid used as the starting material was prepared as follows:

100 mg (0.16 mmol) of ethyl (R)-3-[[(S)-1-[[(1S,2S,4S)-1-cyclohexylmethyl)-2-hydroxy-4-isopropyl-5-hexenyl]carbamoyl]-2-imidazol-4-ylethyl]carbamoyl]-4-phenylbutyrate (see Example 40) in 3 ml of ethanol were treated with 0.66 ml of 0.5N (0.33 mmol) sodium hydroxide solution and stirred at room temperature for 2.5 hours. The mixture was then neutralized with 0.33 ml (0.33 mmol) of 1N hydrochloric acid, ethyl acetate was added thereto and the mixture was washed with saturated sodium chloride solution. The organic phase was then dried over sodium sulfate and the solvent was removed under reduced pressure, to obtain 91 mg (95%) of (R)-3-[[(S)-1-[[(1S,2S,4S)-1-(cyclohexylmethyl)-2-hydroxy-4-isopropyl-5-hexenyl]carbamoyl]-2-imidazol-4 -ylethyl]-carbamoyl]-4-phenylbutyric acid as an amorphous powder. MS: 581 (M+H)+.

EXAMPLE 22

70 mg (0.1 mmol) of ethyl 1-[(R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyryl]-4-piperidinecarboxylate were suspended in 1N sodium hydroxide solution in a 9:1 mixture of methanol and water and stirred at room temperature for 3 hours. Thereafter, the solvent was evaporated and the residue was recrystallized from methanol/methylene chloride/hexane, to obtain 1-[(-R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyryl]-4-piperidinecarboxylic acid as white crystals, melting point 169°.

EXAMPLE 23

Reaction of (S)-N-[(1S,2S,4S)-1-(cyclohexylmethyl)-2-hydroxy-4-isopropyl-5-hexenyl]-α-[(S)-α-(D-prolylamino)hydrocinnamamido]imidazole-4-propionamide dihydrochloride (see Example 8) with Fmoc-Ser(t-Bu)OH in manner analogous to that described in Example 1, treatment of the Fmoc-protected compound obtained with piperidine and subsequent chromatography of the crude product on silica gel with a 200:10:1 mixture of methylene chloride, methanol and ammonia yielded thin-layer chromatographically pure (S)-α-[[N-[1-(3-butoxy-L-alanyl)-D-propyl]-3-phenyl-D-alanyl-]amino]-N-[(2S,3S,4S)-3-(cyclohexylmethyl)-2-hydroxy-4-isopropyl-5-hexenyl]-imidazole-4-propionamide as a foam, MS: 779 (M+H)+.

EXAMPLE 24

A mixture of 100 mg (0.17 mmol) of 2-t-butyl [(S)-α-[[(S)-1-[[(1S,2S,4S)-2-hydroxy-1-isobutyl-4-isopropyl-5-hexenyl]carbamoyl]-2-imidazol-4-ylethyl]carbamoyl]-phenethyl] carbamate and 65 mg (0.25 mmol) of osmium tetroxide in 20 ml of pyridine was stirred at room temperature overnight. Thereafter, 4 ml of 33% sodium bisulphite solution were added and the mixture was stirred for a further hour. Chromatography of the crude product, obtained after the usual working-up, on 20 g of silica gel with a 9:1:0.1 mixture of chloroform, methanol and ammonia yielded 65 mg of thin-layer chromatoqraphically uniform (2RS,3S,5S,6S)-6-(Boc-Phe-His-NH)-3-isopropyl-8-methyl-1,2,5-nonanetriol, MS: 632 (M+H)+.

EXAMPLE 25

A mixture of 411 mg (0.82 mmol) of (RS)-α-[[(S)-α-(Boc-Pro-NH)phenethyl]carbamoyl]imidazole-4-propionic acid, 200 mg (0.82 mmol) of (αS,βS)-β-amino-α-[(S)-2-isopropyl-3-butenyl]cyclohexanepropanol, 0.1 ml (0.82 mmol) of 4-ethylmorpholine ,222 mg (1.64 mmol) of HOBT and 203 mg (0.99 mmol) of DCC was dissolved in 20 ml of dimethylformamide and stirred at room temperature for 2 days. The separated precipitate was filtered off and the solvent was evaporated under reduced pressure. After the usual working-up, there were obtained 590 mg of a crude product which was chromatographed on 30 g of silica gel with a 20:1:0.1 mixture of methylene chloride, methanol and ammonia. Recrystallization of the thin-layer chromatographically uniform product from methylene chloride/ether/hexane yielded 260 mg of t-butyl (S)-2-[[(S)-α-[(RS)-α-[[(1S,2S,4S)-1 -(cyclohexylmethyl-2-hydroxy-4-isopropyl-5-hexenyl]carbamoyl]imidazole-3-propionamido]-phenethyl]carbamoyl]-1-pyrrolidinecarboxylate as crystals, melting point 112°.

The (RS)-α-[[(S)-α-(Boc-Pro-NH)phenethyl]-carbamoyl]imidazole-4-propionic acid used as the starting material was prepared as follows:

10 8 g (30 mmol) of Boc-Pro-Phe-OH and 3.0 g (30 mmol) of N-methylmorpholine were dissolved in 120 ml of tetrahydrofuran and cooled to −20°. 4.1 g of isobutyl chloroformate in 15 ml of tetrahydrofuran were added dropwise to this solution and after 5 minutes at −20° a solution of 3.9 g (60 mmol) of sodium azide in 30 ml of water was added dropwise. After completion of the addition, the mixture was stirred at 0° for 30 minutes, then diluted with ice-cold ethyl acetate to double the volume, and the reaction mixture was subsequently treated with cold saturated sodium bicarbonate solution and then with cold saturated sodium chloride solution. The organic phase separated, dried over magnesium sulphate and evaporated under reduced pressure at a temperature of 20°-25°. The residue was dissolved in 300 ml of toluene under a nitrogen atmosphere and heated to 80° . Then. 4.9 g (45 mmol, 1.5 mol equivalents) of benzyl alcohol were added and the reaction mixture was heated to reflux for 6 hours. After cooling and evaporating the reaction solution, the residue was triturated with a 1:1 mixture of ether and hexane and the separated precipitate was filtered off. After drying the filtrate under reduced pressure, there were obtained 11 g (79%) of [(R)-1-(Boc-Pro-NH)-1-(benzylamino)ethyl]- benzene, melting point 155°-157°.

4.7 g (10 mmol) of the above compound in 300 ml of tetrahydrofuran were hydrogenated for 3 hours in the presence of 1.0 g of palladium-on-carbon at 343.25 kPa. After completion of the hydrogen uptake, the catalyst was filtered off and the filtrate was evaporated under reduced pressure. The residue was dissolved in 60 ml of dimethyl formamide and 1.98 g (10 mmol) of (RS)-(imidazol-4-ylmethyl)malonic acid monomethyl ester[4]. The solution obtained was then cooled to 0° and treated with 3.0 g (20 mmol) of HOBT and 2.2 g (12 mmol) of EDC. The reaction mixture was then left to warm to room temperature and stirred at this temperature for 48 hours. After evaporating the reaction mixture in a high vacuum, the residue was dissolved in ethyl acetate, washed with water and subsequently extracted with 1N citric acid. The citric acid extract was neutralized with sodium bicarbonate and extracted with ethyl acetate. The organic extract was then dried over sodium sulfate and evaporated under reduced pressure. Chromatography of the residue on silica gel and recrystallization of the crude product obtained from ethyl acetate/ether yielded 2.5 g (49%) of (RS)-α-[[(S)-α-(Boc-Pro-NH)-phenethyl]carbamoyl]-imidazole-4-propionic acid methyl ester, melting point 142°–143°.

[4] M. Goodman et al., Int. J. Pept. Prot. Res. 17, 72–88 (1981)

1.54 g (3 mmol) of the above ester were dissolved in 6 ml of ethanol and treated with 3.15 ml (3.15 mmol, 1.05 mol equivalents) of 1N sodium hydroxide solution. After stirring for 3 hours while cooling with ice, 3.15 ml (3.15 mmol) of 1N $H_2SO_4$ were added and the reaction mixture was evaporated under reduced pressure. The residue was triturated with 300 ml of ethanol and the insoluble sodium sulfate was filtered off. Concentration of the ethanolic solution yielded 1.47 g (98%) of (RS)-α-[[(S)-α-(Boc-Pro-NH)phenethyl]carbamoyl]imidazole-4-propionic acid, melting point 120° (dec.).

EXAMPLE 26

A mixture of 1.05 g (2.06 mmol) of Boc-Phe[R]His(Bom)-OH, 0.5 g (2.06 mmol) of (αS,βS)-β-amino-α-[(S)-2-isopropyl-3-butenyl]cyclohexanepropanol. 0.26 ml (2.06 mmol) of 4-ethylmorpholine, 0.56 g (4.12 mmol) of HOBT and 0.51 g (2.47 mmol) of DCC in 40 ml of dimethylformamide was stirred at room temperature overnight. Separated urea was then filtered off and the solvent was evaporated under reduced pressure. Working-up of the residue in the usual manner yielded 1.69 g of t-butyl [(S)-1-benzyl-2-[[(S)-1-[[(1S,2S,4S)-1-(cyclohexylmethyl)-2-hydroxy-4-isopropyl-5-hexenyl]-carbamoyl]-2-imidazol-4-ylethyl]amino]ethyl]carbamate, which was used directly in the next step.

1.69 g (about 2.06 mmol) of t-butyl [(S)-1-benzyl-2-[[(S)-1-[[(1S,2S,4S)-1-(cyclohexylmethyl)-2-hydroxy-4-isopropyl-4-hexenyl]carbamoyl]-2-imidazol-4-ylethyl]amino]-ethyl] carbamate were hydrogenated at room temperature overnight in the presence of 0.5 g of palladium-on-carbon (5%) in 50 ml of a 4:1 mixture of acetic acid and water and 0.8 g of N,N'-dimethylethylenediamine. After completion of the hydrogen uptake, the catalyst was filtered off and the filtrate was evaporated and treated twice in succession with toluene and then again evaporated to dryness. Chromatography of the residue on 180 g of silica gel with a 20:1:0.1 mixture of methylene chloride, methanol and ammonia as the eluting agent yielded 1.13 g of a crude product which was recrystallized from methylene chloride/ether/hexane, to obtain 730 mg of t-butyl [(S)-1-benzyl-2-[[(S)-1-[[(1S,2S,4S)-1-(cyclohexylmethyl)-2-hydroxy-4-isopropylhexyl]carbamoyl]-2-imidazol-4-ylethyl]amino]ethyl]carbamate as crystals, melting point 144°.

The Boc-phe[R]His(Bom)OH, used as the starting material was prepared as follows:

58 g of Boc-Phe-His(Bom)OMe, which was prepared by coupling Boc-Phe-OH with His(Bom)OMe according to usual methods. 30.35 g of Lawesson reagent and 700 ml of benzene were heated to reflux overnight. Thereafter, the reaction mixture was cooled and evaporated to dryness. The residue was then filtered through 1.5 g of silica gel, first with methylene chloride and then with methylene chloride, with the progressive addition of ethanol (up to 7%). There were thus obtained 35.56 g of [(S)-2-(Boc-NH)-3-phenylthiopropionyl]His(Bom)OMe in the form of a foam, MS: 553 (M+H)+.

0.5 g of the above thio compound and 5 g of Raney-nickel in 30 ml of ethanol were stirred in a hydrogen atmosphere for 2 hours. The catalyst was then filtered off and the filtrate was evaporated. Chromatography of the crude product on 30 g of silica gel with chloroform, a 98:2 mixture of chloroform and ethanol and a 95:5 mixture of chloroform and ethanol as the eluting agent yielded 0.24 g of [(S)-2-(Boc-NH)-3-phenylpropyl]His(Bom)OMe in the form of a foam, MS; 523 (M+H)+.

170 mg of the above ester in 2 ml of 1N sodium hydroxide solution in a 1:1 mixture of methanol and water were stirred at room temperature overnight. 1 ml of conc. acetic acid was then added and the reaction mixture was evaporated under reduced pressure. The residue was warmed three times with 150 ml of methanol each time and decanted off. The methanolic phase was evaporated and the residue was chromatographed on 30 g of silica gel with a 4:1:1 mixture of butanol, acetic acid and water, to obtain 100 mg of [(S)-2-(Boc-NH)-3-phenylpropyl]-His(Bom)OH in form of a foam, MS: 509 (M+H)+.

EXAMPLE 27

0.17 g (0.56 mmol) of 2-(RS)-benzyl-4-(4-chlorophenyl)-4-oxo-butyric acid was dissolved in 10 ml of dimethylformamide and treated with 0.20 g (0.51 mmol) of (S)-α-amino-N-[(1S,2S,4S)-1-(cyclohexylmethyl)-2-hydroxy-4-isopropyl-5-hexenyl]imidazole-4-propionamide, 0.057 g (0.56 mmol) of triethylamine and 0.21 g (0.56 mmol) of HBTU and stirred at room temperature overnight. The mixture was subsequently evaporated in a high vacuum. The residue was dissolved in ethyl acetate and then washed with saturated sodium bicarbonate solution and saturated sodium chloride solution. After drying the organic phase over sodium sulfate, the solvent was evaporated under reduced pressure and the residue, for purification, was chromatographed on silica gel using a 95:5 mixture of methylene chloride and methanol which contained 0.5% ammonium hydroxide. There were obtained 270 mg (78%) of (S)-α-[(RS)-α-(4-chlorophenylacetyl)hydrocinnamamido]-N-[(1S,2S,4S)-1-(cyclohexylmethyl)-2-hydroxy-4-isopropyl-5-hexenyl]imidazole-4-propionamide in the form of a yellowish foam. MS: 675 (M+).

The 2-(RS)-benzyl-4-(4-chlorophenyl)-4-oxo-butyric acid used as the starting material was prepared as follows:

5.0 g (20 mmol) of benzylmalonic acid diethyl ester were added dropwise at room temperature to a suspension of 0.87 g of sodium hydride dispersion (55% in oil) in 20 ml of dimethylformamide. Subsequently, the reaction mixture was stirred at room temperature for 20 minutes and thereafter 4.67 g (20 mmol) of omega-bromo-4-chloroacetophenone in 25 ml of dimethylformamide were added dropwise. After completion of the addition, the deep brown colored reaction mixture was stirred at room temperature overnight and thereafter evaporated in a high vacuum. The residue was dissolved in methylene chloride, washed with water and dried over sodium sulfate. Thereafter, the solvent was evaporated under reduced pressure and the residue, for purification, was chromatographed on silica gel with a 6:1 mixture of hexane and ether, to obtain 5.17 g (64%)

of 2-(RS)-benzyl-2-carbethoxy-4-(4-chloro-phenyl)-4-oxobutyric acid as a yellowish solid. MS: 357 (M-OC$_2$H$_5$)$^+$, 311 (M-benzyl)$^+$.

6.15 ml (3 mol equivalents) of 2N sodium hydroxide solution were added to a solution of 1.64 g (4.1 mmol) of the above-named ethyl ester in 10 ml of ethanol and 9 ml of water, and the reaction mixture was stirred at room temperature for 16 hours. The mixture was subsequently adjusted to pH 3 with 1N hydrochloric acid and extracted with methylene chloride. The organic phase was dried over sodium sulfate, evaporated under reduced pressure and the crystalline residue was heated to 150°–160° until CO$_2$ evolution had terminated. After cooling, the residue was dissolved in ether and brought to crystallization by the addition of hexane. There was thus obtained 970 mg (79%) of 2-(RS)-benzyl-4-(4-chlorophenyl)-4-oxobutyric acid as yellowish crystals, melting point 137°–138°.

EXAMPLE 28

1.57 g (4.03 mmol) of (S)-α-amino-N-[(1S,2S,4S)-1-(cyclohexylmethyl)-2-hydroxy-4-isopropyl-5-hexenyl]imidazole-4-propionamide, 0.45 g (4.43 mmol) of triethylamine and 1.68 g (4.43 mmol) of HBTU were added to a solution of 1.45 g (4.43 mmol) of 2-(RS)-(1-naphthylmethyl)-3-morpholinocarbonylpropionic acid[5] in 60 ml of dimethylformamide. The yellow reaction solution obtained was then stirred at room temperature for 15 hours and subsequently evaporated in a high vacuum. The residue was dissolved in 150 ml of methylene chloride, the organic phase was washed twice with 30 ml of saturated sodium bicarbonate solution and 30 ml of water, dried over sodium sulfate and evaporated under reduced pressure. For purification and separation of the two epimers, the residue was chromatographed on silica gel with a 95:5 mixture of methylene chloride and methanol which contained 0.5% ammonium hydroxide. There was thus obtained 855 mg (30%) of an isomer with the Rf value 0.45 and 726 mg (26%) of an isomer with the Rf value 0.33. Both isomers exhibited the same mass spectrum, MS: 700 (M+H)$^+$.
[5] EPA 0.200.406

The 2-(RS)-(1-naphthylmethyl)-3-morpholinocarbonylpropionic acid used as the starting material was prepared as follows:

1.10 g (12.6 mmol) of morpholine, 2.42 g (12.6 mmol) of EDC and 3.43 g (25.2 mmol) of HOBT were added to a solution of 3.63 g (12.6 mmol) of 3-ethoxycarbonyl-4-(1-naphthyl)butyric acid[6] in 50 ml of dimethylformamide, and the reaction solution was stirred at room temperature for 15 hours and subsequently evaporated in a high vacuum. The residue was dissolved in ethyl acetate and the organic phase was washed with water, saturated sodium bicarbonate solution and saturated sodium chloride solution, dried over sodium sulfate and evaporated under reduced pressure. The residue was chromatographed on silica gel with a 98:2 mixture of methylene chloride and ethanol, to obtain 3.78 g (84%) of 2-(RS)-(1-naphthylmethyl)-3-morpholinocarbonylpropionic acid ethyl ester as a yellowish oil which began to crystallize out after lengthy standing. MS: 355 (M+).
[6] EPA 0.181.110

1.7 g (4.78 mmol) of the above-named ethyl ester were dissolved in 6 ml of ethanol and, after the addition of 7.2 ml (7.2 mmol) of 1N sodium hydroxide solution, stirred at 50° for 3 hours. After cooling, 7.5 ml (7.5 mmol) of 1N hydrochloric acid were added to the deep yellow reaction solution and the mixture was subsequently evaporated under reduced pressure. The residue was dissolved in 100 ml of methylene chloride and the organic phase was washed twice with 20 ml of water, dried over sodium sulfate and evaporated under reduced pressure, to obtain 1.45 g (92%) of 2-(RS)-(1-naphthylmethyl)-3-morpholinocarbonylpropionic acid as a yellow foam which was used directly in the next step. MS: 327 (M+).

EXAMPLE 29

109 mg (0.38 mmol) of 3-(RS)-(1-naphthylmethyl)succinic acid 1-ethyl ester were dissolved in 6 ml of acetonitrile and 1 ml of dimethylformamide and, after the addition of 135 mg (0.35 mmol) of (S)-α-amino-N-[(1S,2S,4S)-1-(cyclohexylmethyl)-2-hydroxy-4-isopropyl-5-hexenyl]imidazole-4-propionamide, 39 mg (0.38 mmol) of triethylamine and 144 mg (0.38 mmol) of HBTU, stirred at room temperature for 6 hours. Subsequently, the reaction solution was evaporated in a high vacuum and the residue was dissolved in 50 ml of ethyl acetate and washed 3 times with 10 ml of saturated sodium bicarbonate solution. The organic phase was dried over sodium sulfate and evaporated under reduced pressure, and the residue was chromatographed on silica gel with a 95:5 mixture of methylene chloride and methanol which contained 0.1% ammonium hydroxide, to obtain 103 mg (45%) of (RS)-β-[[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]-1-naphthylbutyric acid ethyl ester as a yellowish foam. MS: 594 (M-ethanol-water)$^+$ The 3-(RS)-(1-naphthylmethyl)succinic acid 1-ethyl ester used as the starting material was prepared as follows:

820 mg (3.44 mmol) of 2-(1-naphthylmethylene)succinic acid anhydride[6] were heated to reflux for 4 hours in 5 ml of ethanol. Subsequently, the reaction mixture was evaporated under reduced pressure, the residue was taken up in 10 ml of saturated sodium bicarbonate solution and extracted with ether. The aqueous phase was acidified with 1N hydrochloric acid and extracted with ether. After drying the ether extract over sodium sulfate and evaporation under reduced pressure, there remained 710 mg (73%) of 3-(RS)-(1-naphthylmethylene)succinic acid 1-ethyl ester.
[6] pA 0.181.110

These 710 mg (2.5 mmol) of ethyl ester were dissolved in 5 ml of ethanol and hydrogenated for 15 hours in the presence of 100 mg of palladium-on-carbon. Thereafter, the catalyst was filtered off, the filtrate was evaporated under reduced pressure and the residue was chromatographed on silica gel with a 98:2 mixture of methylene chloride and methanol, to obtain 190 mg (27%) of 3-(RS)-(1-naphthylmethyl)succinic acid 1-ethyl ester. MS: 286 (M)$^+$

EXAMPLE 30

In a manner analogous to that described in Example 27, by condensing (αRS,S)-α-benzyl-1-t-butoxycarbonyl-γ-oxo-2-pyrrolidinebutyric acid with (S)-α-amino-N-[(1S,2S,4S)-1-(cyclohexylmethyl)-2-hydroxy-4-isopropyl-5-hexenyl]imidazole-4-propionamide and subsequent epimer separation by chromatography, there were obtained t-butyl (S)-2-[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-phenethyl]acetyl]-1-pyrrolidinecarboxylate (less polar isomer) and t-butyl (S)-2-[[(R)-γ-[[(S)-1-[[(1S,2S,4S)-1-(cyclohexylmethyl)-2-hydroxy-4-isopropyl-5-hexenyl]- carbamoyl]-2-imidazol-4-ylethyl]carbamoyl]phenethyl]acetyl]-1-pyrrolidinecarboxylate. MS: 734 (M+H)+

The (αRS,S)-α-benzyl-1-t-butoxycarbonyl-γ-oxo-2-pyrrolidinebutyric acid used as the starting material was obtained from N-t-butoxycarbonyl-prolyl-bromomethane[7] and benzylmalonic acid diethyl ester in analogy to the preparation of 2-(RS)-benzyl-4-(4-chlorophenyl)-4-oxobutyric acid (see Example 27), MS: 362 (M+H)+.

[7] EPA 0.029.163

EXAMPLE 31

In a manner analogous to that described in Example 2, by catalytically hydrogenating t-butyl (S)-2-[[(S)-α-[-[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]-phenethyl]acetyl]-1-pyrrolidinecarboxylate and t-butyl (S)-2-[[(R)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl]acetyl]-1-pyrrolidinecarboxylate, there was obtained t-butyl (S)-2-[[(S)-α-[[(S)-1-[[(1S,2S,4S)-1-(cyclohexylmethyl)-2-hydroxy-4-isopropylhexyl]carbamoyl]-2-imidazol-4-ylethyl]-carbamoyl]phenethyl]acetyl]-1-pyrrolidinecarboxylate (less polar isomer) and t-butyl (S)--2-[[(R)-α-[[(S)-1-[[(1S,2S,4S)-1-(cyclohexylmethyl)-2--hydroxy-4-isopropylhexyl]carbamoyl]-2-imidazol-4-ylethyl]carbamoyl]phenethyl]-acetyl]-1-pyrrolidinecarboxylate. MS: 736 (M+H)+

EXAMPLE 32

In a manner analogous to that described in Example 1, 1-[1-[(RS)-3-[[(S)-1-[[(1S,2S,4S)-1(cyclohexylmethyl)-2-hydroxy-4-isopropylhexyl]carbamoyl]2-imidazol-4-yl-ethyl]-carbamoyl]-4-phenybutyryl]-D-prolyl]-L-proline benzyl ester was prepared as a mixture of 2 epimers by condensing (S)-α-amino-N-[(1S,2S,4S)-1-(cyclohexylmethyl)-2-hydroxy-4-isopropylhexyl]imidazole-4-propionamide with (αRS,2R)-α-benzyl-2-[[(S)-2-[(benzyloxy)carbonyl]-1-pyrrolidinyl]carbonyl]-γ-oxo-1-pyrrolidinebutyric acid. MS: 867 (M+H)+

The acid used as the starting material was prepared as follows:

2-Benzyl-3-methoxycarbonylpropionic acid t-butyl ester, MS: 222 (M-C4H8)+, was prepared starting from 2-benzyl-3-methoxycarbonylpropionic acid[8] according to the procedure described by U. Widmer in Synthesis 1983, page 135.

[8] L. D. Byers and R. Wolfenden, J. Biol. Chem., 247, 606 (1972).

415 mg of the above t-butyl ester were dissolved in 3 ml of t-butyl alcohol and stirred at room temperature for 3 hours in the presence of 1.5 ml of 1N sodium hydroxide solution. The reaction solution was then evaporated under reduced pressure and the residue was dissolved in water and washed with ether. The aqueous phase was thereafter neutralized with 1.5 ml of 1N hydrochloric acid and extracted with methylene chloride. The organic extracts were dried over sodium sulfate and evaporated under reduced pressure, to obtain 2-benzyl-3-carboxypropionic acid t-butyl ester as a colorless oil, MS: 208 (M-C4H8)+.

370 mg (1.4 mmol) of the above-named half ester, 409 mg (1.2 mmol) of H-D-Pro-Pro-OBz and 270 mg (2 mol equivalents) of triethylamine were dissolved in 8 ml of dimethylformamide. 530 mg (1.4 mmol) of HBTU were added to this solution and the reaction mixture was stirred at room temperature for 15 hours and subsequently evaporated to dryness in a high vacuum. The residue was dissolved in ethyl acetate and washed with saturated sodium bicarbonate solution. The organic phase was dried over sodium sulfate and evaporated under reduced pressure. Chromatography of the residue on silica gel with a 98:2 mixture of methylene chloride and methanol yielded (αRS,2R)-α-benzyl-2-[[(S)-2-[(benzyloxy)carbonyl]-1-pyrrolidinyl]carbonyl]-γ-oxo-1-pyrrolidinebutyric acid t-butyl ester as a colorless foam. MS: 549 (M+H)+.

505 mg (0.9 mmol) of the above t-butyl ester were stirred at room temperature for 3 hours in 10 ml of 2N hydrochloric acid/acetic acid. Thereafter, the reaction mixture was evaporated under reduced pressure, to obtain (αRS,2R)-α-benzyl-2-[[(S)-2-[(benzyloxy)carbonyl]-1-pyrrolidinyl]carbonyl]-γ-oxo-1-pyrrolidinebutyric acid as a colorless foam. MS: 493 (M+H)+.

The (S)-α-amino-N-[(1S,2S,4S)-1-(cyclohexylmethyl)-2-hydroxy-4-isopropylhexyl]imidazole-4-propionamide used as the starting material was prepared as follows:

50 mg of (S)-α-amino-N-[(1S,2S,4S)-1-(cyclohexylmethyl)-2-hydroxy-4-isopropyl-5-hexenyl]imidazole-4-propionamide were dissolved in 3 ml of methanol and hydrogenated at room temperature for 3 hours at normal pressure in the presence of 7 mg of palladium-on-carbon. Thereafter, the catalyst was filtered off and rinsed with methanol. The alcoholic solution was then evaporated under reduced pressure, to obtain (S)-α-amino-N-[(1S,2S,4S)-1-(cyclohexylmethyl)-2-hydroxy-4-isopropylhexyl]imidazole-4-propionamide as a colorless foam. MS: 393 (M+H)+.

EXAMPLE 33

The following compounds were prepared in a manner analogous to that described in Example 1:

From (S)-α-amino-N-[(1S,2S,4S)-1-(cyclohexylmethyl)-2-hydroxy-4-isopropyl-5-hexenyl]imidazole-4-propionamide and (αRS,2R)-α-benzyl-2-[[(S)-2-[(benzyloxy)carbonyl]-1-pyrrolidinyl]-carbonyl]-γ-oxo-1-pyrrolidinebutyric acid, the 1-[1-[(RS)-3-[[(S)-1-[[(1S,2S,4S)-1(cyclohexylmethyl)-2-hydroxy-4-isopropyl-5-hexenyl]carbamoyl]-2-imidazol-4-ylethyl]carbamoyl]-4-phenylbutyryl]-D-prolyl]-L-proline benzyl ester as a 1:1 epimer mixture, MS: 865 (M+H)+;

From (S)-α-amino-N-[(1S,2S,4S)-1-(cyclohexylmethyl)-2-hydroxy-4-isopropyl-5-hexenyl]-imidazole-4-propionamide and N-(t-butoxycarbonyl)-N-[2-[(RS)-3-carboxy-4-phenylbutyramido]ethyl]glycine t-butyl ester, the two epimeric compounds t-butoxycarbonyl [2-[(R and S)-α-[[(S)-1-[[(1S,2S,4S)-1-(cyclohexylmethyl)-2-hydroxy-4-isopropyl-5-hexenyl]carbamoyl]2-imidazol-4-ylethyl]carbamoyl]-4-phenylbutyramido]ethyl]-glycine t-butyl ester, MS: 837 (M+H)+;

From (S)-α-amino-N-[(1S,2S,4S)-1-(cyclohexylmethyl)-2-hydroxy-4-isopropyl-5-hexenyl]imidazole-4-propionamide and (R)-α-[[[2-hydroxy-1-(hydroxymethyl)-1-methyl]carbamoyl]methyl]hydrocinnamic acid, the (S)-N-[(1S,2S,4S)-1-(cyclohexylmethyl)-2-hydroxy-4-isopropyl-5-hexenyl]-α-[(R)-α-[[[2-hydroxy-1-(hydroxymethyl)-1-methylethyl]carbamoyl]methyl]hydrocinnamamido]imidazole-4-propionamide, MS: 668 (M+H)[30];

From (S)-α-amino-N-[(1S,2S,4S)-1-(cyclohexylmethyl)-2-hydroxy-4-isopropyl-5-hexenyl]imidazole-4-propionamide and 5-[(RS)-3-carboxy-4-phenylbutyramido]valeric acid t-butyl ester, the t-butyl 5-[(RS)-3-[[(S)-1-[[(1S,2S,4S)-1-(cyclohexyl-methyl)-2-hydroxy-4-isopropyl-5-hexenyl]carbamoyl]-2-imidazol- 4-ylethyl]carbamoyl]-4-phenylbutyramido]valerate, MS: 736 (M+H)+;

From (S)-α-amino-N-[(1S,2S,4S)-1(cyclohexylmethyl)-2-hydroxy 4-isopropyl 5-hexenyl]imidazole-4-propionamide and 3-carboxy-4-phenylbutyryl L-proline t-butyl ester, the 1-[(RS)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyryl]-L-proline t-butyl ester, MS: 734 (M+H)+;

From (S)-α-amino-N [(1S,2S,4S)-1(cyclohexylmethyl)-2-hydroxy-4-isopropyl-5-hexenyl]imidazole-4-propionamide and (RS) 2-benzylmalonic acid monomethyl ester[9], the methyl (RS)-α-[[(S)-1 -[[(1S,2S,4S)-1-(cyclohexylmethyl)-2-hydroxy-4-isopropyl-5-hexenyl]-carbamoyl]-2-imidazol-4-ylethyl]carbamoyl]hydrocinnamate as a 1:1 mixture of the two epimers, MS: 580 (M+);

[9] F: Texier et al., Tetrahedron, 1974, 3185,

From (S)-α-amino-N-[(1S,2S,4S)-1-(cyclohexylmethyl)-2-hydroxy-4-isopropyl 5-hexenyl]imidazole-4-propionamide and 3-(RS)-ethoxycarbonyl-4-(1 -naphthyl)butyric acid[6], the ethyl (RS)-α-[[[(S)-1-[[(1S,2S,4S)-1-(cyclohexylmethyl)-2-hydroxy-4-isopropyl-5-hexenyl]-carbamoyl]-2-imidazol-4-ylethyl]carbamoyl]methyl]- 1-naphthalenepropionate as a 1:1 mixture of the two epimers, MS 659 (M+H)+: ≠[6] EPA 0.181.110

From (S)-α-amino-N-[(1S,2S,4S)-1-(Cyclohexylmethyl)-2-hydroxy-4-isopropyl-5-hexenyl]-imidazole-4-propionamide and 2-(RS)-benzyl-3-morpholinocarbonylpropionic acid and subsequent chromatographic separation of the two epimers, the less polar (S)-N-[(1S,2S,4S)-1-(cyclohexylmethyl)-2-hydroxy-4-isopropyl-5-hexenyl]-α-[(S)-α-[(morpholinocarbonyl)methyl]-hydrocinnamamido]-imidazole-4-propionamide, MS: 650 (M+H)+, and the more polar (S)-N-[(1S,2S,4S)-1-(cyclohexylmethyl)-2-hydroxy-4-isopropyl-5-hexenyl]-α-[(R)-α-[(morpholinocarbonyl)methyl]-hydrocinnamamido]-imidazole-4-propionamide, MS: 650 (M+H)[30].

The acids used as starting materials were prepared as follows:

N-(t-Butoxycarbonyl)-N-[2-(RS)-3-carboxy-4-phenylbutyramidoethyl]glycine t-butyl ester 0.84 g (2.4 mmol) of N-(t-butoxycarbonyl)-N-(2-benzyloxycarbonylaminoethy)glycine[10] was suspended in 5 ml of toluene and heated to 80°. To the clear solution obtained in this matter there were added, dropwise within 20 minutes, 1.96 g of N,N-dimethylformamide di-t-butyl acetal. After completion of the addition, the reaction mixture was stirred at 80° for 30 minutes, then cooled and washed in succession with water, saturated sodium bicarbonate solution and saturated sodium chloride solution. The organic phase was then dried over sodium sulfate and evaporated under reduced pressure, to obtain N-(t-butoxy-carbonyl)-N-(2-benzyloxycarbonlaminoethyl)glycine t-butyl ester as a colorless oil, MS: 409 (M+H)[30]. [10] U.S. Pat. No. Specification 4,145,337

0.78 g (1.9 mmol) of N-(t-butoxycarbonyl)-N-(2-benzyloxycarbonylaminoethyl)glycine t-butyl ester was dissolved in 20 ml of methanol and hydrogenated at pH 4.5 in the presence of 0.1 g of palladium-on-carbon. The pH value was held constant by means of methanol/hydrochloric acid. After completion of the hydrogen uptake, the catalyst was filtered off, the filtrate was evaporated and the residue was dissolved in methylene chloride and washed with saturated sodium carbonate solution. After drying the organic phase over sodium sulfate and evaporation under reduced pressure, N-(t-butoxycarbonyl)-2-(2-aminoethyl)glycine t-butyl ester was obtained in the form of an oil. NMR (250 MHZ, TMS, CDCL3): δ1.44, 1.47 (2xs,18H) 2.83 (s,2H) 3.36 (s,2H), 3.79, 3.87 (2Xs,2H).

Condensation of 3-ethoxycarbonyl-4-phenylbutyric acid with N-(t-butoxycarbonyl)-2-(2-aminoethyl)glycine t-butyl ester yielded N-(t-butoxycarbonyl)-N-[2-[(RS)-3-(ethoxycarbonyl)-4-phenylbutyramido]ethyl]glycine t-butyl ester [MS: 492 (M)+] which, in turn, was hydrolyzed with 1N sodium hydroxide solution in ethanol at 50° to give the desired acid, N-(t-butoxycarbonyl)-N-[2-[(RS)-3-carboxy-4-phenylbutyramido]ethyl]glycine t-butyl ester, MS: 408 (M-C4H8)+.

(R)-α-[[[2-Hydroxy-1-(hydroxymethyl)-1-methyl]carbamoyl]methyl]hydrocinnamic acid 3-Ethoxycarbonyl-4-phenylbutyric acid [11] and 2-amino-2-methyl-1,3,-propanediol were condensed at room temperature in the presence of EDC and HOBT in dimethylformamide, to obtain (RS-α-[[[2- -hydroxy-1-(hydroxymethyl)-1-methyl]carbamoyl]methyl]hydrocinnamic acid ethyl ester, MS: 324 (M+H)+.
[11] W. G. Kofron and L. G. Wideman, J. Org. Chem. 37, 555 (1972)

50 mg of α-chymotrypsin were added to a suspension of 0.54 g (1.67 mmol) of (RS)-α-[[[2-hydroxy-1-(hydroxymethyl)-1-methyl]carbamoyl]methyl]hydrocinnamic acid ethyl ester in 15 ml of water. The pH value was held at 7.1 by adding 0.1N sodium hydroxide solution (temperature 25°). After 18 hours, 9 ml of 0.1N sodium hydroxide solution had been consumed and the reaction mixture was extracted with ether. The aqueous phase was adjusted to pH 4 with 1N hydrochloric acid and subsequently evaporated under reduced pressure. The residue was digested with ethyl acetate. The organic phase was evaporated under reduced pressure and the residue was flash chromatographed on silica gel with a 9:1 mixture of methylene chloride and methanol, to obtain (R)-α-[[[2-hydroxy-1-(hydroxymethyl)-1-methyl]carbamoyl]methyl]hydrocinnamic acid as a colorless foam, MS: 264 (M-CH2OH)[30].

5-[(RS)-3-Carboxy-4-phenylbutyramido]valeric acid t-butyl ester

3-Ethoxycarbonyl-4-phenylbutyric acid and 5-aminovaleric acid t-butyl ester[12] were condensed in the presence of EDC and HOBT in dimethylformamide to give 5-[(RS)-3-(ethoxycarbonyl)-4-phenylbutyramido]valeric acid t-butyl ester, MS: 392 (M+H)+. Saponification of this ester with 1N sodium hydroxide solution in ethanol at 50° yielded 5-[(RS)-3-carboxy-4-phenylbutyramido]valeric acid t-butyl ester, MS: 307 (M-C4H8)+.
[12] J. H. C. Nayler et al., J. Med. Chem. 20, 1445 (1977)

3-Carboxy-4-phenybutyryl-L-proline t-butyl ester

The compound 3-carboxy-4-phenylbutyryl-L-proline t-butyl ester [MS: 361 (M)+] was synthesized by condensing 3-ethoxy-carbonyl-4-phenylbutyric acid and L-proline t-butyl ester to give 3-ethoxycarbonyl-4-phenylbutyryl-L-proline t-butyl ester [MS: 389 (M)+] and subsequently saponifying analogously to the preparation of 2-(RS)-benzyl-3-morpholinocarbonylpropionic acid described hereinafter.

(RS)-[(4-Benzyl-4-piperidinyl)carbamoyl ]imidazole -4-propionic acid 2 g (10 mmol) of (RS)-(imidazol-4-ylmethyl)malonic acid monomethyl ester (prepared according to a generally known procedure from malonic acid methyl ester by alkylation with chloromethylimidazole and subsequent saponification) and 1.91 g (10 mmol) of 4-aminobenzylpiperidine were stirred at room temperature for 72 hours with 1.91 g (10 mmol) of EDC in 100 ml of dimethylformamide. The reaction solution was then evaporated under reduced pressure and the residue was dissolved in 100 ml of methylene chloride and washed with 30 ml of water. The organic phase was then dried over sodium sulfate and evaporated to dryness. The residue was digested with ether and thereafter filtered off, to give (RS)-[(4-benzyl-4-piperidinyl)carbamoyl-]imidazole-4-propionic acid methyl ester as a colorless powder, MS: 370 (M)+.

371 mg (1 mmol) of the above methyl ester were dissolved in 10 ml of a 1:1 mixture of methanol and water and stirred at room temperature for 24 hours with 1 ml of 1N potassium hydroxide in methanol. The reaction solution was then evaporated under reduced pressure, the residue was dissolved in water and washed with ether. The aqueous phase was then acidified with 1 mol equivalent of hydrochloric acid and evaporated under reduced pressure, to obtain (RS)-[(4-benzyl-4-piperidinyl)carbamoyl]imidazole-4-propionic acid as a colorless oil +. MS: 312 (M-CO$_2$) .

2-(RS)-Benzyl-3-morpholinocarbonylpropionic acid 1.0 g (4.2 mmol) of 3-ethoxycarbonyl-4-phenylbutyric acid was dissolved in 25 ml of dimethylformamide and treated with 0.37 g (4.2 mmol) of morpholine, 0.81 g (4.2 mmol) of EDC and 1.3 g (8.4 mmol) of HOBT and stirred at room temperature for 48 hours. The reaction solution was then evaporated in a high vacuum and the residue was dissolved in ethyl acetate and washed in succession with water, saturated sodium bicarbonate solution and saturated sodium chloride solution. The organic phase was then dried over sodium sulfate and evaporated under reduced pressure, and the residue was chromatographed on silica gel using a 95:5 mixture of methylene chloride and ethanol, to give 2-(RS)-1-benzyl-3-morpholinocarbonylpropionic acid ethyl ester as a colorless oil, MS: 305 (M)+.

0.42 g (1.4 mmol) of the above ester was dissolved in 2 ml of ethanol and treated with 2.1 ml (1.5 mol equivalents) of 1N sodium hydroxide solution. The reaction solution was then stirred at 50° for 4 hours and the residue was dissolved in water and washed with ether. The aqueous phase was acidified with 2.3 ml of 1N hydrochloric acid and extracted with methylene chloride. The organic extracts were dried over sodium sulfate and evaporated under reduced pressure to give 2-(RS)-benzyl-3-morpholinocarbonylpropionic acid was obtained as a colorless oil, which was used directly in the next step. MS: 277 (M)+.

Example 34

100 mg (0.13 mmol) of t-butoxycarbonyl [2-[(RS)-3-[[(S)-1-[[(1S,2S,4S)-1-(cyclohexylmethyl)-2-hydroxy-4-isopropyl-5-hexenyl]carbamoyl]- 2 imidazol-4-ylethyl]-carbamoyl]-4-phenylbutyramido]ethyl]glycine t-butyl ester were dissolved in 2 ml of acetic acid and stirred at room temperature for 3 hours with 4 ml of 1N hydrochloric acid/acetic acid. Thereafter, the reaction mixture was evaporated under reduced pressure and the residue was digested with ether and filtered off, to give N-[2-[(RS)-3-[[(S)-1-[[(1S,2S,4S)-1-(cyclohexylmethyl)-2-hydroxy-4-isopropyl-5-hexenyl]carbamoyl]-2-imidazol 4-ylethyl]carbamoyl]-4-phenylbutyramido]ethyl]glycine dihydro chloride as a powder, MS: 681 (M+H)+.

EXAMPLE 35

54 mg of I-butyl 5-[(RS)-3-[[(S)-1-[[(1S,2S,4S)-1(cyclohexylmethyl)-2-hydroxy-4-isopropyl-5 hexenyl]carbamoyl]2-imidazol-4-ylethyl]carbamoyl]-4-phenyl butyramido]valerate were dissolved in 1 ml of acetic acid and treated at room temperature with 2 ml of hydrochloric acid/acetic acid (1.5N) and stirred at this temperature for 2.5 hours. The reaction mixture was then evaporated under reduced pressure and the residue was digested with ether and filtered off, to obtain 5-[(RS)-3-[[(S)-1-2S,4S)-1-(cyclohexylmethyl)-2-hydroxy-4-isopropyl-5-hexenyl]carbamoyl]-2-imidazol-4-ylethyl]carbamoyl]-4-phenylbutyramido]valeric acid hydrochloride as a colorless powder MS; 680 (M+H)+.

Example 36

The following compounds were prepared in a manner analogous to that described in Example 27:

From (S)-α-amino-N-[(1S,2S,4S)-1-(cyclohexylmethyl)-2-hydroxy.4-isopropyl-5-hexenyl]imidazole-4-propionamide and (RS) 2-benzyl-6,6-dimethyl-4-oxoheptanoic acid,, the (S)-N-[(1S,2S,4S)-1-(cyclohexylmethyl)-2-hydroxy-4-isopropyl-5-hexenyl]-α-[(RS)-α-(4,4-dimethyl-2-oxopentyl)hydrocinnamamido]imidazole-4-propionamide, MS: 635 (M+H)+. ;

From (S)-α-amino-N-[(1S,2S,4S)-1-(cyclohexylmethyl)-2-hydroxy-4-isopropyl 5-hexenyl]imidazole-4-propionamide and (RS)-α-benzyl-γ-oxocyclohexanebutyric acid and subsequent separation of the two epimers, the less polar (S)-α-[(S)-α-[(cyclohexylcarbonyl)methyl]hydrocinnamamido]-N-[(1S,2S,4S)-1-(cyclohexylmethyl)-2-hydroxy-4-isopropyl-5-hexenylimidazole 4-propionamide [MS 647 (M+H)+] and the more polar (S)-α-[(R)-α-[(cyclohexylcarbonyl)methyl]hydrocinnamamido]-N [(1S,2S,4S)-1-(cyclohexylmethyl)-2-hydroxy-4-isopropyl-5-hexenyl]imidazole 4-propionamide, MS: 647 (M+H)+;

From (S)-α-amino-N-[(1S,2S,4S) 1-(cyclohexylmethyl)-2-hydroxy-4-isopropyl 5-hexenyl]imidazole-4-propionamide and (RS)-α-benzyl-γ-oxocyclopentanebutanoic acid, the (S)-N-1(1S,2S,4S)-1-(cyclohexylmethyl)-2-hydroxy-4-isopropyl-5-hexenyl]-α- [(RS-α-[(cyclopentylcarbonyl)methyl]hydrocinnamamido]imidazole-4-propionamide, MS: 633 (M+H)+. :

From (S)-α-amino-N-(1S,2S,4S)-1-(cyclohexylmethyl)-2-hydroxy-4-isopropyl-5-hexenyl]imidazole-4-propionamide and (RS)-2-benzyl 5,5-dimethyl-4-oxohexanoic acid, the (S)-α-[(RS)-2-benzyl-5,5-dimethyl-4-oxohexananamido]-N-[(1S,2S,4S)-1-(cyclohexylmethyl)-2-hydroxy-4-isopropyl-5-hexenyl]imidazole-4-propionamide, MS: 621 (M+H)+. ;

From (S)-α-amino-N-[(1S,2S,4S)-1-(cyclohexylmethyl)-2-hydroxy-4-isopropyl-5-hexenyl]imidazole-4-propionamide and (R)-2-benzyl-5,5-dimethyl4-oxohexanoic acid, the (S)-α-[(R)-2-benzyl-5,5-dimethyl-4-oxohexanamido]-N[(1S,2S,4S)-1-(cyclohexylmethyl)-2- hydroxy-4-isopropyl-5-hexenyl]imidazole-4-propionamide, MS; 621 (M+H)$^+$.;

From (S)-β-amino-N-[(1S,2S,4S)-1-(cyclohexylmethyl)-2-hydroxy-4-isopropyl-5 hexenyl]imidazole-4-propionamide and (αRS,S)-α-benzyl-1-(benzyloxycarbonyl)-γ-oxo-2-pyrrolidinebutyric acid, the benzyl (S)-2 [[(RS)-α-[[(S)-1-[[(1S,2S,4S)-1-(cyclohexylmethyl) 2-hydroxy 4-isopropyl-5-hexenyl]carbamoyl]-2-imidazol-4-ylethyl]carbamoyl]phenethyl]acetyl]-1-pyrrolidinecarboxylate, MS: 768 (M+H)$^+$.

The acids used as the starting materials were prepared as follows in analogy to the preparation of 2-(RS) benzyl-4-(4-chlorophenyl)-4-oxobutyric acid (see Example 27):

From 1 chloro-4,4-dimethyl 2-pentanone, which in turn was prepared in a known manner from 3,3-dimethylbutyryl chloride by reaction with diazomethane and hydrogen chloride, and benzyl malonic acid diethyl ether, the (RS)-2-benzyl-6,6 dimethyl-4-oxoheptanoic acid;

From bromoacetylcyclohexane[13] and benzylmalonic acid diethyl ester, the (RS) β-benzyl-γ-oxo cyclohexaneburylo acid;
[13] M. Gaudry and A. Marquet, Tetrahedron, 1970, 564.

From bromoacetylcyclopentane[13] and benzylmalonic acid diethyl ester, the (RS)-α- benzyl-γ-oxocyclopentanebutyric acid;
[13] M. G.audry and A. Marquet, Tetrahedron, 1970, 5611.

From N-benzyloxycarbonyl-prolyl-bromomethane which was prepared in analogy to the preparation of N-t-butoxycarbonyl prolyl bromomethane[14]. and benzylmalonic acid diethyl ester, the (αRS,S)-α-benzyl-1-(benzyloxcarbonyl)-γ-oxo-2-pyrrolidinebutyric acid.
[14] EPX 0.129.163.

The (RS)-2-benzyl-5,5-dimethyl-4-oxohexanoic acid and the enantiomeric (R)-2-benzyl-5,5-dimethyl-4-oxohexanoic acid which were likewise used as starting materials were known from European Patent Publication 0 184 550.

EXAMPLE 37

The following compounds were prepared by catalytically hydrogenating the corresponding olefins in a manner analogous to that described in Example 2:

(S)-N-[(1S,2S,4S)-1-(Cyclohexylmethyl) 4-ethyl 2-hydroxy-5-methylhexyl]-α-[(R)-α-[(morpholinocarbonyl)-methyl]hydrocinnamamido]imidazole-4-propionamide, MS: 652 (M+H)$^+$;

(S)-N-[(R)-α-(3,3-dimethyl-2-oxobutyl)hydro cinnamamido]-N-[(1S,2S,4S)-1 (cyclohexylmethyl) 2-hydroxy-4-isopropylhexyl]imidazole 4-propionamide, MS: 623 (M+H)$^+$;

(S)-N-[(1S,2S,4S)-1-(cyclohexylmethyl) 2-hydroxy-4-isopropylhexyl]-α-[[[(R)-α-2-hydroxy-1-(hydroxymethyl)-1-methylethyl]carbamoyl]methyl]hydrocinnamamido]imidazole-4-propionamide, MS: 620 (M+H)$^+$:

N-[(S)-1-[[(1S,2S,4S)-1-(cyclohexylmethyl)-2-hydroxy-4-isopropylhexyl]carbamoyl]-2-imidazol-4-ylethyl]-γ-oxo-α-(1-naphthylmethyl)-4-morpholinebutyramide MS: 702 (M+H)$^+$.

EXAMPLE 38

90 mg (0.23 mmol) of (S)-α-amino-N- [(1S,2S,4S)-1-(cyclohexylmethyl)-2-hydroxy-4-isopropyl-5-hexenyl]imidazole-4-propionamide and 0.047 ml of Hünig base in 2ml of acetonitrile were treated dropwise at room temperature with a solution of 60.7 mg of (S)-α-[(3,3-dimethylbutyryl)oxy]hydrocinnamic acid and 101 mg of BOP in 5 ml of acetonitrile. The mixture was stirred at room temperature for 4 hours, subsequently poured into 2N sodium bicarbonate solution and extracted with methylene chloride. The organic phase was washed with ammonium chloride solution and dried over sodium sulfate. The solvent was removed under reduced pressure and the residue was chromatographed on silica gel. After elution with a 20:1 mixture of methylene chloride and methanol, there were obtained 50 mg (34%) of (S)-α-[[(S)-1-[[(1S,2S,4S)-1-(cyclohexylmethyl)-2-hydroxy-4-isopropyl 5-hexenyl]carbamoyl]-2-imidazol-4-ylethyl]carbamoyl]phenethyl 3,3-dimethylbutyrate as a yellow oil. MS: 637 (M+H)$^+$.

The (S)-α-[(3,3-dimethylbutyryl)oxy]hydrocinnamic acid used as the starting material was prepared as follows:

2.1 g (8.2 mmol) of (S)-2-hydroxy-3-phenylpropionic acid benzyl ester[15] and 1.24 ml of triethylamine in 100 ml of methylene chloride were treated dropwise at room temperature within 2 hours with 1.26 ml of t-butylacetyl chloride. Thereafter, the reaction mixture was stirred at 40° for 6 hours. Subsequently, the mixture was poured into water and extracted with methylene chloride. After drying over sodium sulfate, the solvent was removed under reduced pressure and the crude product was purified by flash chromatography on silica gel with a 1:3 mixture of ether and petroleum ether, to obtain 1.4 g (48%) of (S)-α-[(2,3-dimethylbutyryl)oxy]-hydrocinnamic acid benzyl ester. MS: 238 [M-(CH$_3$)$_3$CCH$_2$COOH]$^+$.
[15] Isv. Acad. Navk SSR, Ser. Khim. 1966(3), 519.

The 1.4 q (3.95 mmol) of the benzyl ester thus obtained were dissolved in 80 ml of ethanol and hydrogenated at room temperature for 2 hours and in the presence of 0.4 g of palladium-on-carbon. Filtration of the catalyst and evaporation of the solvent under reduced pressure yielded 1 g (96%) of (S)-α-[(3,3-dimethylbutyl)oxy]hydrocinnamic acid as a colorless oil which was used directly in the next step.

EXAMPLE 39

100 mg (0.394 mmol) of (αS,βS)-β-amino-α-[(S)-2--isopropyl-3-butenyl]cyclohexanepropanol in a mixture of 3.5 ml of dimethylformamide and 7 ml of acetonitrile were treated at room temperature with 0.079 ml of Hünig base. Thereafter, 174 mg of BOP and 150 mg (0.394 mmol) of (S)-α-(dibenzylacetoxy)imidazole-4-propionic acid were added thereto and the solution was stirred at room temperature for 6 hours. The mixture is then diluted with 60 ml of ethyl acetate and washed with 1N hydrochloric acid and sodium bicarbonate solution. The organic phase was dried over sodium sulfate and the solvent was removed under reduced pressure. The residue was chromatographed on silica gel with a 10:1 mixture of methylene chloride and methanol, to obtain 179 mg of (S)-1-[[(1S,2S,4S)-1-(cyclohexyl-methyl)-2-hydroxy-4-isopropyl-5-hexenyl]carbamoyl]-2-(imidazol-4-yl)ethyldibenzylacetate as an amorphous powder. MS: 596 (M—OH)$^+$.

The (S)-α-(dibenzylacetoxy)imidazole-4-propionic acid used above as the starting material was prepared as follows:

Dry hydrochloric acid gas was conducted at 0° for 3 minutes through a suspension of 2.5 g of α-hydroxy imidazolepropionic acid[16] in 80 ml of benzyl alcohol, and the solution so obtained was allowed to stand at room temperature for 12.20 hours. The excess benzyl alcohol was distilled off in a high vacuum and the residue was dissolved in methylene chloride and washed with sodium bicarbonate solution. The organic phase was dried over sodium sulfate and evaporated under reduced pressure. The residue was purified by flash chromatography on silica gel with a 10:1 mixture of methylene chloride and methanol, to obtain 3.5 g (89%) of (S)-α-hydroxyimidazolepropionic acid benzyl ester as a yellow oil. MS: 246 (M)+.

[16] C. E. Baerk and A. Merster, JACS 73, 1336.

6.19 ml (48.3 mmol) of benzenesulfonyl chloride were added dropwise at -5° to 10.53 g (43.8 mmol) of dibenzyl acetic acid in 50 ml of pyridine, and the reaction solution was stirred at room temperature for 30 minutes. Subsequently, a solution of 6 g (24.4 mmol) of (S)-α-hydroxyimidazolepropionic acid benzyl ester in 5 ml of pyridine was added dropwise at -5° and the solution was stirred at 0° for 2 hours and thereafter at room temperature for 2 hours. The reaction mixture was then poured onto 3N hydrochloric acid/ice and extracted with ethyl acetate. The organic extracts were thereafter washed with 2N sodium bicarbonate solution, dried over sodium sulfate and evaporated under reduced pressure. The residue was flash chromatographed on silica gel using a 15:1 mixture of methylene chloride and ethyl acetate, to obtain 6.35 g (47%) of a 1:1 mixture of (S)-α-dibenzylacetoxy-N-(phenylsulfonyl)imidazole-4-propionic acid benzyl ester and (S)-α,N-bis(dibenzylacetoxy)imidazole-4-propionic acid benzyl ester as a yellow oil which was used in the next step without further purification.

95 ml of a 0.3N hydrochloric acid/methanol solution were added to 5.74 g (9.4 mmol) of the above mixture in 25 ml of methanol and stirred at room temperature for 2 hours. The mixture was poured into ice/sodium bicarbonate and the product was extracted with ethyl acetate, dried over sodium sulfate and the solvent was removed under reduced pressure. The residue was purified by flash chromatography on silica gel, to obtain 3.2 g (70%) of (S)-α-(dibenzylacetoxy)-imidazole-4-propionic acid benzyl ester. MS =468 (M)+.

3.2 g (6.83 mmol) of (S)-α-(dibenzylacetoxy)imidazole-4-propionic acid benzyl ester in 150 ml of methanol were hydrogenated at room temperature for 2 hours in the presence of 660 mg of palladium-on-carbon. The catalyst was filtered off and the filter residue was washed several times with a 1:1 mixture of methylene chloride and methanol. The solution was concentrated under reduced pressure until crystallization occurred. Recrystallization of the crystallizate from methylene chloride/methanol yielded 2.5 g (96%) of (S)-α-(dibenzylacetoxy)imidazole-4-propionic acid, melting point 210°.

EXAMPLE 40

442 mg (1 mmol) of BOP and 0.204 ml of Hünig base were added to 236.2 mg (1 mmol) of R-(+)-α-benzylsuccinic acid monoethyl ester[17] and 390.6 mg (1 mmol) of (S)-α-amino-N-[(1S,2S,4S)-1-(cyclohexylmethyl)-2-hydroxy-4-isopropyl-5-hexenyl]imidazole-4-propionamide in acetonitrile and the solution obtained was stirred at room temperature for 20 hours. The reaction mixture was poured onto 1N hydrochloric acid/ice and extracted with ethyl acetate. The organic extracts were washed with sodium bicarbonate solution, dried over sodium sulfate and evaporated. The residue was chromatographed on silica gel with a 10:1 mixture of methylene chloride and methanol as the eluting agent, to obtain 465 mg (76%) of ethyl (R)-3-[[(S)-1-[[(1S,2S,4S)-1-(cyclohexylmethyl)-2-hydroxy-4-isopropyl-5-hexenyl]-carbamoyl]-2-imidazol-4-ylethyl]carbamoyl]-4-phenylbutyrate as an amorphous powder. MS: 609 (M+H)+.

[17] S. G. Cohen, A. Milovanovic, JACS 90, 3495 (1968).

EXAMPLE 41

181 mg (0.404 mmol) of BOP and 0.083 ml of Hünig base were added to 66.5 mg (0.404 mmol) of (S)-(+)-α-methylhydrocinnamic acid[18] and 157 mg (0.404 mmol) of (S)-α-amino-N-[(1S,2S,4S)-1-(cyclohexylmethyl)-2-hydroxy-4-isopropyl-5-hexenyl]imidazole-4-propionamide in 10 ml of acetonitrile and stirred at room temperature for 16 hours. The reaction solution was poured into 1N hydrochloric acid/ice and extracted with ethyl acetate. The organic extracts were washed with sodium bicarbonate solution and dried over sodium sulfate. The solvent was then removed under reduced pressure and the residue was chromatographed on silica gel with a 10:1 mixture of methylene chloride and methanol, to obtain 136 mg (63%) of N-[(1S,2S)-1-(cyclohexylmethyl)-2-hydroxy-4-isopropyl-5-hexenyl]-α-[(S)-α-methylhydro-cinnamamido]imidazole-4-propionamide as an amorphous solid. MS: 537 (M+H)+.

[18] A. W. Schrecker J. Org. Chem. 22, 33 (1957).

EXAMPLE 42

135 mg of BOP and 0.062 ml of Hünig base were added to 73 mg of α-methylcinnamic acid and 117.75 mg of (S)-α-amino-N-[(1S,2S,4S)-1-(cyclohexylmethyl)-2-hydroxy-4-isopropyl-5-hexenyl]imidazole-4-propionamide in 5 ml of acetonitrile and stirred at room temperature for 20 hours. The reaction solution was poured onto 3N hydrochloric acid/ice and extracted with ethyl acetate. The organic phase was washed with 2N sodium carbonate solution and dried over sodium sulfate. The solvent was then removed under reduced pressure and the residue was chromatographed on silica gel with a 10:1 mixture of methylene chloride and methanol, to obtain 100 mg of N-[[(1S,2S,4S)-1-(cyclohexylmethyl)-2-hydroxy-4-isopropyl-5-hexenyl]-α-[α-methylcinnamoyl]-amino]-imidazole-4-propionamide as an amorphous solid. MS: 535 (M+H)+.

EXAMPLE 43

106 mg (0.404 mmol) of t-butoxycarbonyl-α,β-dehydrophenylalanine[19] and 157 mg of (S)-α-amino N-[(1S,2S,4S)-1-(cyclohexylmethyl)-2-hydroxy-4-isopropyl-5-hexenyl]imidazole-4-propionamide in 10 ml of acetonitrile were treated with 181 mg of BOP and 0.083 ml of Hünig base and subsequently stirred at room temperature for 16 hours. Thereafter, the solution obtained was poured onto 1N hydrochloric acid/ice, extracted with ethyl acetate, washed with 2N sodium carbonate solution, dried over sodium sulfate, and the solvent was removed under reduced pressure. The residue was chromatographed on silica gel with a 20:1 mixture of methylene chloride and methanol, to obtain 144 mg (54%) of (S)-α-[α-(t-butoxycarbonyl amino)cinnamoyl]-N-[(1S,2S,4S)-1-(cyclohexylmethyl)-2-hydroxy-4-isopropyl-5-hexenyl]imidazole-4-propionamide as an amorphous solid. MS: 636 (M+H)+.

[19] H. Poisel, Chem. Ber. 110, 948 (1977).

EXAMPLE 44

100 mg (0.256 mmol) of (S)-α-amino-N-[(1S,2S,4S)-1-(cyclohexylmethyl)-2-hydroxy-4-isopropyl-5-hexenyl]imidazole-4-propionamide and 0.052 ml of Hünig base in 2 ml of acetonitrile were treated with 92 mg of (S)-α-(diphenylacetoxy)hydrocinnamic acid and 113 mg of BOP in 2 ml of acetonitrile and stirred at room temperature for 12 hours. The reaction solution was then poured onto 1N hydrochloric acid/ice, extracted with ethyl acetate, the organic phase was washed with sodium carbonate solution, dried over sodium sulfate and, finally, the solvent was removed under reduced pressure. The residue was chromatographed on silica gel with a 10:1 mixture of methylene chloride and methanol, to obtain 130 mg of (S)-α-[[(S)-1-[[(1S,2S)-1-(cyclohexylmethyl)-2-hydroxy-4-isopropyl-5-hexenyl]carbamoyl]-2-imidazol-4-ylethyl]carbamoyl]phenethyl dibenzylacetate in the form of an amorphous solid. MS 733 (M+H)+.

The (S)-α-(diphenylacetoxy)hydrocinnamic acid used as the starting material was prepared as follows:

1.06 g (5 mmol) of diphenylacetic acid in 5 ml of pyridine were treated dropwise at -5° with 0.833 ml (6.5 mmol) of benzenesulfonyl chloride and the solution was subsequently stirred at room temperature for 30 minutes. Then, 1.28 g (5 mmol) of (S)-2 hydroxy 3-phenyl-propionic acid benzyl ester[20] in 5 ml of pyridine were added and the mixture was stirred at 0°-10° for 2 hours and at room temperature for a further 2 hours. The reaction solution was treated with water and extracted with ethyl acetate. The organic phases were washed with 1N hydrochloric acid and sodium bicarbonate solution and dried over sodium sulfate. The solvent was evaporated under reduced pressure and the residue was flash chromatographed on silica gel with a 4:1 mixture of petroleum ether/ether, to obtain 1.8 g (80%) of benzyl (S)-α-(diphenylacetoxy)hydrocinnamate in the form of a yellow oil. MS: 359 (M-benzyl)+.
[20]Isv. Acad. Navk SSR, Ser. Khim. 1966(3), 519.

The 1.8 g of the above-named benzyl ester were dissolved in 180 ml of acetic acid, treated with 300 mg of palladium-on-carbon and hydrogenated at room temperature until the theoretical amount of hydrogen had been taken up (approximately 2 hours). The catalyst was then filtered off and the solvent was removed under reduced pressure, upon which the desired acid began to crystallize out slowly. Filtration of the separated crystals yielded 1.3 g (90%) of (S)-α-(diphenylacetoxy)hydrocinnamic acid. MS: no mol peak 212 (diphenylacetic acid)+ 167 (diphenylmethyl)+.

EXAMPLE 45

100 mg of (αS,βS)-β-amino-α-[(S)-2-isopropyl-3-butenyl]cyclohexanepropanol in 20 ml of acetonitrile were treated with 0.080 ml of Hünig base, 174 mg of BOP and 140 mg of (S)-3-carbamoyl-2-(dibenzylacetoxy)propionic acid and stirred at room temperature for 12 hours. Thereafter, the reaction solution was poured onto 1N hydrochloric acid/ice, extracted with ethyl acetate, the extracts were washed with sodium carbonate solution and, finally, dried over sodium sulfate. The solvent was then removed under reduced pressure and the residue was chromatographed on silica gel with a 20:1 mixture of methylene chloride and methanol, to obtain 142 mg (60%) of (S)-2-carbamoyl-1-[[(1S,2S,4S)-1-(cyclohexylmethyl)-2 -hydroxy-4-isopropyl-5-hexenyl]- carbamoyl]ethyl dibenzylacetate in the form of a resin. MS: 591 (M+H)+.

The (S)-3 carbamoyl-2-(dibenzylacetoxy)propionic acid used as the starting material was prepared as follows:

480 mg (2 mmol) of dibenzylacetic acid in 3 ml of pyridine were treated at -5° with 0.34 ml of benzenesulfonyl chloride and subsequently stirred at room temperature for 30 minutes. Thereafter, 447 mg (2 mmol) of benzyl (S)-β-malamidate were added and the reaction solution was stirred at 0° for 2 hours and then at room temperature for 2 hours. The reaction solution was then diluted with 100 ml of ethyl acetate, dilute hydrochloric acid was added, and the two phases obtained were separated. The organic phase was washed with sodium carbonate solution, dried over sodium sulfate and evaporated under reduced pressure. Chromatography of the residue on silica gel using a 4:1 mixture of methylene chloride and ethyl acetate as the elutinq agent yielded 539 mg (59%) of benzyl (S)-3-carbamoyl 2-(dibenzyl acetoxy)propionate in the form of a yellow oil. MS: 354 (M-benzyl)+.

520 mg of the above-named benzyl ester in 5 ml of methanol were hydrogenated at room temperature for two hours in the presence of 100 mg of palladium-on-carbon. Thereafter, the catalyst was filtered off and the solvent was removed under reduced pressure to obtain 370 mg (90%) of (S)-3-carbamoyl-2-(dibenzyl-acetoxy)-propionic acid as a white solid. MS: 338 (M—NH$_3$)+.

EXAMPLE 46

100 mg (0.256 mmol) of (S)-α-amino-N-[(1S,2S,4S)-1-(cyclohexylmethyl)-2-hydroxy-4-isopropyl-5-hexenyl]-imidazole-4-propionamide and 0.052 ml of Hünig base in 2 ml of acetonitrile were treated at room temperature with 100 mg of N-(dibenzylcarbamoyl)-3-phenyl-L-alanine and 113 mg of BOP and subsequently stirred at room temperature for 12 hours. Thereafter, the reaction solution was poured onto 1N hydrochloric acid/ice, extracted with ethyl acetate, the extracts were dried over sodium sulfate and the solvent was removed under reduced pressure. Chromatography of the residue on silica gel using a 10:1 mixture of methylene chloride and methanol as the eluting agent yielded 130 mg of 1,1-dibenzyl-3-[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl]urea in the form of an amorphous solid. MS: 761 (M+H)+.

The N-(dibenzylcarbamoyl)-3-phenyl-L-alanine used as the starting material was prepared as follows:

1 g (5.06 mmol) of dibenzylamine and 1.73 ml (10.1 mmol) of Hünig base in 50 ml of methylene chloride were treated dropwise while cooling with ice with 2.6 ml of phosgene in toluene (20%. 5.06 mmol) and the solution obtained was stirred at 0° for 3 hours. Then, 1.1 g of L-phenylalanine methyl ester were added and the mixture was heated to 40° for 12 hours. Thereafter, the reaction mixture was poured into water, extracted with methylene chloride and the extracts were dried over sodium sulfate. The solvent was then removed under reduced pressure and the residue was chromatographed on silica gel using a 15:1 mixture of methylene chloride and ether as the eluting agent, to obtain 900 mg (45%) of N-(dibenzylcarbamoyl)-3-phenyl-L-alanine methyl ester as a white solid. MS: 402 (M)+.

900 mg (2.23 mmol) of the above-named methyl ester in 20 ml of ethanol were treated with 9 ml of 0.5N sodium hydroxide solution (4.46 mmol) and heated to 40° for 1 hour. Thereafter, the reaction solution was acidified and the product was extracted with methylene chloride. The organic phase was dried over sodium sulfate and the solvent was removed under reduced pressure, to obtain 100 mg (92%) of N-(dibenzylcarbamoyl)-3-phenyl-L-alanine as an amorphous solid. MS: 388 (M)+.

EXAMPLE 47

100 mg (0.52 mmol) of (S)-α-amino- N-[(1S,2S,4S)-1-(cyclohexylmethyl)-2-hydroxy-4-isopropyl-5-hexenyl]imidazole-4-propionamide and 0.052 ml of Hünig base in 2 ml of acetonitrile were treated at room temperature with 99 mg of N-(morpholinocarbamoyl)-3-phenyl-L-alanine and 113 mg of BOP in 2 ml of acetonitrile and stirred at room temperature for 12 hours. Thereafter, the reaction solution was poured onto 1N hydrochloric acid/ice, extracted with ethyl acetate, the organic extracts were dried over sodium sulfate and the solvent was removed under reduced pressure. The residue was chromatoqraphed on silica gel with a 10:1 mixture of methylene chloride and methanol, to obtain 130 mg (67%) of (S)-N-[(1S,2S,4S)-1-(cyclohexyl-methyl)-2-hydroxy-4-isopropyl-5 hexenyl]-α-2-[N-(morpholinocarbamoyl)-3-phenyl-L-alanyl-]amino]imidazole-4-propionamide as an amorphous solid. MS: 651 (M+H)+.

The N-(morpholinocarbamoyl)-3-phenyl-L-alanine used as the starting material was prepared as follows:

3.6 ml of phosgene in toluene (20%. 6.95 mmol) were added dropwise while cooling with ice to 0.6 ml (6.95 mmol) of morpholine and 2.4 ml (13.9 mmol) of Hünig base in 20 ml of methylene chloride, and the solution was stirred at 0° for 3 hours. Thereafter, 1.5 g (6.95 mmol) of phenylalanine methyl ester hydrochloride were added and the reaction solution was stirred at 40° for 12 hours. Subsequently, the reaction solution was poured onto ice and extracted with methylene chloride. The organic phase was dried over sodium sulfate and evaporated under reduced pressure. Chromatography of the residue on silica gel using a 2:1 mixture of methylene chloride and ether as the eluting agent yielded 400 mg (20%) of N-(morpholino-carbamoyl)-3-phenyl-L-alanine methyl ester in the form of a resin. MS: 292 (M)+.

400 mg (1.37 mmol) of the above-mentioned methyl ester in 10 ml of ethanol were treated with 5.5 ml of 0.5N sodium hydroxide solution (2.75 mmol). The reaction mixture was then stirred at 40° for 1 hour, subsequently poured onto 3N hydrochloric acid/ice, extracted with methylene chloride, the organic extracts were dried over sodium sulfate and, finally, the solvent was removed under reduced pressure. There were thus obtained 210 mg (55%) of N-(morpholinocarbamoyl)-3-phenyl-L-alanine in the form of an amorphous solid. MS: 278 (M)+.

EXAMPLE 48

A solution of 100 mg (0.256 mmol) of (S)-α-amino-N-[(1S,2S,4S)-1-(cyclohexylmethyl)-2-hydroxy-4-isopropyl-5-hexenyl]imidazole-4-propionamide, 0.052 ml of Hünig base. 113 mg of BOP and 81 mg of N-(t-butoxycarbonyl)-β-pyrazol-1-yl-L-alanine[21] in acetonitrile was stirred at room temperature for 12 hours. Thereafter, the reaction mixture was poured onto 1N hydrochloric acid/ice, extracted with ethyl acetate, the extracts were dried over sodium sulfate and the solvent was finally removed under reduced pressure. Chromatography of the residue on silica gel with a 7:1 mixture of methylene chloride and methanol yielded 80 mg (50%) of white crystals of t-butyl [(S)-1-[(1S,2S,4S)-1-(cyclohexylmethyl)-2-hydroxy-4-isopropyl-5-hexenyl]-carbamoyl]-2-imidazol-4-ylethyl]carbamoyl-2-pyrazol-1-ylethyl]carbamate. MS: 628 (M+H)+.

[21]L. D. Arnold, T. H. Kalantar, J. C. Vederas, JACS 107, 7105 (1985).

EXAMPLE 49

A solution of 103 mg of N-[[2-(4-biphenyloxy)ethyl]carbamoyl]-3-phenyl-L-alanine and 113 mg of BOP in acetonitrile was added to 100 mg (0.256 mmol) of (S)-α-amino-N-[(1S,2S,4S)-1-(cyclohexylmethyl)-2-hydroxy-4-isopropyl-5-hexenyl]imidazole-4-propionamide 0.052 ml of Hünig base in 5 ml of acetonitrile, and the mixture was subsequently stirred at room temperature for 12 hours. Subsequently the reaction mixture was poured onto 1N hydrochloric acid/ice, extracted with ethyl acetate, the extracts were dried over sodium sulfate and evaporated to dryness under reduced pressure. The crude product was purified by chromatography on silica gel with a 10:1 mixture of methylene chloride and methanol, to obtain 90 mg (45%) of 1-[2-(4-biphenyloxy)ethyl]-3-[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]- carbamoyl]phenethyl]urea as an amorphous powder. MS: 777 (M+H)+.

The N-[[2-(4-biphenyloxy)ethyl]carbamoyl]-3-phenyl-L-alanine used as the starting material was prepared as follows:

4.8 ml of Hünig base and 7 ml of a 20% phosgene solution in toluene were added at 0° to 3 g (14.06 mmol) of 2-(4-biphenyloxy)ethylamine[22] in 100 ml of toluene and the reaction mixture was subsequently stirred at 0° for one hour. Thereafter, 6 g of L-phenylalanine benzyl ester were added and the solution was stirred at 90° for 12 hours. Thereafter, the reaction mixture was worked-up in the usual manner and the crude product was purified by chromatography on silica gel with a 10:1 mixture of methylene chloride and methanol, to obtain 4.5 g (67%) of N-[[2-(4-biphenyloxy)ethyl]carbamoyl]-3-phenyl-L-alanine benzyl ester.

[22]DOS 2.500.692.

4.5 g (9.4 mmol) of the above-named benzyl ester in 250 ml of ethanol were hydrogenated at room temperature in the presence of 0.5 g of palladium-on-carbon until the theoretical amount of hydrogen had been taken up. The catalyst was filtered off, the solvent was evaporated under reduced pressure, and the residue was recrystallized from ether/methylene chloride/methanol, to obtain 2.1 g (55%) of N-[[2-(4-biphenyloxy)ethyl]carbamoyl]-3phenyl-L-alanine, melting point 175° ; [α]$_{589}$ = +8.4° (c=1%, methanol).

EXAMPLE 50

A solution of 100 mg of (S)-α-[(dibenzylcarbamoyl)oxy]hydrocinnamic acid and 113 mg of BOP in 2 ml of acetonitrile was added to 100 mg (0.256 mg) of (S)-α-amino-N-[(1S,2S,4S)-1-(cyclohexylmethyl) 2-hydroxy-4-isopropyl-5-hexenyl]imidazole-4-propionamide and 0.052 ml of Hënig base in 5 ml of acetonitrile, and the mixture was subsequently stirred at room temperature for 12 hours. The working-up was effected in the usual manner. There were thus obtained 150 mg (77%) of (S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl dibenzyl carbamate. MS: 762 (M+H)+.

The (S)-α-(dibenzylcarbamoyloxy)hydrocinnamic acid used as the starting material was prepared as follows:

2.23 ml (4.3 mmol) of a 20% phosgene solution in toluene were added dropwise while cooling with ice to 1.0 g (3.9 mmol) of (S)-2-hydroxy-3-phenylpropionic acid and 1.68 ml (3.9 mmol) of Hünig base in 20 ml of tetrahydrofuran, and the mixture was subsequently stirred at 0°-10° for 1.5 hours. Then, 0.824 ml (4.3 mmol) of dibenzylamine in 20 ml of tetrahydrofuran were added dropwise and the reaction solution was stirred at room temperature for a further 12 hours. Subsequently, the mixture was poured on to ice, neutralized with potassium bicarbonate solution and extracted with ethyl acetate. For purification, the crude product obtained was flash chromatographed on silica gel using a 3:1 mixture of petroleum ether and ether, to obtain 825 mg (42%) of (S)-α-[(benzyloxy)carbonyl]phenethyl dibenzyl carbamate as a resin. MS: 388 (M-benzyl)+.

0 8 g of the above-described benzyl ester was hydrogenated at room temperature for 2.5 hours in 30 ml of a 4:1 mixture of methanol and ethyl acetate, in the presence of 80 mg of palladium-on-carbon. Thereafter, the catalyst was filtered off and the solvent was evaporated under reduced pressure. There were thus obtained 461 mg (73%) of (S)-α-[(dibenzylcarbamoyl)oxy]hydrocinnamic acid in the form of a resin. MS: 389 (M)+.

EXAMPLE 51

A solution of 100 mg of ethyl (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyrate in 30 ml of methanol was saturated with ammonia for 1-2 minutes and subsequently left to stand at room temperature for 12 hours. Thereafter, the solvent was removed under reduced pressure and the residue was chromatographed on silica gel with 10% methanol in methylene chloride as the eluting agent, to obtain 63 mg (66%) of (S)-α-[(R)-α-(carbamoylmethyl)hydrocinnam-amido]-N-[(1S,2S,4S)-1-(cyclohexylmethyl)-2-hydroxy-4-isopropyl-5-hexenyl]imidazole-4-propionamide as a resin. MS: 580 (M+H)+.

EXAMPLE 52

A solution of 84.62 mg (0.3 mmol) of t-butoxycarbonyl-α-methyl-D,L-phenylalanine, 135 mg of BOP, 118 mg of (S)-α-amino-N-[(1S,2S,4S)-1-(cyclohexylmethyl)-2-hydroxy-4-isopropyl-5-hexenyl]imidazole-4-propionamide and 0.062 ml of Hünig base was stirred at room temperature for 12 hours. The reaction mixture was worked-up as described in Example 48, to obtain 125 mg (64%) of t-butyl [(R or S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-α-methylphenethyl]carbamate as an epimer mixture. The two epimers can be separated by chromatoqraphy on silica gel with 10% methanol in methylene chloride. The more polar epimer has a Rf value of 0.38, while the less polar has a Rf value of 0.46. MS: 652 (M+H)+.

The t-butoxycarbonyl-α-methyl-D,L-phenylalanine used as the starting material was prepared as follows:

2.44 g (11.16 mmol) of di-t-butyl dicarbonate in 5 ml of t-butyl alcohol were added dropwise at room temperature to 2.0 g (11.16 mmol) of α-methyl-D,L-phenylalanine in 11.16 ml of 1N sodium hydroxide solution and 10 ml of t-butyl alcohol, and the reaction mixture was subsequently stirred at room temperature overnight. Thereafter, water was added, the mixture was washed with pentane, the aqueous phase was adjusted to pH 2 by the addition of potassium bisulfate solution and extracted with ethyl acetate. The organic phase was then dried over sodium sulfate and concentrated, to give 1.56 g (50%) of t-butoxycarbonyl-α-methyl-D,L-phenylalanine as a white powder which was used directly in the next step.

EXAMPLE 53

A mixture of 100 mg (0.45 mmol) of N-benzyl-3-carbamoyl-D-alanine, 187 mg (0.45 mmol) of (S)-α-amino-N-[(1S,2S,4S)-1-(cyclohexylmethyl)-2-hydroxy 4-isopropyl-5-hexenyl]imidazole-4-propionamide 0.093 ml of Hünig base and 202 mg of BOP in 10 ml of a 2:1 mixture of acetonitrile and dimethylformamide was stirred at room temperature for 18 hours. Thereafter, the reaction mixture was poured into aqueous ammonium chloride solution, extracted with ethyl acetate, the extracts were washed with sodium carbonate solution, dried over sodium sulfate and evaporated to dryness under reduced pressure. Chromatography of the residue on silica gel with 10% methanol in methylene chloride as the eluting agent yielded 87 mg (32%) of (S)-α-[(R)-2-(benzylamino) 3-carbamoylpropionamido]-N-[(1S,2S,4S)-1-(cyclohexylmethyl)-2-hydroxy-4-isopropyl-5-hexenyl]imidazole-4-propionamide as a resin. MS: 595 (M+H)+.

The N-benzyl-3-carbamoyl-D-alanine used as the starting material was prepared as follows:

1.5 g (10 mmol) of D-asparagine hydrate in 5 ml of 2N sodium hydroxide solution were treated with 1.01 ml (10 mmol) of benzaldehyde and the reaction mixture was stirred homogeneously at room temperature for 20 minutes. Subsequently, 114 mg (3 mmol) of sodium borohydride were added portionwise, the mixture was stirred at room temperature for 30 minutes, a further 114 mg of sodium borohydride were added and, finally, the mixture was stirred at room temperature for a further 30 minutes. Thereafter, the aqueous phase was washed with methylene chloride and then adjusted to pH 6-7 with 1N hydrochloric acid, upon which crystallization occurred. The separated crystals were filtered off, washed with water and ether and finally dried in a high vacuum, to obtain 0.6 g (27%) of N-benzyl-3-carbamoyl-D-alanine as a white powder. MS 223 (M+H)+.

EXAMPLE 54

80 mg (0.13 mmol) of ethyl (R)-3-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-4-phenylbutyrate were taken up in 2 ml of a 5.6 molar alcoholic dimethylamine solution and heated to reflux for 3 hours. The solution was then evaporated and the residue was chromatographed on silica gel with a 20:1 mixture of methylene chloride and methanol to obtain 33 mg (20%) of (S)-N-[(1S,2S,4S)-1-(cyclohexylmethyl)-2-hydroxy-4-isopropyl-5-hexenyl]-α-[(R)-α-[(dimethylcarbamoyl) methyl]hydrocinnamamido]imidazole-4-propionamide as an amorphous powder. MS: 608 (M+H)+.

EXAMPLE 55

The following compounds were prepared in a manner analogous to that described in Example 40:

From 117 mg (0.3 mmol) of (S)-α-amino-N-[(1S,2S,4S)-1-(cyclohexylmethyl)-2-hydroxy-4-isopropyl-5-hexenyl]imidazole-4-propionamide and 75 mg (0.3 mmol) of N-benzyl-3-ethoxycarbonyl-D-alanine, 85 mg (45%) of ethyl (R)-3-(benzylamino)-3-[[(S)-1-[[(1S,2S,4S)-1-(cyclohexylmethyl)-2-hydroxy-4-isopropyl-5-hexyl]carbamoyl]-2-imidazol-4-ylethyl]carbamoyl]propionate as an amorphous powder. MS: 624 (M+H)+;

From 117 mg (0.3 mmol) of (S)-α-amino-α-[(1S,2S,4S)-1-(cyclohexylmethyl)-2-hydroxy 4-isopropyl-5-hexenyl]-imidazole-4-propionamide and 88 mg (0.3 mmol) of N-benzyloxycarbonyl-L-asparagine. 136 mg (71%) of benzyl [(S)-1-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]-2-carbamoylethyl]carbamate as an amorphous powder MS: 639 (M+H)+;

From 157 mg (0.4 mmol) of (S)-a-amino-N-[(1S,2S,4S)-1-(cyclohexylmethyl)-2-hydroxy-4-isopropyl-5-hexenyl]imidazole-4-propionamide and 136 mg (0.4 mmol) of N-benzoyl-γ-benzyl-D-glutamate, 115 mg (40%) of benzyl (S)-4-benzamido-4-[[(3)-1-[[(1S,2S,4S)-1-(cyclohexyl methyl)-2-hydroxy-4-isopropyl-5-hexenyl]carbamoyl]. -2-imidazol-4-ylethyl]carbamoyl]butyrate. MS: 714 (M+H)+;

From 100 mg of (S)-α-amino-N-[(1S,2S,4S)-1-(cyclohexylmethyl)-2-hydroxy-4-isopropyl-5-hexenyl-]imidazole-4-propionamide and 64 mg of (RS)-α-[[(2-hydroxyethyl)carbamoyl]methyl] -hydrocinnamic acid, 50 mg of (S)-N-[(1S,2S,4S)-1-(cyclohexylmethyl)-2-hydroxy-4-isopropyl-5-hexenyl]-α-[(RS)-α-[[(2-(hydroxethyl)carbamoyl]methyl]hydrocinnamido]imidazole-4-propionamide as a 1:1 epimer mixture MS: 624 (M+H)+;

From 100 mg of (S)-α-amino-N-[(1S,2S,4S)-1-(cyclohexylmethyl)-α-hydroxy-4-isopropyl-5-hexenyl-]imidazole-4-propionamide and 80 mg of α-[(phenethylcarbamoyl)methyl]cinnamic acid, 65 mg (37%) of (S)-N-[(1S,2S,4S)-1-(cyclohexyl methyl)-2-hydroxy-4-isopropyl-5-hexenyl]-α-[α--[(phenethylcarbamoyl)methyl]cinnamamido]imidazole-4-propionamide, MS: 682 (M+H)+;

From 214 mg (0.55 mmol) of (S)-α-amino-N-[(1S,2S,4S)-]-(cyclohexylmeIhyl)-2-hydroxy-4-isopropyl-5-exenyl]imidazole-4-propionamide and 160 mg (0.55 mmol) of (RS)-α-[2-(morpholino carbonyl)ethyl]-hydrocinnamic acid, 210 mg (60%) of (S)-N-[(1S,2S,4S)-1-(cyclohexylmethyl)-2-hydroxy-4-isopropyl-5-hexenyl]-α-[(RS)-α-[2-(morpholino-carbonyl)ethyl]hydrocinnamyl]imidazole-4-propionamide as a 1:1 epimer mixture, MS: 664 (M+H)+;

From 100 mg (0.25 mmol) of (S)-α-amino-N-[(1S,2S,4S)-1(cyclohexylmethyl)-2-hydroxy-4-isopropyl-5-hexenyl]imidazole-4-propionamide and 100 mg (0.28 mmol) of N-[(4-biphenylmethyl)carbamoyl]-3-phenyl-L-alanine, 150 mg (77%) of 1-(4-biphenylmethyl) 3-[(S)-1[[(S)-1-[[(1S,2S,4S) -1-(cyclohexylmethyl)-2-hydroxy-4-isopropyl-5-hexenyl]carbamoyl]-2-imidazol-4-ylethyl]-L-carbamoyl]phenethyl]urea, MS: 748 (M+H)+.

The respective acids used as the starting materials were prepared as follows:

N-Benzyl-3-ethoxycarbonyl-D-alanine 574 mg (2.9 mmol) of β-ethyl-D-aspartic acid, which was prepared according to the method described by Pivitti in Gazzetta, 18, 480 (1888) for the preparation of the racemic compound, were dissolved in 2.9 ml of 2N sodium hydroxide solution and treated with 0.3 ml of benzaldehyde and subsequently stirred vigorously at room temperature for one hour. 33 mg of sodium borohydride were then added and the mixture was stirred at room temperature for a further hour. Thereafter, a further 33 mg of sodium borohydride were added and the mixture was stirred at room temperature for a further hour. The mixture was subsequently extracted with ether and the aqueous phase was adjusted to pH 6-7, upon which crystallization occurred. The separated crystals were filtered off and dried in a high vacuum, to obtain 81 mg (10%) of N-benzyl-3-ethoxycarbonyl-D-alanine which was used directly in the next step. MS: 206 (M-COOH)+.

N-Benzoyl-γ-benzyl-D-qlutamate

γ-Benzyl-D-qlutamate was benzoylated according to the method described by Miller and Waelsch in Arch. Biochem. Biophys. 1952, 35, 176 for the benzoylation of γ ethyl-L-glutamate, to obtain the desired product in 75% yield, MS: 341 (M)+.

(RS)-α-[[(2-(Hydroxyethyl)carbamoyl]methyl]hydrocinnamic acid 150 mg (0.8mmol) of benzalsuccinic acid anhydride [S. G. Cohn et al., JACS, 90, 3495 (1968)]in 10 ml of methylene chloride were treated with 0.048 ml of ethanolamine and stirred at room temperature for 2 hours. The separated crystals were filtered off and dried, to obtain 155 mg (78%) of α-[[(2-(hydroxethyl)carbamoyl]methyl]cinnamic acid as colorless crystals. MS: 249 (M)+.

180 mg of the above-named acid in 5 ml of ethanol were hydrogenated at room temperature for 2 hours in the presence of 2 ml of palladium-on-carbon. Thereafter, the catalyst was filtered off and the solvent was removed under reduced pressure. The residue was dissolved in ethyl acetate and washed with 0.1N hydrochloric acid. The organic phase was dried over sodium sulfate and the solvent was evaporated under reduced pressure, to obtain 125 mg (70%) of (RS)-α-[[(2-hydroxyethyl)carbamoyl]methyl]hydrocinnamic acid which was used directly in the next step. α-[(phenethylcarbamoyl)methyl]cinnamic acid 226 mg (1.2 mmol) of benzalsuccinic acid anhydride were treated in 20 ml of methylene chloride with 0.15 ml of 2-phenethylamine and subsequently stirred at room temperature for 2 hours. The solvent was removed under reduced pressure and the residue was chromatographed on silica gel, to obtain 260 mg (70%) of α-[(phenethylcarbamoyl)methyl]cinnamic acid, MS: 309 (M)+.

(RS)-α-[2-(Morpholinocarbonyl)ethyl]hydrocinnamic acid 2.5 g (10 mmol) of benzylmalonic acid diethyl ester and 1.45 ml (10 mmol) of t-butyl acrylate in 5 ml of acetonitrile were treated with 1.49 ml of DBU and stirred at room temperature for 6 hours. Thereafter, the mixture was poured into dilute hydrochloric acid (pH 2), extracted with ether, the organic phase was washed with a small amount of water, dried over sodium sulfate and the solvent was removed under reduced pressure. There were obtained 3.7 g (97%) of 4-t-butyl 2,2-diethyl 1-phenyl-2,2,4-butanetricarboxylate as a pale yellow oil which was used directly in the next step.

1 9 g (5.4 mmol) of 4-t-butyl 2 2-diethyl 1-phenyl-2,2,4-butanetricarboxylate in 20 ml of ethanol were treated with 27 ml of 2N sodium hydroxide solution (54 mmol) and subsequently stirred at 50° for 6 hours. Thereafter, the reaction mixture was extracted with ether, the extracts were dried over sodium sulfate, and the solvent was evaporated under reduced pressure. The residue was chromatographed using a 10:1 mixture of methylene chloride and methanol as the eluting agent, to obtain 0.8 g (50%) of 3-ethyl 2,4-dihydrogen 1-phenyl-[2,2,4]-butanetricarboxylate as an oil, MS: 250 (M-$CO_2$)+.

800 mg of 3-ethyl 2,4-dihydrogen 1-phenyl-2,2,4-butanetricarboxylate were heated to 170° for 2 hours in a high vacuum and subsequently chromatographed on silica gel by means of a 10:1 mixture of methylene chloride and methanol, to obtain 600 mg (88%) of (RS)-4-(ethoxycarbonyl)-5-phenylvaleric acid as an oil which was used directly in the next step. MS: 250 (M+), 600 mg (2.4 mmol) of (RS)-4-(ethoxycarbonyl)-5-phenylvaleric acid in 20 ml of acetonitrile were treated with 1.06 g (2.4 mmol) of BOP, 310 mg of Hünig base and 0.21 ml of morpholine and stirred at room temperature for 1 hour and thereafter at 50° for 2 hours. After the usual working-up and chromatography on silica gel using a 10:1 mixture of methanol and chloroform as the eluting agent, there were obtained 400 mg (52%) of (RS)-α-[2-(morpholinocarbonyl)ethyl]hydrocinnamic acid ethyl ester which was used directly in the next step. MS: 319 (M+).

400 mg (1.25 mmol) of the above-named ester in 10 ml of ethanol were treated with 5 ml of 0.5N sodium hydroxide solution and subsequently stirred at 50° for 2 hours. After the usual working-up and chromatography on silica gel using a 10:1 mixture of methylene chloride and methanol there were obtained 170 mg (47%) of (RS)-α-[2-(morpholinocarbonyl)ethyl]hydrocinnamic acid as an oil which was used directly in the next step, MS: 291 (M+).

N-[(4-Biphenylmethyl)carbamoyl]-3-phenyl-L-alanine 3.9 g (21.3 mmol) of biphenylmethylamine[23] and 7.2 ml of Hünig base in 200 ml of toluene were treated while cooling in a ice bath with 10.5 ml of phosgene in toluene (20%) and stirred at 0° for 1 hour. Thereafter, 9 g of L-phenylalanine benzyl ester 4-toluenesulfonate were added and the solution was stirred at 80° for 12 hours. Subsequently, the mixture was partitioned between methylene chloride and water, the organic phase was dried over sodium sulfate, the solvent was removed under reduced pressure, and the product was isolated by chromatography on silica gel using a 10:1 mixture of methylene chloride and methanol, to obtain 7.3 g (74%) of N-[(4-biphenylmethyl)carbamoyl]-3-phenyl-L-alanine benzyl ester.
[23] A. Kamil et al., Czech. 163, 819 (1976)

3.2 g (6.7 mmol) of the above-named benzyl ester in 100 ml of ethanol were hydrogenated at room temperature in the presence of 320 mg of palladium-on-carbon until the theoretical amount of hydrogen had been taken up. Thereafter, the catalyst was filtered off, the filtrate was evaporated and the residue was crystallized from ethanol/methylene chloride/ether, to obtain 2.1 g (65%) of N-[(4-biphenylmethyl)carbamoyl]-3-L-alanine in the form of white crystals, melting point 169°–170°.

EXAMPLE 56

57 mg of N-[(1S,2S,4S)-1-(cyclohexylmethyl)-2-hydroxy-4-isopropyl-5-hexenyl]-α-(3-phenyl-L-alanyl-)imidazole-4-propionamide, 21 mg of t-butoxycarbonyl-L-azetidine-2-carboxylic acid, which was prepared from azetidinecarboxylic acid by t-butoxycarbonylation according to the method described by O. Keller et al. in Org. Synth. 63, 160, 1985, 47 mg of BOP and 0.021 ml of Hünig base in 5 ml of acetonitrile were stirred at room temperature for 8 hours and thereafter worked-up in the usual manner. The crude product was purified by chromatography on silica gel with a 10:1 mixture of methanol and chloroform, to obtain 69 mg of t-butyl [(S)-2-[(S)-α-[(S)-1-[[(1S,2S,4S)-1-(cyclohexylmethyl)-2-hydroxy-4-isopropyl-5-hexenyl]carbamoyl]-2-imidazol-4-ylethyl]-carbamoyl]phenethyl]carbamoyl]-1-azetidinecarboxylate in the form of white crystals. MS 721 (M+H)+.

EXAMPLE 57

56 mg of t-butyl [(s)-2-[(S)-α-[(S)-1-[[(1S,2S,4S)-1-(cyclohexylmethyl)-2-hydroxy-4-isopropyl-5-hexenyl]-carbamoyl]-2-imidazol-4-ylethyl]carbamoyl]phenethyl]-carbamoyl]-1-azetidinecarboxylate in 5 ml of ethanol were hydrogenated at room temperature for 2 hours in the presence of 10 mg of palladium-on-carbon. Thereafter, the catalyst was filtered off and the solvent was evaporated under reduced pressure, to obtain 47 mg of t-butyl (S)-2-[[(S)-α-[[(S)-1-[[(1S,2S,4S)-1-(cyclohexylmethyl) -2-hydroxy-4-isopropylhexyl]carbamoyl]-2-imidazol-4-ylethyl]carbamoyl]phenethyl]-carbamoyl]-1-azetidinecarboxylate in the form of white crystals. MS: 723 (M+H)+.

In an analogous manner by hydrogenating 90 mg of (S)-N-[(1S,2S,4S)-1-(cyclohexylmethyl)-2-hydroxy-4-isopropyl-5-hexenyl]-α-[(RS)-α-[(cyclopentylcarbonyl)-methyl]hydrocinnamamido]imidazole-4-propionamide there were obtained 78 mg of (S)-N-[(1S,2S,4S)-1-(cyclohexylmethyl)-2-hydroxy-4-isopropylhexyl]-α-[(RS)-α-[(cyclopentylcarbonyl)methyl]hydrocinnamamido]imdiazole-4-propionamide in the form of an amorphous solid as a 1:1 epimer mixture, MS: 635 (M+H)+.

EXAMPLE 58

The following compounds were prepared in a manner analogous to that described in Example 56:

From 75 mg of N-[(1S,2S,4S)-1-(cyclohexylmethyl)-2-hydroxy-4-isopropyl-5-hexenyl]-α-(3-phenyl-L-alanyl)imidazole-4-propionamide and 30 mg of (3R,8aR)-hexahydro-8a-methyl-5-oxo-5H-thiazolo-[3.2-a]pyridine-3-carboxylic acid[24], 64 mg (64%) of (S)-N--[(1S,2S,4S)-1-(cyclohexylmethyl)-2-hydroxy-4-isopropyl-5-hexenyl]-α-[(RS)-α-[(3R,8aR)-hexahydro-8a-methyl-5-oxo-5H-thiazolo-[3,2-a]pyridine-3-carboxamido]hydrocinnamamido]-imidazole-4-propionamide as a white solid, MS: 735 (M+H)+;
J. E. Baldwin et al., JACS 100, 4597

From 75 mg of N-[(1S,2S,4S)-1-(cyclohexylmethyl)-2-hydroxy-4-isopropyl-5-hexenyl]-α-(3-phenyl L-alanyl)imidazole-4-propionamide and 30 mg of (3R,7aR)-tetrahydro-7a-methylpyrrolo[2.1-b]-thiazole-3-carboxylic acid[24] 86 mg of (3R,7aR)-N-[(S)-α-[[(S)--1-[[(1S,2S,4S)-1--(cyclohexylmethyl)-2-hydroxy-4-isopropyl-5-hexenyl]carbamoyl]-2-imidazol-4-ylethyl]carbamoyl]-phenethyl]hexahydro-5-oxo-pyrrolo[2,1-b]thiazole-3-carboxamide as an amorphous solid, MS: 721 (M+H)+;
[24] J. E. Baldwin et al., JACS 100, 4597

From 75 mg of N-[(1S,2S,4S)-1-(cyclohexylmethyl)-2-hydroxy-4-isopropyl-5-hexenyl]-α-(3-phenyl-L-alanyl)imidazole-4-propionamide and 30 mg of N-t-butoxycarbonyl-L-methionine, 90 mg of t-butyl [(S)-1--[[(S)-α-[[(S)-1-[[(1S,2S,4S)-1-(cyclohexylmethyl)-2-hydroxy-4-isopropyl-5-hexenyl]-carbamoyl]-2-imidazol-4-ylethyl]carbamoyl]-phenethyl]carbamoyl]-2-(methylthio)ethyl] carbamate as an amorphous solid, MS: 769 (M+H)+;

From 75 mg of N-[(1S,2S,4S)-1-(cyclohexylmethyl)-2-hydroxy-4-isopropyl-5-hexenyl]-α-(3-phenyl-L-alanyl)imidazole-4-propionamide and 32 mg of N-isovaleryl-L-methionine which in turn was prepared by reacting L-methionine methyl ester with isovaleric acid chloride and subsequently saponifying of the methyl ester, 61 mg of (S)-N-[(1S,2S,4S)-1-(cyclohexylmethyl)-2-hydroxy-4-isopropyl-5-hexenyl]-α-[(S)-α-[(S)-4-(methylthio)-2-isovaleramidobutyramido]hydrocinnamamido]-imidazole-4-propionamide as an amorphous solid,

MS:753 (M+H)+.

EXAMPLE 59

A mixture of 95 mg of (RS)-α-[(2-morpholinoethyl)carbamoylmethyl]-1-naphthalenepropionic acid, 100 mg of (S)-α-amino-N-[(1S,2S,4S)-1-(cyclohexylmethyl)-2-hydroxy-4-isopropyl-5-hexenyl]imidazole-4-propionamide and 97 mg of HBTU in acetonitrile was stirred at room temperature for 3.5 hours and then worked-up in the usual manner. The residue was chromatographed on silica gel with a 4: mixture of methylene chloride and methanol as the eluting agent, to obtain 60 mg of N-[(1S,2S,4S)-1-(cyclohexylmethyl)-2-hydroxy-4-isopropyl-5-hexenyl]-α-[3-[(2-morpholinoethyl)carbamoyl]-2-(1-naphthylmethyl)propionamido]imidazole-4-propionamide as a foam. MS: 743 (M+H)+.

The (RS)-α-[(2-morpholinoethyl)carbamoylmethyl]-1-naphthalenepropionic acid used as the starting material was prepared as follows:

0.72 g of DCC was added to 1.0 g (3.5 mmol) of (RS)-3-(ethoxycarbonyl)-4-(1-naphthyl)butyric acid[25] in 50 ml of methylene chloride and the suspension obtained was stirred at room temperature for 2 hours. Subsequently, 0.46 ml (3.5 mmol) of 4-(2-aminoethyl)-morpholine was added and the mixture was stirred at room temperature for a further 18 hours. After usual working-up, the residue was flash chromatographed on silica gel with a 20:1 mixture of methylene chloride and methanol as the eluting agent, to obtain 0.5 g of (RS)-α-[(2-morpholinoethyl)carbamoylmethyl]-1-naphthalenepropionic acid ethyl ester in the form of a Pale yellow resin. MS: 398 (M)+.
[25] EPA 0.181.110

0.5 g (1.25 mmol) of the above-named ethyl ester in ethanol was treated with 2.5 ml of 1N sodium hydroxide solution and stirred at 80° for 6 hours. Thereafter, the reaction mixture was adjusted to pH 6 and the solvent was removed under reduced pressure. The residue was suspended in a 1:1 mixture of methylene chloride and methanol, the insoluble salts were filtered off, the filtrate was dried over sodium sulfate and the solvent was evaporated under reduced pressure. In this manner there were obtained 500 mg of (RS)-α-[(2-morpholinoethyl)carbamoylmethyl]-1-naphthalenepropionic acid in the form of a yellow foam which was used directly in the next step.

EXAMPLE 60

A mixture of 153 mg (0.4 mmol) of (S)-α-amino-N-[(1S,2S,4S)-1-benzyl-2-hydroxy-4-isopropyl-5-hexenyl-]Imidazole-4-propionamide, 98 mg of (R)-α-(pivaloylmethyl)hydrocinnamic acid, 175 mg of BOP and 0.14 ml of Hünig base in 10 ml of acetonitrile was stirred at room temperature for 12 hours and thereafter worked-up in the usual manner. Chromatography of the residue on silica gel using a 10:1 mixture of methylene chloride and methanol as the eluting agent yielded 120 mg of N-[(1S,2S,4S)-1-benzyl-2-hydroxy-4-isopropyl-5-hexenyl]-α-(α-pivaloylhydrocinnamamido)imidazole-4-propionamide as white crystals, MS: 615 (M+H)+.

The (S)-α-amino-N-[(1S,2S,4S)-1-benzyl-2-hydroxy-4-isopropyl-5-hexenyl]imidazole-4-propionamide used as the starting material was prepared as follows:

In a manner analogous to that described in Example 1 for the preparation of (αS,βS)-β-t-butoxycarbonylamino-α-[(S)-2-isopropyl-3-butenyl]cyclohexanepropanol, from 56.6 g (320 mmol) of (RS)-2-isopropyl-3-butenyl bromide 7.7 g of magnesium and 24.2 g of N-t-butoxycarbonyl-L-phenylalanal[26] there were obtained 15.6 g (49%) of t-butyl [(1S,2S,4S)-1-benzyl-2-hydroxy-4-isopropyl-5-hexenyl]carbamate as an epimer mixture. The desired (1S,2S,4S)-epimer was isolated as the less polar isomer. MS: 256 (M-benzyl)+, by flash chromatography on silica gel using a 9:1 mixture of methylene chloride and ether as the eluting agent.
[26] Evans et al., J. Org. Chem., 50, 4615 (1985) 2.2 g of t-butyl [(1S,2S,4S)-1-benzyl-2-hydroxy-b 4-isopropyl-5-hexenyl]carbamate were stirred at room temperature for 2 hours in 70 ml of 1.8N hydrogen chloride in dioxane. Thereafter, the reaction mixture was poured into sodium bicarbonate solution and extracted with ether at PH 3. Drying and evaporation of the ether extracts and chromatography of the residue on silica gel with a 5:1 mixture of methylene chloride and methanol yielded 900 mg (60%) of (2S,3S,5S)-2-amino-5-isopropyl-1-phenyl-6-hepten-3-ol as an oil, MS: 248 (M)+.

of 1.22 g (2.83 mmol) of N-α-N-im-di-t-butoxycarbonyl-L-histidine. 700 mg (2.83 mmol) of (2S,3S,5S)-2-amino-5-isopropyl-1-phenyl-6-hepten-3-ol, 1.25 g of BOP and 0.58 ml of Hünig base in 20 ml of acetonitrile was stirred at room temperature for 12 hours and thereafter worked-up in the usual manner. Chromatography of the residue on silica gel using a 2:1 mixture of methylene chloride and ether yields 1.0 g (10%) of t-butyl 4-[(S)-2-[[(1S,2S,4S)-1-benzyl-2-hydroxy-4-isopropyl-5-hexenyl]carbamoyl]-2-(1-t-butoxyformamido)ethyl]imidazole-1-carboxylate in the form of a foam, MS: 585 (M+H)+.

1 g (1.7 mmol) of t-butyl 4-[(S)-2-[[(1S,2S,4S)-1-benzyl-2-hydroxy-4-isopropyl-5-hexenyl]carbamoyl]-2-(1-t-butoxyformamido)ethyl]imidazole-1-carboxylate were dissolved in 7 ml of 5N hydrogen chloride in dioxane and subsequently stirred at room temperature for 2 hours. Thereafter, the reaction mixture was poured into sodium carbonate solution and extracted with ethyl acetate. The organic extract was dried and evaporated and the residue was chromatographed on silica gel with a 3:1 mixture of methylene chloride and methanol, to obtain 340 mg (52%) of (S)-α-amino-N-[(1S,2S,4S)-1-benzyl-2-hydroxy-4-isopropyl-5-hexenyl-]imidazole-4-propion-amide as a foam, MS; 385 (M+H)+.

EXAMPLE 61

120 mg of N-[(1S,2S,4S)-1-benzyl-2-hydroxy-4-isopropyl-5-hexenyl]-α-(α-pivaloylhydrocinnamamido)imidazole-4-propionamide in 10 ml of ethanol were hydrogenated at room temperature for 2 hours in the presence of 20 mg of palladium-on-carbon. Thereafter, the catalyst was filtered off and the solvent was evaporated under reduced pressure, to obtain (S)-N-[(1S,2S,4S)-1-benzyl-2-hydroxy-4-isopropylhexyl]-α-[(R)-α-(3,3-dimethyl-2-oxobutyl)hydrocinnamamido]imidazole-4-propionamide as a foam. MS: 617 (M+H)+.

EXAMPLE 62

A mixture of 256 mg (1.03 mmol) of (2S,3S,5S)-2-amino-5-isopropyl-1-phenyl-6-hepten-3-ol, 414 mg of Boc-Phe-His-OH. 0.354 ml of Hünig base and 455 mg of BOP in 20 ml of acetonitrile was stirred at room temperature for 12 hours and then worked-up in the usual manner. By flash chromatography of the residue on silica gel using a 7:1 mixture of methylene chloride and methanol, there were obtained 385 mg (61%) of t-butyl ((S)-α-[[(RS)-1-[[(1S,2S,4S)-1-benzyl-2-hydroxy-4-isopropyl-5-hexenyl]-carbamoyl]-2-imidazol-4-ylethyl]-carbamoyl]phenethyl] carbamate as a 4:1 epimer mixture. MS: 632 (M+H)+.

EXAMPLE 63

334 mg (0.53 mmol) of t-butyl [(S)-α-[[(RS)-1-[[(1S,2S,4S)-1-benzyl-2-hydroxy-4-isopropyl-5-hexenyl]-carbamoyl]-2-imidazol-4-ylethyl]carbamoyl]-phenethyl] carbamate were dissolved in 3 ml of 5.2N hydrogen chloride in dioxane and the mixture was stirred at room temperature for 2 hours. After the usual working-up, 100 mg of the crude product obtained were dissolved in 10 ml of acetonitrile. 40.4 ml (0.188 mmol) of t-butoxycarbonyl-D-proline, 0.064 ml of Hünig base and 83 mg of BOP were added, and the reaction mixture was subsequently stirred at room temperature for 12 hours. After the usual working-up the residue was chromatographed on silica gel using a 10:1 mixture of methylene chloride and methanol to obtain 78 ml (56%) of t-butyl (R)-2-[[(S)-α-[(RS)-1-[[[(1S,2S,4S)-1-benzyl-2-hydroxy-4-isopropyl-5-hexenyl]carbamoyl] -2-imidazol-4-ylethyl]carbamoyl]phenethyl]carbamoyl]1-pyrolidinecarboxylate in the form of white crystals as a 4:1 epimer mixture. MS: 729 (M+H)+.

EXAMPLE 64

0.65 g of (S)-α-amino-N-[(1S,2S,4RS)-2-hydroxy-1-isobutyl-4-isopropyl-5-hexenyl]imidazole-4-propionamide in 20 ml of acetonitrile were added together with 0.36 ml of ethyldiisopropylamine to a solution of 0.45 g of 2-benzyl-3-phenylpropionic acid (which was prepared according to the method described in J. Am. Chem. Soc. 71 1863 (1949)) and 0.8 g of BOP in 30 ml of acetonitrile and the mixture was stirred at room temperature for 20 hours. Subsequently, the reaction mixture was evaporated under reduced pressure, the residue was dissolved in 50 ml of ethyl acetate and the organic solution was washed twice with 100 ml of water each time, dried over sodium sulfate and evaporated. The residue Was separated by flash chromatography on 100 g of silica gel with a 250:15 mixture of methylene chloride and methanol as the eluting agent, to obtain there was obtained 0.17 g of (S)-α-(2,2-dibenzylacetamido)-N-[(1S,2S,4S)-2-hydroxy-1-isobutyl-4-isopropyl-5-hexenyl]imidazole-4-propionamide as a white powder, melting point 120°. This compound corresponds to the less polar isomer and has a Rf value of 0.14.

The (S)-α-amino-N-[(1S, 2S, 4RS)-2-hydroxy-1-isobutyl-4-isopropyl-5-hexenyl]imidazole-4-propionamide used as the starting material was prepared as follows:

0.72 g of (4S)-amino-(5S)-hydroxy-7-isopropyl-2-methyl-8-nonene in 20 ml of dimethylformamide were added together with 0.7 ml of ethyldiisopropylamine to a solution of 2 g of N-α-N-im-bis-Fmoc-L-histidine and 1.47 g of BOP in 20 ml of dimethylformamide and the mixture was stirred at room temperature for 20 hours. Subsequently, the reaction mixture was evaporated under reduced pressure, the residue was dissolved in 60 ml of ethyl acetate and the organic phase was washed twice with 200 ml of water each time, dried over sodium sulfate and evaporated. The crude product was purified by flash chromatography on 100 g of silica gel with a 250;20 mixture of methylene chloride and methanol as the eluting agent, to obtain 1.25 g of fluoren-9-ylmethyl [(S)-1-[[(1S,2S,4RS)-2-hydroxy-1-isobutyl-4-isopropyl -5-hexenyl]carbamoyl]-2-imidazol-4-ylethyl] carbamate as a white powder, MS: 573 (M+H)+.

1.25 q of fluoren-9-ylmethyl [(S)-1-[[(1S,2S,4RS)-2-hydroxy-1-isobutyl-4-isopropyl-5-hexenyl]carbamoyl]-2-imidazol-4-ylethyl] carbamate were dissolved in 20 ml of piperidine and stirred at room temperature for 3 hours. Thereafter, the reaction mixture was poured onto 20 ml of ice/water and filtered. Evaporation of the filtrate yielded 0.65 g of (S)-α-amino-N-[(1S,2S,4RS)-2-hydroxy-1-isobutyl-4-isopropyl-5-hexenyl]imidazole 4-propionamide as a white powder, Ms: 269 (M−C_4H_5N_2)+.

EXAMPLE 65

0.3 g of (S)-2-[[N-(t-butoxycarbonyl) 3-phenyl L-alanyl]oxy]succinamidic acid were dissolved together with 0.35 g of BOP in 20 ml of acetonitrile with the addition of 2 ml of dimethylformamide, treated with a solution of 0.17 g of (4S)-amino-(5S)-hydroxy-7-isopropyl 2-methyl-8-nonene and 0.15 ml of ethyldiisopropylamine in 20 ml of acetonitrile and stirred at room temperature for 20 hours. Subsequently, the reaction mixture was evaporated under reduced pressure and the residue was dissolved in 50 ml of methylene chloride. The organic solution was washed in succession with 50 ml of 3N hydrochloric acid, 50 ml of saturated sodium bicarbonate solution and 50 ml of saturated sodium chloride solution, dried over sodium sulfate and evaporated. The residue was purified by flash chromatography on 50 g of silica gel using a 10:1 mixture of methylene chloride and methanol as the eluting agent and subsequently crystallized from ether/methylene chloride. In this manner there was obtained 0.3 g of t-butyl [(S)-α-[[(S)-2-carbamoyl-1-[[(1S,2S,4RS) 2-hydroxy-1-isobutyl-4-isopropyl-5-hexenyl]carbamoyl]-ethoxy]carbonyl]phenethyl] carbamate as a white powder, melting point 75°.

The (4S)-amino-(5S)-hydroxy-7-isopropyl 2-methyl 8-nonene used as the starting material was prepared as follows:

0.8 g of t-butoxycarbonyl-L-phenylalanine was dissolved in 5 ml of pyridine, treated at −5° with 0.3 ml of oxalyl chloride and stirred at 0–5° for 10 minutes. After the addition of 0.7 g of benzyl-(S)-3-carbamoyl-2-hydroxypropionic acid (which was prepared according to the directions in Agr. Biol. Chem. 40, 1651 (1976) and Int. J. Peptide Protein Res. 20, 35 (1982)) in 1 ml of pyridine, the mixture was stirred at 0°–5° for 2 hours and thereafter at room temperature for 1 hour. The reaction mixture was then poured onto ice and extracted twice with 50 ml of ethyl acetate each time. The combined organic extracts were washed with 50 ml of 3N hydrochloric acid and 50 ml of saturated sodium bicarbonate solution, dried over sodium sulfate and evaporated. The residue was purified by flash chromatography on 50 g of silica gel using a 10:1 mixture of methylene chloride and methanol as the eluting agent to obtain there was obtained 0.9 g of (S)-2-[[N-(t-butoxycarbonyl)-3-phenyl-L-alanyl]oxy]succinamide benzyl ester as a yellow powder. MS: 397 (M—C_4H_9O)+.

0.9 g of the above benzyl ester was dissolved in 40 ml of ethanol and hydrogenated at normal pressure in the presence of 0.1 g of palladium-on-carbon (10%). After completion of the hydrogen uptake, the catalyst was filtered off and the filtrate was evaporated. Crystallization of the residue from methylene chloride yielded 0.52 g of (S)-2-[[N-(t-butoxycarbonyl)-3-phenyl-L-alanyl]oxy]succinamidic acid as a white powder, MS: 381 (M+H)+.

EXAMPLE 66

A solution of 200 mg of (2S,3S,5S)-2-[Boc-His(3-Bom)-Pro-His-NH]-1 cyclohexyl-5-isopropyl-6-hepten-3-ol was hydrogenated exhaustively at room temperature in a 4:1 mixture of glacial acetic acid and water, in the presence of 20 mg of palladium-on-carbon (10%). After completion of the hydrogen uptake (4 hours), the catalyst was filtered off and the filtrate was evaporated to dryness. The crystals obtained after chromatographic purification on silica gel were recrystallized from ethyl acetate/hexane, to obtain there was obtained (2S,3S,5S)-2-(Boc-His-Pro-His-NH)-1-cyclohexyl-5-isopropyl-3-heptanol in 69% yield, melting point 135°-136°.

The preparation of the (2S,3S,5S)-2-[Boc-His(3-Bom)-Pro-His-NH]-1-cyclohexyl 5-isopropyl-6-hepten-3-ol used as the starting material was described in Example 68.

EXAMPLE 67

A solution of 100 mg of (S)-α-[[N-(t-butoxycarbonyl)-β-phenyl-L-alanyl]oxy]imidazole-4-propionic acid, 78 mg of (αS,βS)-β-amino-α-[(S)-2-isopropyl-3-butenyl]cyclohexanepropanol and 55 mg of N-methylmorpholine in 3 ml of dimethylformamide was treated with 102 mg of HBTU while stirring and passage therethrough with argon. After allowing to stand overnight, the reaction solution was poured into 5 ml of concentrated aqueous sodium bicarbonate solution and extracted with ethyl acetate. The organic extracts were dried and evaporated under reduced pressure and the crude product obtained in purified by chromatography on silica gel with a 95:5 mixture of methylene chloride and methanol as the eluting agent, to obtain t-butyl [(S)-α-[[(S)-1-[[(1S,2S,4S)-1-(cyclo- hexylmethyl) -2-hydroxy-4-isopropyl-5-hexenyl]carbamoyl]-2-imidazole-4-ylethoxy]carbonyl]phenethyl] carbamate was obtained in 22% yield, melting point 72°-75° (dec.).

The (S)-α-[[N-(t-butoxycarbonyl)-β-phenyl-L-alanyl]oxy]imidazole-4-propionic acid used as the starting material was prepared as follows:

1.99 g of N-t butoxycarbonyl-L-phenylalanine and 1.58 g of benzyl (S)-α-hydroxyimidazolepropionate were suspended in 25 ml of methylene chloride and stirred. After stirring at room temperature for 15 minutes, 305 mg of 4-dimethylaminopyridine were added and the reaction mixture was cooled to −15°. After the dropwise addition of 2 ml of N-methylmorpholine and a solution of 6.6 g of propanephosphoric acid anhydride in 5 ml of methylene chloride, the reaction mixture was stirred at −15° for an additional 2 hours and left to stand at −18° for 6 days. After the addition of a few drops of water, the reaction mixture was evaporated under reduced pressure and the oily residue was triturated for 2 hours with 100 ml of ethyl acetate and 25 ml of water. The organic phase was then washed in succession with aqueous sodium bicarbonate solution (5%) water and 1.5M citric acid. The colorless oil obtained after evaporation of the solvent under reduced pressure was chromatographed on silica gel using a 95:5 mixture of methylene chloride and methanol as the eluting agent, to obtain (S)-α-[[N-(t-butoxycarbonyl) 3-phenyl-L-alanyl] oxy]imidazole-4-propionic acid benzyl ester as a yellow oil in 13% yield, MS: 494 (M+H)+.

A solution of 960 mg of the above-described benzyl ester in 20 ml of absolute ethanol was hydrogenated in the presence of 500 mg of palladium-on-carbon (10%) until the theoretical amount of hydrogen had been taken up. Thereafter, the catalyst was filtered off and the filtrate was evaporated under reduced pressure, to obtain an oily residue which crystallized after the addition of methanol/ethyl acetate. In this manner there was obtained (S)-α-[[N-(t-butoxycarbonyl)-β-phenyl-L-alanyl]oxy]imidazole-4-propionic acid in 18% yield, melting point 130°-131°.

EXAMPLE 68

The following compounds were prepared in an analogous manner to that described in Example 67:

From (S)-α-amino-N-[(1S,2S,4S)-1(cyclohexylmethyl)-2-hydroxy-4-isopropyl-5-hexenyl]imidazole-4-propionamide and N-(t-butoxycarbonyl)-3-(1-naphthyl)-L-alanine in 50% yield, t-butyl [(S)-1-[[(S)-1-[[(1S,2S,4S)-1-(cyclohexylmethyl) 2-hydroxy-4-isopropyl-5-hexenyl]carbamoyl]-2-imidazol-4-ylethyl]carbamoyl]-2-(1-naphthyl)ethyl] carbamate, melting point 141°-143° (from ethyl acetate/hexane);

From (S)-α-amino-N-[(1S,2S,4S)-1(cyclohexylmethyl)-2-hydroxy-4-isopropyl 5-hexenyl]imidazole-4-propionamide and N-(t-butoxycarbonyl)-4-chlorophenylalanine in 41% yield, t-butyl [(S)-1-[[(S)-1-[[(1S,2S,4S)-1-(cyclohexylmethyl)-2-hydroxy-4-isopropyl-5-hexenyl]carbamoyl]-2-imidazol- 4-ylethyl]carbamoyl]-2-(4-chlorophenyl)ethyl] carbamate, melting point 220°-221° (from ethanol/ethyl acetate);

From (S)-α-amino-N-[(1S,2S,4S)-1-(cyclohexylmethyl)-2-hydroxy-4-isopropyl-5-hexenyl]imidazole-4-propionamide and N-t-butoxycarbonyl L-phenylglycine in 39% yield, t-butyl [(S)-α-[[(S)-1-[[(1S,2S,4S)-1-(cyclohexylmethyl)-2-hydroxy-4-isopropyl-5-hexenyl]-carbamoyl]-2-imidazol-4-yl-ethyl]carbamoyl]benzyl] carbamate, melting point 125°-126° (from ethyl acetate/hexane);

From (S)-α-amino-N-[(1S,2S,4S)-1-(cyclohexylmethyl)-2-hydroxy-4-isopropyl 5-hexenyl]imidazole-4-propionamide and N-t-butoxycarbonyl-L-cyclohexylglycine in 54%. yield t-butyl [(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]cyclohexylmethyl] carbamate, melting point 139°-140° (from ethyl acetate/hexane);

From (S)-α-amino-N-[(1S,2S,4S)-1-(cyclohexylmethyl)-2-hydroxy-4-isopropyl 5-hexenyl]imidazole-4-propionamide and t-butoxycarbonyl-D-phenylalanine in 48% yield, t-butyl [(R)-α-[[(S) 1-[[(1S,2S,4S)-1-(cyclohexylmethyl)-2-hydroxy 4-isopropyl-5-hexenyl]carbamoyl]-2-imidazol-4-ylethyl]carbamoyl]phenethyl] carbamate, melting point 195° (from ethyl acetate);

From (S)-α-amino-N-[(1S,2S,4S)-1-(cyclohexylmethyl)-2-hydroxy-4-isopropyl-5 hexenyl]imidazole-4-propionamide and t-butoxycarbonyl-L-cyclohexylalanine in 22% yield, t-butyl [(S)-2-cyclohexyl-1-[[(S)-1-[[(1S,2S,4S)-1-(cyclohexylmethyl)-2-hydroxy-4-isopropyl-5-hexenyl]carbamoyl](2-imidazol-4-ylethyl]carbamoyl]ethyl] carbamate, melting point 116° (from ethyl acetate/diisopropyl ether);

From N-[(1S,2S,4S)-1-(cyclohexylmethyl)-2-hydroxy-4-isopropyl-5-hexenyl]-α-(3-phenyl-L-alanyl- )imidazole-4-propionamide and N-[5-(1-t-butoxyformamido)valeryl]-β-alanine in 40% yield, t-butyl [4-[[-2-[[(S)-α-[[(S)-1-[[(1S,2S,4S)-1-(cyclohexylmethyl)-2-hydroxy-4-isopropyl-5-hexenyl]carbamoyl]-2-imidazol 4-ylethyl]-carbamoyl]phenethyl]carbamoyl]ethyl]carbamoyl]-butyl] carbamate, melting point 114°–115° (from ethyl acetate);

From (S)-α-amino-N-[(1S,2S,4S)-1-(cyclohexylmethyl)-2-hydroxy-4-isopropyl 5-hexenyl]imidazole-4-propionamide and Boc-His(3-Bom)-Pro-OH in 51% yield, (2S,3S,5S)-2-[Boc-His(3-Bom) Pro-His-NH]-1-cyclohexyl-5-isopropyl-6-hepten-3-ol, melting point 121°–122° (from ethyl acetate/hexane).

The acids used as the starting materials were either known and commercially available or were prepared as follows:

N-[5-(I-t-Butoxyformamido)valeryl]-β-alanine

To a suspension of 7.68 g of β-alanine ethyl ester hydrochloride in 50 ml of methylene chloride there was added, with stirring, 5.56 g of triethyl- amine. 10.86 g of N-t-butoxycarbonyl-5-aminovaleric acid, dissolved in 50 ml of methylene chloride, and portionwise 11.35 g of DCC, in that order. After completion of the addition, the reaction mixture was stirred at room temperature overnight and filtered off from separated urea. The filtrate was washed in succession with 250 ml of sodium bicarbonate solution (5%), water, 250 ml of 0.1M citric acid and, finally, with saturated sodium chloride solution. Thereafter, the solvent was evaporated under reduced pressure and the oily residue was purified by column chromatography on silica gel, to obtain N-[5-(1-t-butoxyformamido)valeryl]-β-alanine ethyl ester in 59% yield, melting point 28° (from hexane).

3.94 g of this ester were dissolved in 20 ml of methanol and, while stirring at 0°, 1 mol equivalent and after 30 minutes a further 0.2 mol equivalents of 1N sodium hydroxide solution were added. The mixture was then stirred at room temperature for one hour, 1.2 mol equivalents of 1N hydrochloric acid (PH 4) were added portionwise, the solvent was evaporated under reduced pressure and the aqueous phase was extracted several times with methylene chloride. Drying and evaporation of the extracts yielded an oily residue which crystallized upon the addition of hexane. Recrystallization from hexane yielded N-[5-(1-t-butoxyformamido)-valeryl]-β-alanine in 87% yield, melting point 70°.

EXAMPLE 69

5 ml of a 4 molar solution of hydrogen chloride in dioxane were added to 1.06 g (3 mmol) of t-butyl [(1S,2S,4S)-4-(2-furyl)-2-hydroxy-1-isobutyl-5-methylhexyl] carbamate in 8 ml of acetic acid. After 30 minutes the solvent was evaporated under reduced pressure, the residue was digested with toluene, and the solvent was again evaporated. The residue was dissolved in 10 ml of absolute dimethylformamide and 1.8 g (3 mmol) of N-α-N-im-bis-Fmoc-L-histidine in 10 ml of tetrahydrofuran, 0.35 ml of N-methylmorpholine and 0.8 g (5.6 mmol) of N-hydroxybenzotriazole were added to the solution. The resulting solution was cooled to −10° and treated dropwise with 5 ml of a 1 molar DCC solution in tetrahydrofuran. The reaction mixture was stirred overnight and filtered. The solution was treated with 5 ml of a 50% piperidine-dimethylformamide solution and, after 30 minutes, evaporated in a high vacuum. The residue was dissolved in ether and the organic phase was washed in succession with water, a sodium carbonate solution and again with water. The organic phase was dried over sodium sulfate and evaporated under reduced pressure. The residue was then dissolved in 10 ml of dimethylformamide and 0.8 g (3 mmol) of N-t-butoxycarbonyl-phenylalanine in 10 ml of tetrahydrofuran, 0.35 ml of N-methylmorpholine, 0.8 g (5.6 mmol) of N-hydroxybenzotriazole and 5 ml of a 1 molar DCC solution in tetrahydrofuran were added. The reaction mixture was stirred overnight and filtered. The filtrate was evaporated in a high vacuum and the residue was dissolved in ether. The organic solution was washed with water, a sodium carbonate solution and once more with water, dried over sodium sulfate and evaporated under reduced pressure. For purification, the residue was chromatographed with a 19:3 mixture of methylene chloride and ethyl acetate as the eluting agent, to obtain 0.65 g of (S,S,S)-1-(Boc-Phe-His-NH)-methylbutyl-γ-isopropyl-2-furane-propanol as a thick oil. MS: 638 $(M+H)^+$.

The t-butyl [(1S,2S,4S)-4-(2-furyl)-2-hydroxy-1-isobutyl-5-methylhexyl] carbamate used as the starting material was prepared as follows:

340 g (2.5 mmol) of zinc chloride were added in one portion to a solution of 217 g (1.67 mol) of 2,5-dimethoxy-2,5-dihydrofuran, 1500 ml (10 mol) of malonic acid diethyl ester, 167 ml of Water and 330 ml of glacial acetic acid. The temperature rose to 35°. The dark solution was stirred at room temperature overnight, poured onto ice, extracted three times with diethyl ether, washed in succession with saturated sodium bicarbonate and sodium chloride solutions, and finally dried. After evaporating the excess malonic acid diethyl ester (70°/13 Pa), the remaining oil was distilled over a Vigreux column, to obtain 109.2 g (29%) of 2-furylmalonic acid diethyl ester (purity 94%), boiling point 100°–110°/39 Pa.

24 g (1 mol) of sodium hydride were suspended in 100 ml of absolute tetrahydrofuran. A solution of 218.4 g (0.97 mol) of 2-furylmalonic acid diethyl ester in 200 ml of absolute tetrahydrofuran was added dropwise. The temperature rose to 30° (blue suspension). After stirring at 30° for 30 minutes, 340 g (200 ml; 2 mol) of isopropyl iodide were added dropwise within 30 minutes. The reaction mixture was heated to reflux overnight, thereafter evaporated under reduced pressure, and dissolved in ether. After evaporation of the solvent, the remaining oily residue was distilled in a high vacuum, to obtain 240.6 g (92.5%) of 2-furyl-2-isopropylmalonic acid diethyl-ester (purity 93.6%) in the form of a yellowish oil, boiling point 85°–88°/13 Pa.

240.6 g (0.9 mol) of 2-furyl-2-isopropylmalonic acid diethyl ester were dissolved in 500 ml of dimethyl sulfoxide, treated with 2000 ml of 2N sodium hydroxide solution and heated to reflux for 2 hours. After cooling, o the reaction mixture was poured into dilute sulfuric acid and extracted exhaustively with ether. The organic extracts were thereafter dried and the solvent was evaporated under reduced pressure, to obtain 148.7 g (98%) of (±) 2-(2-furyl)-3-methyl- butyric acid in the form of a thick yellowish oil.

161.0 g (0.96 mol) of (±) 2-(2-furyl)-3-methylbutyric acid were dissolved in 1000 ml of ether and treated with 109 g (0.9 mol) of S(−)-α-phenylethylamine in 100 ml of ether. The separated crystals were filtered off and recrystallized three times from 600 ml of ethyl acetate, to obtain 80 g of white crystals, melting point 135°–136°, $[\alpha]_D^{20} = -14.1°$ (c=2%. methanol).

The crystals were suspended in ethyl acetate and acidified with a 3N hydrochloric acid solution while cooling with ice. The organic solution was washed with water, dried and evaporated under reduced pressure, to obtain 46.7 g of (+) 2-(2-furyl)-3-methylbutyric acid as a viscous oil (purity 98.6%), $[\alpha]_D^{20} = +29.9°$ (c=1%, ethyl acetate).

The mother liquors from the above crystallizations were pooled and the free acid was isolated as described, dissolved in 1000 ml of ether and treated with the corresponding amount of R-(+)-α-phenylethylamine. After three-fold recrystallization from ethyl acetate, there were obtained 80.3 g of white crystals of melting point 135°-136°, $[\alpha]_D^{20} = +15.0°$ (c=1%, methanol).

Conversion of this salt according to the procedure described above yielded 45.0 g of (−)2-(2-furyl)-3-methylbutyric acid as a viscous oil of 99.5% purity. $[\alpha]_D^{20} = -31.1°$ (c=1%, ethyl acetate).

10.5 g (0.277 mol) of lithium aluminium hydride were suspended in 100 ml of absolute ether and treated while stirring within 10 minutes with 100 ml of absolute tetrahydrofuran. To this stirred suspension was added dropwise within 6–8 hours, while heating to reflux, 46.7 g (0.277 mol) of (+) 2-(2-furyl)-3-methylbutyric acid in 100 ml of absolute tetrahydrofuran. The reaction mixture was cooled and treated slowly with a 3N hydrochloric acid solution. The organic phase was separated, washed with water, dried and evaporated under reduced pressure. The remaining oil was distilled in a high vacuum, to obtain 32 g (75%) of (R)-(+)-2-(2-furyl)-3-methyl-1-butanol as a colorless liquid of 96% purity, boiling point 58°/39 Pa, $[\alpha]_D^{20} = +2.5°$ (c=1%, ethanol).

121.7 g (0.464 mol) of triphenylphosphine were added portionwise within 8 hours to a solution of 17.8 g (0.1154 mol) of (R)-(+)-2-(2-furyl)-3-methyl-1-butanol in 150 ml of carbon tetrachloride. After stirring the reaction mixture for 24 hours, 500 ml of pentane were added and the precipitate formed was filtered off. After evaporation of the solvent, the residue was dissolved in pentane and purified by chromatography on silica gel, to obtain 5 g (92%) of 2-[(S)-(−)-1-(chloromethyl)-2-methylpropylfuran which was used directly in the next step.

A solution of 14.6 g (0.084 mol) of 2-[(S)-(−)-1-(chloromethyl)-2-methylpropylfuran in 46 ml of ether were slowly added, dropwise, to a suspension of 3.22 g of magnesium in 12 ml of ether. The reaction mixture was stirred vigorously at room temperature overnight and thereafter cooled to −70°. 8.3 g (0.038 mol) of t-butoxycarbonyl-L-leucinal in 40 ml of ether were added dropwise. After completion of the addition, the reaction mixture was allowed to stand at 0° for 1 hour. Thereafter, 100 ml of a saturated ammonium chloride solution were added, the organic phase was dried over magnesium sulfate, and the solvent was evaporated under reduced pressure. The residue obtained (16 g) was chromatographed on silica gel with a 1:4 mixture of ether and hexane, to obtain 4.8 g of t-butyl [(1S,2S,4S)-4-(2-furyl)-2-hydroxy-1-isobutyl-5-methylhexyl] carbamate which was used directly in the next step.

EXAMPLE 70

In an analogous manner to that described in Example 69, from t-butyl [(1S,2S,4S)-2-hydroxy-1-isobutyl-5-methyl-4-phenylhexyl] carbamate there was obtained [4S,5S,7S]-4-(Boc-Phe-His-NH)-2,8-dimethyl-7-phenyl-5-nonanol in the form of a thick oil. MS: 648 (M+H)+.

The t-butyl [(1S,2S,4S)-2-hydroxy-1-isobutyl-5-methyl-4-phenylhexyl] carbamate used as the starting material was prepared as follows:

23 g of sodium in small portions were added at −35° within 90 minutes to 1500 ml of liquid ammonia. After completion of the addition, 150 mg of iron-(III) nitrate.9H2O were added. To this suspension were added, while stirring vigorously, 150 g (1 mol) of phenylacetic acid methyl ester in 500 ml of absolute tetrahydrofuran and, half an hour later, 100 ml (1 mol) of isopropyl iodide were added dropwise. After completion of the addition, the ammonia was distilled off overnight. Water was added slowly to the liquid residue and the mixture was extracted with ether. The organic extracts were washed with water, dried over sodium sulfate and evaporated under reduced pressure, to obtain 165.8 g (87%) of 2-phenyl-3-methylbutyric acid methyl ester as a yellow oil which was used directly in the next step.

A solution of 165.8 g (0.87 mol) of 2-phenyl-3-methylbutyric acid methyl ester, 52.0 q (1.30 mol) of sodium hydroxide, 1200 ml of methanol and 600 ml of water was heated to reflux for one hour. After evaporation of the methanol under reduced pressure, dilution with water and acidification with conc. hydrochloric acid, the aqueous solution was extracted with ether. The ethereal extracts were washed with water, dried over sodium sulfate and evaporated under reduced pressure, to obtain 146.3 g (95%) of 2-phenyl-3-methylbutyric acid in the form of a yellow oil which was used directly in the next step.

A solution of 146.3 g (0.82 mol) of rac. 2-phenyl-3-methylbutyric acid in 820 ml of acetonitrile was treated with 78.5 ml (0.615 mol) of (S)-(−)-α-phenylethylamine. The resulting crystals were filtered off and washed with acetonitrile. After three-fold recrystallization from acetonitrile, there were obtained 88.5 g of (+)-2-phenyl 3-methylbutyric acid as the α-phenylethylammonium salt, melting point 198°-200°, $[\alpha]_D^{20} = +4.3°$ (c=1%, methanol). This salt was suspended in 1000 ml of ethyl acetate and treated with 3N hydrochloric acid while cooling with ice. The ethyl acetate extracts were washed with water, dried over sodium sulfate and evaporated under reduced pressure, to obtain 54.5 g of (S)-(+)-2-phenyl-3-methylbutyric acid as a light yellowish oil, $[\alpha]_D^{20} = +61.3°$ (c=1%, chloroform).

A suspension of 19.5, g (0.51 mol) of lithium aluminium hydride in 750 ml of absolute ether was heated to reflux. Within 4 hours there was added, dropwise, a solution of 54.5 g (0.307 mol) of (S)-(+)-2-phenyl 3-methylbutyric acid in 250 ml of absolute ether. After heating to reflux for a further 2 hours, the suspension was treated carefully with 1N hydrochloric acid and the ether phase was washed with water, dilute sodium bicarbonate solution, and once more with water. After drying the organic phase over sodium sulfate and evaporation under reduced pressure, there were obtained 53.1 g of (S)-(+)-2-phenyl-3-methylbutanol as a thick oil which was used directly in the next step.

A solution of 49.3 g (0.3 mol) of (S)-(+) 2-phenyl-3-methylbutanol in 400 ml of absolute methylene chloride was treated with 80 g (0.3 mol) of triphenylphosphine. Thereafter, 53.4 g (0.3 mol) of N-bromosuccinimide were added portionwise while stirring vigorously. After 16 hours, the reaction mixture was filtered and the filtrate was evaporated under reduced pressure. The residue was dissolved in hexane and purified by chromatography on silica gel, to obtain in this manner 34.9 g (51%) of (S)-(−)-2-phenyl-3-methylbromobutane as a volatile oil, $[\alpha]_D^{20}=-19.6°$ (c=1%. chloroform).

A solution of 40.9 g (0.18 mol) of (S)-(−)-2-phenyl-3-methylbromobutane in 110 ml of tetrahydrofuran and 0.5 ml of 1,2-dibromoethane was slowly added dropwise to a suspension of 6.6 g of magnesium in 25 ml of ether. The temperature rose to 50°. Thereafter, the reaction mixture was stirred at 50° for a further 2 hours and then cooled to −50°. Then, a solution of 13 g (0.06 mol) of N-t-butoxycarbonyl-L-leucinal in 40 ml of tetrahydrofuran was added slowly. After 16 hours at room temperature, the reaction mixture was treated with 200 ml of a 20% ammonium chloride solution. The organic phase was dried over magnesium sulfate and the solvent was evaporated under reduced pressure. The residue (24.3 g) was chromatographed on silica gel with a 4:1 mixture of hexane and ether, to obtain 9.3 g of t-butyl [(1S,2S,4S)-2-hydroxy-1-isobutyl-5-methyl-4-phenylhexyl]carbamate which has a melting point of 95°-96° after crystallization from hexane.

EXAMPLE 71

The following compounds were prepared in a manner analogous to that described in Example 1:

From 78 mg (0.20 mmol) of (S)-α-amino-N-[(1S,2S,4S)-1-(cyclohexylmethyl)-2-hydroxy 4-isopropyl-5-hexenyl]imidazole-4-propionamide and 57 mg (0.24 mmol) of ethoxycarbonyl-L-phenyl-alanine, 57 mg of (2S,3S,5S)-1-cyclohexyl 2-[(ethoxycarbonyl)-Phe-His-NH]-5-isopropyl 6-hepten-3-ol in the form of a solid, MS: 610 (M+H)+;

From 78 mg (0.20 mmol) of (S)-α-amino-N-[(1S,2S,4S)-1-(cyclohexylmethyl)-2-hydroxy-4-isopropyl-5-hexenyl]imidazole-4-propionamide and 70.8 mg (0.25 mmol) of phenylacetyl-L-phenyl-alanine, 97 mg of (2S,3S,5S)-1-cyclohexyl-2-[(phenylacetyl)-Phe-His-NH]-5-isopropyl-6-hepten-3-ol in the form of a solid, MS: 656 (M+H)+;

From 78 mg (0.20 mmol) of (S)-α-amino-N-[(1S,2S,4S)-1-(cyclohexylmethyl)-2-hydroxy-4-isopropyl-5-hexenyl]imidazole-4-propionamide and 68 mg (0.25 mmol) of 2-pyridylcarbonyl-L-phenylalanine, 88 mg of 1-cyclohexyl-5-isopropyl 2 [(2-pyridylcarbonyl)-(Phe-His-NH]-6-hepten-3 ol as a solid, MS: 643 (M+H)+;

From 78 mg (0.20 mmol) of (S)-α-amino-N-[(1S,2S,4S)-1-(cyclohexylmethyl)-2-hydroxy-4-isopropyl-5-hexenyl]imidazole-4-propionamide and 75 mg (0.25 mmol) of 2-phenylacetyl L-tyrosine, 110 mg of (2S,3S,5S)-1-cyclohexyl-5-isopropyl-2-[(phenylacetyl)-Tyr-His-NH]-6-hepten-3-ol as a solid, MS: 672 (M+H)+;

From 78 mg (0.20 mmol) of (S)-α-amino-N-[(1S,2S,4S)-1-(cyclohexylmethyl)-2-hydroxy-4-isopropyl-5-hexenyl]imidazole-4-propionamide and 72 mg (0.25 mmol) 2-pyridylcarbonyl L-tyrosine, 96 mg of (2S,3S,5S)-1-cyclohexyl-5-isopropyl-2-[(2-pyridylcarbonyl)-Tyr-His-NH]-6-hepten 3-ol as a solid, MS: 659 (M+H)+;

From 175 mg (0.45 mmol) of (S)-α-amino-N-[(1S,2S,4R)-1-(cyclohexylmethyl)-2-hydroxy-4-isopropyl-5-hexenyl]imidazole-4-propionamide and 145 mg (0.5 mmol) of 2-pyridylcarbonyl-L-tyrosine, 150 mg of (S)-N-[(1S,2S,4R)-1-(cyclohexylmethyl)-2-hydroxy-4-isopropyl-5-hexenyl]-α-[(S)-p-hydroxy-α-picolinamidohydrocinnamido]imidazole-4-propionamide as a solid. MS: 659 (M+H)+;

From 175 mg (0.45 mmol) of (S)-α-amino-N-[(1S,2S,4R)-1-(cyclohexylmethyl)-2-hydroxy-4-isopropyl-5-hexenyl]imidazole-4-propionamide and 150 mg (0.5 mmol) of phenylacetyl-L-tyrosine, 150 mg of (S)-N-[(1S,2S,4R)-1-(cyclohexylmethyl)-2-hydroxy-4-isopropyl-5-hexenyl]-α-[(S)-p-hydroxy-α-(2-phenylacetamido)hydrocinnamamido]-imidazole-4-propionamide as a solid, MS: 672 (M+H)+;

From 175 mg (0.45 mmol) of (S)-α-amino-N-[(1S,2S,4R)-1-(cyclohexylmethyl)-2-hydroxy-4-isopropyl-5-hexenyl]imidazole-4-propionamide and 137 mg (0.5 mmol) of 2-pyridylcarbonyl-L-phenylalanine. 150 mg of (S)-N-[(1S,2S,4R)-1-(cyclohexylmethyl)-2-hydroxy-4-isopropyl-5-hexenyl]-α-[(S)-α-picolinamidohydrocinnamamido]imidazole-4-propionamide as a solid, MS: 643 (M)+;

From 175 mg (0.45 mmol) of (S)-α-amino-N-[(1S,2S,4R)-1-(cyclohexylmethyl)-2-hydroxy-4-isopropyl-5-hexenyl]imidazole-4-propionamide and 141 mg (0.50 mmol) of phenylacetyl-L-phenylalanine, 150 mg of (S)-N-[(1S,2S,4R)-1-(cyclohexylmethyl) 2-hydroxy-4-isopropyl-5-hexenyl]-α-[(S)-α-(2-phenylacetamido)-hydrocinnamamido)imidazole-4-propionamide as a solid, MS: 656 (M+H)+;

From 107 mg (0.20 mmol) of N-[(1S,2S,4S)-1-(cyclohexylmethyl)-2-hydroxy-4-isopropyl 5-hexenyl]-α-(3-phenyl-L-alanyl)imidazole-4-propionamide and 66 mg of 1-(imidazolyl)-3-propionyl-D-proline, 126 mg of (S)-N-[(1S,2S,4S)-1-(cyclohexylmethyl)-2-hydroxy-4-isopropyl-5-hexenyl]-α-[(S)-α-[(R)-1-[3-(1H-imidazol-1-yl)propionyl]-2-pyrrolidinecarboxamido]hydrocinnamamido]]imidazole-4-propionamide as a solid, MS: 757 (M+H)+;

From 111 mg (0.20 mmol) of (S)-α-[p-fluoro-L-alanyl)amino]-N-[(1S,2S, 4S)-1-(cyclohexylmethyl)-2-hydroxy-4-isopropyl-5-hexenyl]imidazole-4-propionamide and 47.8 mg (0.24 mmol) of 2-(2-pyridyl)benzoic acid. 120mg of (S)-N-[(1S,2S,4S)-1-(cyclohexylmethyl)-2-hydroxy-4-isopropyl-5-hexenyl]-α-[(S)-α-[2-(2-pyridyl)benzamido]-p-fluoro(hydcocinnamamido)-]imidazole-4-propionamide as a solid, Ms: 737 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 75 mg (0.24 mmol) of Boc-D-Pro-Pro-OH, 122 mg of (2S,5S)-2-(Boc-D-Pro-Pro-Phe-His-NH)-1-cyclohexyl-5-isopropyl-6-hepten-3-ol as a solid, MS: 832 (M+H)+.

From 269 mg (0.6 mmol) of N-[(1S,2S,4R)-1-(cyclohexylmethyl)-2-hydroxy-4-isopropyl-5-hexenyl]-α-(3-phenyl-L-alanyl)imidazole-4-propionamide and 187 mg (0.6 mmol) of Boc-D-Pro-Pro-OH, 400 mg of t-butyl (R)-2-[[(S)-2-[[(S)-α-[[(S)-1-[[(1S,2S,4R)-1-(cyclohexylmethyl)-2-hydroxy-4-isopropyl-5-hexenyl]carbamoyl]-2-imidazol-4-ylethyl]carbamoyl]-phenethyl]carbamoyl]-1-pyrrolidinyl]carbonyl]-1-pyrrolidinecarboxylate as a solid, MS: 832 (M+H)+.

From 269 mg (0.5 mmol) of N-[(1S,2S,4R)-1-(cyclohexylmethyl)-2-hydroxy-4-isopropyl-5-hexenyl]α-(3-phenyl-L-alanyl)imidazole-4-propionamide and 260mg (0.6 mmol) of t-butoxycarbonyl D-phenylglycine, 110 mg of t-butyl [[(R)-α-[[(S)-α-[[(S)-1-[[(1S,2S,4R)-1-(cyclohexylmethyl)-2-hydroxy-4-isopropyl-5-hexenyl]carbamoyl]-2-imidazol-4-ylethyl]carbamoyl]phenethyl]carbamoyl]benzyl]carbamate as a solid, MS 771(M+H)+.

From 269 mg (0.5 mmol) of N-[(1S,2S,4R)-1-(cyclohexylmethyl)-2-hydroxy-4-isopropyl-5-hexenyl]-α-

(3-phenyl-L-alanyl)imidazole-4-propionamide and 119 mg (0.6 mmol) of 2-(2-pyridyl)benzoic acid. 290 mg of (S)-N-[(1S,2S,4R)-1-(cyclohexylmethyl)-2-hydroxy-4-isopropyl-5-hexenyl]-α-[(S)-α-[2-(2-pyridyl)benzamido]hydrocinnamamido]imidazole-4-propionamide as a solid, MS: 719 (M+H)+.

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 75 mg (0.24 mmol) of Boc-Pro-Pro-OH, 137 mg of (2S,3S,5S)-2-(Boc-Pro-Pro-Phe-His-NH)-1-cyclohexyl-5-isopropyl-6-hepten-3-ol as a solid. MS: 832 (M+H)+;

From 107 mg (0.20 mmol) of N-[(1S,2S,4R)-1-(cyclohexylmethyl)-2-hydroxy-4-isopropyl-5-hexenyl]-α-(3-phenyl-L-alanyl)imidazole-4-propionamide and 71 mg (0.24 mmol) of IVA-D-Pro-L-Pro-OH, 130 mg of (S)-N-[(1S,2S,4R)-1-(cyclohexylmethyl)-2-hydroxy-4-isopropyl-5-hexenyl]-α-[[N-[1-[(1-isovaleryl-D-prolyl)-L-prolyl]-3-phenyl-L-alanyl]amino]imidazole-4-propionamide as a solid, MS: 816 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 67 mg (0.24 mmol) of N-t-butoxycarbonyl-N-methyl-L-phenylalanine, 100 mg t-butyl [(S)-α-[[(S)-α-[[(S)-1-[[(1S,2S,4S)-1-(cyclohexylmethyl)-2-hydroxy-4-isopropyl-5-hexenyl]carbamoyl]-2-imidazol-4-ylethyl]carbamoyl]phenethyl]carbamoyl]phenethyl]methyl carbamate as a solid, MS: 799 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 71 mg (0.24 mmol) of IVA-D-Pro-Pro-OH, 141 mg of (2S,3S,5S)-1-cyclohexyl-2-[(3-methylbutyryl)-D-Pro-Pro-Phe-His-NH]-5-isopropyl-6-hepten-3-ol as a solid, MS: 816 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole- 4-propionamide and 74 mg (0.24 mmol) of Boc-(Δ3-deshydro)-Pro-Pro-OH, 125 mg of (2S,3S,5S)-2-[[[(S)-1-Boc-3-pyrrolin-2-yl]carbonyl]-Pro-Phe-His-NH]-1-cyclohexyl-5-isopropyl-6-hexen-3-ol as a solid, MS: 830 (M+H)30;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 75 mg (0.24 mmol) of Boc-Pro-D-Pro-OH- 135 mg of (2S,3S,5S)-2-(Boc-Pro-D-Pro-Phe-His-NH)-1-cyclohexyl-5-isopropyl-6-hepten-3-ol as a solid, MS: 832 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 75 mg (0.24 mmol) of Boc-D-Pro-D-Pro-OH, 133 mg of (2S,3S,5S)-2-(Boc-D-Pro-D-Pro-Phe-His-NH)-1-cyclohexyl-5-isopropyl-6-hepten-3-ol as a solid, MS: 832 (M+H)+:

From 110 mg (0.20 mmol) of (S)-α-(Phemethylamino)-N-[(1S,2S,4S)-1-(cyclohexylmethyl)-2-hydroxy-4-isopropyl-5-hexenyl]imidazole-4-propionamide and 75 mg (0.24 mmol) of Boc-D-Pro-Pro-OH, 87 mg of (S)-α-[Boc-D-Pro-Pro-Phe-N(CH3)]N-[(1S,2S,4S)-1-(cyclohexylmethyl)-2-hydroxy-4-isopropyl-5-hexenyl]imidazole-4-propionamide as a solid, MS: 846 (M+H)+;

From 107 mg (0.20 mmol) of N-[(1S,2S,4S)-1-(cyclohexylmethyl) 2-hydroxy-4 isopropyl 5-hexenyl]-α-(3-phenyl-L-alanyl)imidazole-4-propionamide and 55 mg (0.24 mmol) of (S)-N-t-butoxycarbonyl-piperidine-2-carboxylic acid, 127 mg of (2S,3S,5S)-1-[[[(S)-1-Boc-2-piperidinyl]carbonyl]-Phe-His-NH]-1-cyclohexyl-5-isopropyl-6-hepten-3-ol as a solid, Ms: 749 (M+H)+;

From 54 mg (0.10 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 49 mg (0.12 mmol) of Boc-D-Pro-D-Pro-Pro-OH, 57 mg of (2S,3S,5S)-2-(Boc-D-Pro-D-Pro-Pro-Phe-His-NH)-1-cyclohexyl-5-isopropyl-6-hepten-3-ol as a solid, MS: 927 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 56 mg (0.24 mmol) of (R)-N-t-butoxycarbonyl-thiazolidine-2-carboxylic acid, 126 mg of (2S,3S,5S)-2-[[[(R)-3-Boc-4-thiazolidinyl]carbonyl-Phe-His-NH]-1-cyclohexyl-5-isopropyl-6-hepten-3-ol as a solid, MS: 753 (M+H)+;

From 80 mg (0.123 mmol) of (2S,3S,5S)-1-[[[(S)-2-piperidinyl]carbonyl]-Phe-His-NH]-1-cyclohexyl-5-isopropyl-6-hepten-3-ol and 64 mg (0.30 mmol) of Boc-D-Pro-OH, 106 mg of (2S,3S,5S)-2-(Boc-D-Pro-Pip-Phe-His-NH)-1-cyclohexyl-5-isopropyl-6-hepten-3-ol as a solid, MS: 846 (M+);

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 79 mg (0.24 mmol) of (R)-N-t-butoxycarbonyl-thiazolidinyl-1-carbonyl-proline. 163 mg of (2S,3S,5S)-2-[[[(R)-3-Boc-4-thiazolidinyl]carbonyl]-Pro-Phe-His-NH]-1-cyclohexyl-5-isopropyl-6-hepten-3-ol as a solid, MS: 850 (M+H)+;

From 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 71 mg (0.24 mmol) of 2-(2-pyridyl)benzoic acid, 140 mg of (2S,3S,5S)-1-cyclohexyl-5-isopropyl-2-[[2-(2 -pyridyl)benzoyl]-Pro-Phe-His-NH]-6-hepten-3-ol in the form of the dihydrochloride. MS: 816 (M+H)+;

From 107 mg (0.20 mmol) of (N-[(1S,2S,4S)-1-(cyclohexylmethyl)-2-hydroxy-4-isopropyl-5-hexenyl]-α-(3-phenyl-L-alanyl)imidazole-4-propionamide and 57 mg (0.24 mmol) of 3-dimethyl-3-(1-imidazolyl)propionyl-Pro-Pro-OH, 160 mg of (2S,3S,5S)-1-cyclohexyl-2[(3, 3-dimethyl-3-imidazol-1-ylpropionyl)-Pro-Pro-Phe-His-NH]-5-isopropyl-6-hepten-3-ol as a solid. MS: 882 (M+H)+;

From 107 mg (0.20 mmol) of (N-[(1S,2S,4S)-1-(cyclohexylmethyl)-2-hydroxy-4-isopropyl-5-hexenyl]-α-(3-phenyl-L-alanyl)imidazole-4-propionamide and 77 mg (0.24 mmol) of N-(1-imidazolyl)acetyl-D-Pro-Pro-OH, 160 mg of (2S,3S,5S)-1-cyclohexyl-2-[(imidazol-1-ylacetyl)-D-Pro-Pro-Phe-His-NH]-5-isopropyl-6-hepten-3-ol in the form of the dihydrochloride as a solid. MS: 840 (M+H)+;

From 107 mg (0.20 mmol) of (N-[(1S,2S,4R)-1-(cyclohexylmethyl)-2-hydroxy-4-isopropyl-5-hexenyl]-α-(3-phenyl-L-alanyl)imidazole-4-propionamide and 77 mg (0.24 mmol) of N-(1-imidazolyl)acetyl-D-Pro-Pro-OH, 148 mg of (2S,3S,5R)-1-cyclohexyl-2-[(imidazol-1-ylacetyl) D-Pro-Pro-Phe-His-NH]-5-isopropyl-6-hepten-3-ol in the form of the dihydrochloride, as a solid, MS: 840 (M+H)+;

From 107 mg (0.20 mmol) of (N-[(1S,2S,4S)-1-(cyclohexylmethyl)-2-hydroxy-4-isopropyl 5-hexenyl]-α-(3-phenyl-L-alanyl)imidazole-4-propionamide and 83 mg (0.24 mmol) of benzyloxycarbonyl-Fro-pro-OH, 155 mg of (2S,3S 5S)-2-(benzyloxycarbonyl-Pro-Pro-Phe-His-NH)-1-cyclohexyl-5-isopropyl-6-hepten-3-ol as a solid, MS: 866 (M+H)+:

The (S)-α-(Phe-methylamino)-N-[(1S,2S,4S)-1-(cyclohexylmethyl)-2-hydroxy-4-isopropyl-5-hexenyl]imidazole-4-propionamide used as the starting material was prepared as follows:

A mixture of 1.50 g (4 mmol) of N-α-N-im-di-t-butoxycarbonyl-N-α-methylhistidine, 1.0 g (3.4 mmol) of (S,S,S)-6-amino-6-cyclohexylmethyl-4-isopropyl-1-hexen-5-ol hydrochloride, 1.33 g (3.5 mmol) of HBTU, 7.8 ml of N-methylmorpholine and 20 ml of dimethylformamide was stirred at room temperature for 4 hours. The solvent was evaporated under reduced pressure and the oily residue was dissolved in ether. The organic phase was washed firstly with a sodium bicarbonate solution and thereafter with saturated sodium chloride solution and, after drying over sodium sulfate, was evaporated under reduced pressure, to obtain 2.1 g of (S)-3-(t-butoxycarbonyl)-α-[1-(t-butoxycarbonyl)-N-methylformamido]-N-[(1S,2S,4S)-1-(cyclohexylmethyl)-2-hydroxy-4-isopropyl-5-hexenyl]imidazole-4-propionamide which was used directly in the next step.

2.1 g of (S)-3-(t-butoxycarbonyl)-α-[1-(t-butoxycarbonyl)-N-methylformamido]-N-[(1S,2S,4S)-1-(cyclohexylmethyl)-2-hydroxy-4-isopropyl-5-hexenyl]imidazole-4-propionamide were dissolved in 30 ml of 3N hydrogen chloride in dioxan and the mixture was left to stand at room temperature for 5 hours. 500 ml of ether were added and the precipitate formed was filtered off. The precipitate was washed with ether and dissolved in water. Solid sodium bicarbonate was added to the aqueous solution and the mixture was extracted several times with ethyl acetate, to obtain there was obtained 0.85 g of (S)-α-(N-methylformamido)-N-[(1S,2S,4S)-1-(cyclohexyl-methyl)-2-hydroxy-4-isopropyl-5-hexenyl)imidazole-4-propion-amide which was used directly in the next step.

A mixture of 0.85 g (2.1 mmol) of (S)-α-(N-methylformamido)-N-[(1S,2S,4S)-1-(cyclohexylmethyl)-2-hydroxy-4-isopropyl-5-hexenyl]imidazole-4-propionamide, 0.67 g (2.5 mmol) of N-t-butoxycarbonylphenylalanine, 0.84 g (2.2 mmol) of HBTU. 0.3 ml of N-methylmorpholine and 20 ml of dimethylformamide was to stand at room temperature for 60 hours and poured into a saturated sodium bicarbonate solution. The precipitate thus formed was filtered off and dissolved in ethyl acetate. The organic solution was dried over magnesium sulfate and evaporated under reduced pressure. The residue remaining was triturated with hexane and filtered off, to obtain 1.35 g of (S)-α-(Boc-Phe-methylamino)-N-[(1S,2S,4S)-1-(cyclohexylmethyl)-2-hydroxy-4-isopropyl-5-hexenyl]imidazole-4-propionamide in the form of a powder which was used directly in the next step.

1.3 g of (S)-α-(Boc-Phe-methylamino)-N-[(1S,2S,4S)-1-(cyclohexylmethyl)-2-hydroxy-4-isopropyl-5-hexenyl]-imidazole-4-propionamide were dissolved in 30 ml of 3N hydrogen chloride in dioxan and the mixture was left to stand at room temperature for 1 hour. Thereafter, 200 ml of ether were added and the mixture was stirred for 16 hours. The precipitate formed was filtered off, washed with ether and dissolved in water. Solid sodium bicarbonate was added to the aqueous solution and the mixture was then extracted several times with ethyl acetate, to obtain 0.97 g of (S)-α-(Phe-methylamino)-N-[(1S,2S,4S)-1-(cyclohexylmethyl)-2-hydroxy-4-isopropyl-5-hexenyl]imidazole-4-propionamide which was used directly in the next step.

The (2S,3S,5S)-1-[[[(S)-2-piperidinyl]carbonyl]Phe-His-NH]-1-cyclohexyl-5-isopropyl-6-hepten-3-ol which was also used as a starting material was prepared by cleaving off the t-butoxycarbonyl group from (2S,3S,5S)-1-[[[(S)-1-Boc-2-piperidinyl]carbonyl-Phe-His-NH]-1-cyclohexyl-5-isopropyl-6-hepten-3-ol by means of hydrochloric acid in dioxane and was used directly in the next step.

Example 72

A mixture of 31 mg (0.21 mmol) of N-cyano-dimethyldithiocarbamate, 107 mg (0.20 mmol) of N-[(1S,2S,4S)-1-(cyclohexylmethyl)-2-hydroxy-4-isopropyl-5-hexenyl]-α-(3-phenyl-L-alanyl)imidazole-4-propionamide and 1 ml of methanol was allowed to stand at room temperature for 24 hours. The solvent was evaporated under reduced pressure and the residue was digested with a 1:1 mixture of hexane and ether, to obtain 112 mg of (S)-N-[(1S,2S,4S)-1-(cyclohexylmethyl)-2-hydroxy-4-isopropyl-5-hexenyl]-α-[[N-[(cyanoimino)(methylthio)methyl]-3-phenyl-L-alanyl]amino]imidazole-4-propionamide as a solid, MS: 636 (M+H)+.

Example 73

100 mg of (2S,5S)-2-(Boc-D-Pro-Pro-Phe-His-NH)-1-cyclohexyl-5-isopropyl-6-hepten-3-ol were dissolved in 3 ml of 3.2N hydrogen chloride in dioxane, the solution was allowed to stand for 1 hour and the desired product was precipitated by the addition of ether. The precipitate was filtered off and dried under reduced pressure, to obtain 100 mg of [2S,3S,5S]-1-cyclohexyl-2-(D-Pro-Pro-Phe-His-NH)-5-isopropyl-6-hepten-3-ol in the form of the dihydrochloride as a solid MS: 732 (M+H)+.

EXAMPLE 74

41 mg (0.05 mmol) of (2S,3S,5S)-1-cyclohexyl-2-[(3-methylbutyryl)-D-Pro-Pro-Phe-His-NH]-5-isopropyl-6-hepten-3-ol were dissolved in 5 ml of methanol and hydrogenated in the presence of 20 mg of palladium-on-carbon (5%). After completion of the hydrogen uptake, the catalyst was filtered off and the solvent was evaporated under reduced pressure. Trituration of the residue with hexane and drying yielded 34 mg of (2S,3S,5S)-1-cyclohexyl-5-isopropyl-2-(isovaleryl-D-Pro-Pro-Phe-His-NH)-3-heptanol as a solid, MS: 818 (M+H)+.

The above hydrogenation can also used to produce the corresponding isomeric compound when carried out under the following conditions:

200 mg of starting material in 15 ml of methanol were hydrogenated in the presence of 50 mg of palladium-on-carbon (5%) and thereafter the mixture was worked-up as usual, to obtain 184 mg of (2S,3S,5R)-1-cyclohexyl-5-isopropyl-2-(isovaleryl-D-Pro-Pro-Phe-His-NH)-3-heptanol as a solid, MS: 818 (M+H)+.

Example 75

80 mg (0.25 mmol) of 3-(1-imidazolyl)propionyl-Pro-Pro-OH, 110 mg (0.20 mmol) of (S)-α-(Phe-methylamino)-N-[(1S,2S,4S)-1-(cyclohexylmethyl)-2-hydroxy-4-isopropyl-5-hexenyl]imidazole-4-propionamide, 84 mg (0.22 mmol) of HBTU, 0.03 ml of N-methylmorpholine and 2 ml of dimethylformamide was left to stand at room temperature for 16 hours. The reaction mixture was poured into 50 ml of a 5% sodium carbonate solution and the milky suspension was extracted several times with ethyl acetate. The organic extracts were dried over magnesium sulfate and evaporated under reduced pressure. The residue was dissolved in 10 ml of ethyl acetate and the solution was treated with 1.5 ml of a 3.0N solution of hydrogen chloride in dioxane. The precipitate thus formed was filtered off and dried, to obtain 143 mg of (S)-N-[(1S,2S, 4S)-1-(cyclohexylmethyl)-2-hydroxy-4-isopropyl-5-hexenyl]-α-[[3-(imidazol-1-yl)propionyl]-D-Pro-Pro-Phe-N-(methyl)]imidazole-4-propionamide hydrochloride as a solid, MS: 868 (M+H)+.

In a manner analogous to that described above, from 77 mg (0.24 mmol) of 2-(1-imidazolyl)acetyl-Pro-Pro-OH and 110 mg of (S)-α-(Phe-methylamino)-N-[(1S,2S,4S)-1-(cyclohexylmethyl)-2-hydroxy-4-isopropyl-5-hexenyl]imidazole-4-propionamide there were manufactured 155 mg of (S)-N-[(1S,2S,4S)-1-(cyclohexylmethyl)-2-hydroxy-4-isopropyl-5-hexenyl]-α-[(imidazol-1-ylethyl) D-Pro-Pro-Phe-N-(methyl)-]imidazole-4-propionamide dihydrochloride as a solid. MS: 840 (M+H)+.

Example 76

105 mg of (S)-N-((1S,2S,4S)-1-(cyclohexylmethyl)-2-hydroxy-4-isopropyl-5-hexenyl]-α-[[3-(imidazol-1-yl)propionyl]-D-Pro-Pro-Phe-N-(methyl)]imidazole-4-propionamide hydrochloride were dissolved in 15 ml of methanol and hydrogenated in the presence of 50 mg of palladium-on-carbon. After completion of the hydrogen uptake, the catalyst was filtered off and the filtrate was evaporated to dryness. The residue was triturated with ether and filtered off to obtain 65 mg of (2S,3S,5S)-1-cyclohexyl-2-[(3-imidazol-1-ylpropionyl)-D-Pro-Pro-Phe-His-NH]-5-isopropyl-3-heptanol dihydrochloride as a solid. MS: 856 (M+H)+.

Example 77

A sterile filtered aqueous solution of (S)-α-[(R)-2-benzyl-5,5-dimethyl-4-oxohexanamido]-N-[(1S,2S,4S)-1-(cyclohexylmethyl)-2-hydroxy-4-isopropyl-5-hexenyl]-imidazole-4-propionamide is mixed while warming with a sterile gelatine solution, which contains phenol as a preserving agent, under aseptic conditions so that 1.0 ml of solution has the following composition:

| | |
|---|---|
| (S)-α-[(R)-2-Benzyl-5,5-dimethyl-4-oxohexan-amido]-N-[(1S,2S,4S)-1-(cyclohexylmethyl)-2-hydroxy-4-isopropyl-5-hexenyl]imidazole-4-propionamide | 3.0 mg |
| Gelatine | 150.0 mg |
| Phenol | 4.7 mg |
| Distilled water to | 1.0 ml |

The mixture is filled into vials of 1.0 ml under aseptic conditions.

Example 78

5 mg of (S)-α-[(R)-2-benzyl-5,5-dimethyl-4-oxohexanamido]-N-[(1S,2S,4S)-1-(cyclohexylmethyl)-2-hydroxy-4-isopropyl-5-hexenyl]imidazole-4-propionamide are dissolved in 1 ml of an aqueous solution with 20 mg of mannitol. The solution is filtered sterile and filled under aseptic conditions into a 2 ml ampoule, cooled to a low temperature and lyophilized. Prior to administration, the lyophilizate is dissolved in 1 ml of distilled water or 1 ml of physiological saline. The solution is used intramuscularly or intravenously. This formulation can also be filled into double chamber injection ampoules.

Example 79

500 mg of finely milled (5.0 μm) of (S)-α-[(R)-2-benzyl-5,5-dimethyl-4-oxohexanamido]-N-[(1S,2S,4S)-1-(cyclohexylmethyl)-2-hydroxy-4-isopropyl-5-hexenyl]-imidazole-4-propionamide are suspended in a mixture of 3.5 ml of Myglyol 812 and 0.08 g of benzyl alcohol. This suspension is filled into a container having a dosage valve. 5.0 g of Freon 12 are filled into the container through the valve under pressure. The Freon is dissolved in the Myglyol-benzyl alcohol mixture by shaking. This spray container contains about 100 individual dosages which can be applied individually.

We claim:

1. A compound of the formula

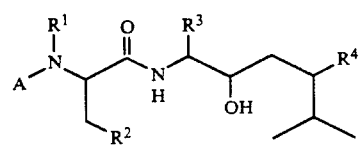

in which $R^1$ is hydrogen or methyl, $R^2$ is imidazol-4-yl, $R^3$ is isobutyl, cyclohexylmethyl, or benzyl, $R^4$ is phenyl, furyl, vinyl, ethyl, or 1,2-dihydroxyethyl and A is -Y-Z in which Y is a bivalent residue of optionally N- and/or α-methylated phenylglycine, cyclohexylglycine, phenylalanine, cyclohexylalanine, 4-fluorophenylalanine, 4-chlorophenyldamine, tyrosine, methionine, proline, α-napththylalanine, homophenylalanine, aspartic acid ethyl ester, or glutamic acid benzyl ester linked with Z at the N-terminal, and Z is hydrogen, a group of the formula

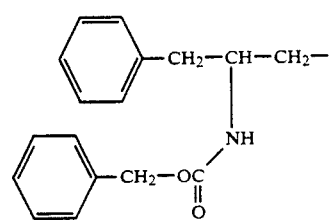

or

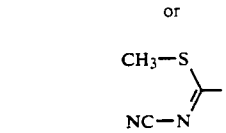

or is the residue, linked with Y at the C-terminal, of optionally N- and/or α-methylated natural amino acid with the L-configuration which is optionally N-substituted with the group $R^b$—CO— or $R^a$—O—CO— or of an epimer of such an amino acid with the D-configuration or of a dipeptide from two such amino acids or a tripeptide from three such amino acids or the group $R^b$—CO— or $R^a$—O—CO—, wherein $R^a$ is an optionally substituted residue selected from $C_{1-18}$alkyl; $C_{2-8}$alkenyl; $C_{2-8}$alkynyl; $C_{3-8}$cycloalkyl; $C_{3-8}$cycloalkenyl; $C_{5-10}$bicycloalkyl; $C_8$tricycloalkyl; $C_{5-10}$bicycloalkenyl; $C_{3-8}$cycloalkyl-$C_{3-8}$alkyl; $C_{3-8}$cycloalkenyl-$C_{1-8}$alkyl; $C_{3-8}$cycloalkyl-$C_{2-8}$alkenyl; $C_{3-8}$cycloalkenyl-$C_{2-8}$alkenyl; aryl selected from phenyl, naphthyl, and fluorenyl; a heteroaromatic residue, a heteroaromatic-$C_{1-8}$alkyl residue, an aryl $C_{1-8}$alkyl residue, or a heterocycle, wherein the heteroaromatic portion of the heteroaromatic and heteroaromatic-$C_{1-8}$-alkyl residues is selected from the group of moieties consisting of pyrrolyl, furyl, thienyl, imidazolyl, pyrazolyl, oxazolyl, thiazolyl, pyridyl, pyrazinyl, pyramidinyl, indolyl, quinolyl, isoquinolyl, quinoxalinyl and β-carbolinyl, or a benz-fused derivative of the above moieties, said above moieties which contain a nitrogen atom can be substituted at said nitrogen atom with alkyl, phenyl or phenylalkyl, said above moieties also can be substituted on at least one of the carbon atoms with alkyl, phenyl, phenylalkyl, halogen, hydroxy, alkoxy, phenylalkoxy, and oxo, the aryl portion of the aryl-$C_{1-8}$-alkyl residue is selected from the group consisting of phenyl, α- or β-naphthyl, indenyl and phenanthryl which can be substituted with at least one of alkyl, alkoxy, alkanoyloxy, amino, alkylamino, dialkylamino, alkanoylamino hydroxy, halogen trifluoromethyl and nitro, the heterocycle is selected from the group consisting of pyrrolidin-3-yl, 4-hydroxypyrrolidin-2-yl, 5-oxo-pyrrolidin-2-yl, piperidin-2yl, piperdin-3-yl, 1-methylpiperidin-2-yl, 1-methylpiperidin-3-yl, 1-methylpiperidin-4-yl, morpholin-2yl, morpholin-3yl, thiomorpholin-2yl, thiomorpholin-3yl, 1,4-dimethylpiperazin-2-yl, 2-indolinyl, 3-indolinyl, 1,2,3,4-tetrahydroquinol-2-, -3 or -4-yl, 1,2,3,4-tetrahydroisoquinol-1-, -3- or -4-yl, 1-oxo-1,2,3,4-tetrahydroisoquinol-3-yl, tertiary butoxy-carbonyl piperidin-2-yl, thiazolidin-4-yl, hexahydro-8a-methyl-5-oxo-5H-thiazolo[3,2-a]pyrid-3-yl, and tetrahydro-7a-methylpyrrolo[2,1-b]thiazol-3-yl; and $R^b$ is $R^a$ or hydrogen, the compound being in the form of an optionally pure diastereomer, diastereomeric mixture, diastereomeric racemate of mixture of diastereomeric racemates; or a pharmaceutically acceptable usable salt of the compound.

2. The compound of claim 1 wherein Z is the residue, linked with Y at the C-terminal of the L-configuration or its epimer of optionally substituted proline, prolylproline, histidine, methionine, N-methylphenylalanine, histindinylproline, prolylprolylproline, the amino group in each case is optionally substituted with t-butoxycarbonyl, benzoxycarbonyl, isovaleryl or the group $R^b$—CO—.

3. The compound of claim 2 wherein Z is Boc-D-Pro, D-Pro, 5-oxo-Pro, 4imidazolylproprionyl-Pro, 3-hydroxy-2-pyridylcarbonyl-Pro, dibenzylacetyl-Pro, isoalenylcarbonyl-Pro, Boc-Pro, Pro, t-butylcarbonyl-Pro, t-butylcarbonyl-Met, Boc-His, Boc-His(3Bom), 1-imidazolylproprioyl-D-Pro, Boc-D-Pro-Pro, Boc-Pro-Pro, isolalenyl-D-Pro-L-Pro, Boc-Pro-D-Pro, Boc-D-Pro-D-Pro, Boc-D-Pro-D-Pro-Pro, Boc-thiazolidin-4-ylcarbonyl-Pro, 2-(2-pyridyl)benzoyl-Pro, 2-(1-imidazolyl)-2,2-dimethylpropionyl-Pro-Pro, 1-imidazolylacetyl-D-Pro-Pro, benzyloxycarbonyl-Pro-Pro, D-Pro-Pro, 1-imidozolylpropioyl-D-Pro-Pro, or Boc-3-pyrrolin-2-yl-Pro.

4. The compound of claim 1 wherein Z is Boc, 3,3-dimethylbutyryl, isovaleryl, cyclopentylcarbonyl, Boc-aminovaleryl, aminoethylglycyl, 3-(4-hydroxyphenyl)-propionyl, 3-pyridylcarbonyl, 4-pyridyloxylcarbonyl, 3-pyridyloxylcarbonyl, 4-imidazolylzylcarbonyl, 1,3,4,5-cyclohexyl-carbonyl, 2-quinolylcarbonyl, methylcarbonylethylcarbonyl, 3-pyridylmethylcarbonyl, 4-chlorophenylvinylcarbonyl, 4-nitrophenylvinylcarbonyl, ethoxycarbonylvinylcarbonyl, diphenylaminocarbonyl, isobutoxycarbonyl, Boc-aminoisobutyryl, fluorenylmethylcarbonyl-2-t-butoxyalkyl, fluorenylmethoxycarbonyl, adamatylmethylcarbonyl, phenoxycarbonyl, 2,2,2-trichloroethoxy, Boc-aminocyclohexycarbonyl, 2-t-butyoxyalanyl, aminovaleryl, ethoxycarbonylethoxycarbonly, adamatylacetyl, 3-pyrridylacetyl, fluorenylacetyl, ethoxycarbonyl, 4-aminophenypropionyl, acetylpropionyl, 4-hydroxyphenylpropionyl, 3-pyridiylpropionyl, 4-imidozalylpropionyl, Boc-aminoisobutyl, 1-amino-2-hydroxyproprioyl, dibenzyaminoacarbonyl, morpholinecarbonyl, 4-biphenyloxyethylaminocarbonyl, N-Boc-2-azetidinecarbonyl, hexahydro-8a-methyl-5-oxo-5H-thiazole[3,2-a]pyridyl-3-carbonyl, tetrahydro-7a-methylpyrrolo[2,1-b]thiazolyl-3-carbonyl, Boc-aminovalerylaminoproprionyl, phentylacetyl, 2-pyridylcarbonyl, 2-(2-pyridyl)benzoyl, Boc-phenylalycyl, boc-2-piperidinylcarbonyl, or Boc-thiazolidin-4-ylcarbonyl.

5. A compound in accordance with claim 2, wherein Y is phenylalanine and Z is the residue, linked with Y at the C-terminal, of a N- and/or α-methylated natural amino acid with the L-configuration which is optionally N-substituted with the group $R^b$—CO— or $R^a$—O—CO— or of an epimer of such an amino acid with the D-configuration or of a dipeptide from two such amino acids or the group $R^b$—CO— or $R^a$—O—CO—, wherein $R^4$ is an optionally substituted, saturated or unsaturated aliphatic, cycloaliphatic, cycloaliphatic-aliphatic hydrocarbon residue having from 1 to 18 carbon atoms, an optionally substututed aromatic, heteroaromatic, aromatic-aliphatic or heteroaromatic-aliphatic hydrocarbon residue having from 1 to 18 carbon atoms or an optionally substituted, saturated 5- or 6-membered heterocycle and $R^b$ is hydrogen or has the same meaning as $R^a$, the residue, linked with Y at the C-terminal, of proline, prolyproline or histidinylproline, whereby the amino group in each case is substituted t-butoxy-carbonyl, benzoxycarbonyl, isovaleryl or the group $R^b$—CO— in which $R^b$ is a heteroaromatic-aliphatic hydrocarbon residue having from 1 to 10 carbon atoms or a saturated 5- or 6-membered heterocycle.

6. A compound in accordance with claim 1 which is t-butyl(R)-2-[[(S)-α-]](S)-1-[(1S,2S,4S)-1-cyclohexylmethyl-2-hydroxy-4-isopropylhexyl]-2-imidazol-4-ylethyl]carbamoyl]phenethyl]carbamoyl]-1-pyrrolidinecarboxylate.

7. A compound in accordance with claim 2 which is (2S,3S,5S)-2-(Boc-D-Pro-Phe-His-NH)-1-cyclohexyl-5-isopropyl-6-hepten-3-ol.

8. A compound in accordance with claim 1 which is (2S,5S)-2-(Boc-D-Pro-Pro-Phe-His-NH)-1-cyclohexyl-5-isopropyl-6-hepten-3-ol.

9. A compound in accordance with claim 1 which is N-(S)-[(1S,2S,4S)-1-(Cyclohexylmethyl-2-hydroxy-4-isopropyl-5-hexenyl]-α-[(S)-α-3-methyl-butyramido]imidazole-4-propionamide.

10. A compound in accordance with claim 1 which is t-butyl [(S)-α-[[(S)-1-[[(1S,2S,4S)-1-cyclohexylmethyl-2-hydroxy-4-isopropyl-5-hexenyl]carbamoyl]-2-imidazol-4-ylethyl]carbamoyl]phenethyl]carbamate.

11. A compound in accordance with claim 1 which is t-butyl [(S)-α-[[(S)-1-[[(1S,2S,4S)-1-cyclohexylmethyl-2-hydroxy-4-isopropylhexyl]carbamoyl]-2-imidazol-4-ylethyl]carbamoyl]phenethyl]carbamate.

* * * * *

UNITED STATES PATENT AND TRADEMARK OFFICE
CERTIFICATE OF CORRECTION

PATENT NO. : 5,250,517
DATED : October 5, 1993
INVENTOR(S) : Quirico Branca, Albrecht Edenhofer, Eva-Maria Gutknecht, Werner Neidhart, Henri Ramuz and Wolfgang Wostl It is certified that error appears in the above-identified patent and that said Letters Patent is hereby corrected as shown below:

Column 83, line 21, change "piperidin-2yl," to -- piperidin-2-yl, --;

Column 83, line 23, change "morpholin-2yl," to -- morpholin-2-yl, --;

Column 83, line 24, change "pholin-3yl, thiomorpholin-2yl, thiomorpholin-3yl," to -- pholin-3-yl, thiomorpholin-2-yl, thiomorpholin-3-yl, --;

Column 83, line 34, change "of" to -- or --; (first occurrence).

Column 84, line 5, change "ethoxycarbonylethoxycarbonly" to -- ethoxycarbonylethoxycarbonyl --;

Column 84, line 31, change "substututed" to -- substituted --;

Column 84, line 44, change "t-butyl(R)-2-[[(S)-a-]]" to -- t-butyl(R)-2-[[(S)-a-[[ --.

Signed and Sealed this

Ninth Day of August, 1994

Attest:

BRUCE LEHMAN

Attesting Officer          Commissioner of Patents and Trademarks